(12) United States Patent
Scheib et al.

(10) Patent No.: US 8,485,413 B2
(45) Date of Patent: Jul. 16, 2013

(54) SURGICAL STAPLING INSTRUMENT COMPRISING AN ARTICULATION JOINT

(75) Inventors: Charles J. Scheib, Loveland, OH (US); Gary S. Jaworek, Cincinnati, OH (US); Steven G. Hall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 643 days.

(21) Appl. No.: 12/366,514

(22) Filed: Feb. 5, 2009

(65) Prior Publication Data
US 2010/0193567 A1 Aug. 5, 2010

(51) Int. Cl.
*A61B 17/068* (2006.01)

(52) U.S. Cl.
USPC ..... 227/176.1; 227/19; 227/175.1; 227/179.1

(58) Field of Classification Search
USPC ...................... 227/175.1–182.1, 19
See application file for complete search history.

(56) References Cited

U.S. PATENT DOCUMENTS

| | | | |
|---|---|---|---|
| 2,853,074 A | 9/1958 | Olson | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 3,851,196 A | 11/1974 | Hinds | |
| RE28,932 E | 8/1976 | Noiles et al. | |
| 4,169,990 A | 10/1979 | Lerdman | |
| 4,331,277 A | 5/1982 | Green | |
| 4,383,634 A | 5/1983 | Green | |
| 4,393,728 A | 7/1983 | Larson et al. | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,473,077 A * | 9/1984 | Noiles et al. | 227/179.1 |
| 4,475,679 A | 10/1984 | Fleury, Jr. | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

U.S. Appl. No. 12/366,539, filed Feb. 5, 2009.

(Continued)

*Primary Examiner* — Brian D Nash

(57) ABSTRACT

In various embodiments, a surgical stapling instrument can comprise a plurality of magnetic elements configured to articulate an end effector of the surgical instrument. The surgical instrument can comprise at least one electromagnet which can be selectively activated, or polarized, to generate a magnetic field sufficient to motivate a second magnetic element, such as a permanent magnet and/or an iron core, for example, mounted to the end effector. In certain embodiments, a surgical stapling instrument can comprise a plurality of magnetic elements configured to open and/or close an end effector of the surgical instrument. In at least one embodiment, a surgical stapling instrument can comprise a plurality of magnetic elements configured to advance and/or retract a firing bar, cutting member, and/or staple sled within the surgical instrument in order to incise and/or staple tissue positioned within an end effector of the surgical instrument.

14 Claims, 50 Drawing Sheets

U.S. PATENT DOCUMENTS

| | | | |
|---|---|---|---|
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,522,327 A | 6/1985 | Korthoff et al. | |
| 4,530,453 A | 7/1985 | Green | |
| 4,566,620 A | 1/1986 | Green et al. | |
| 4,571,213 A * | 2/1986 | Ishimoto | 446/468 |
| 4,573,622 A | 3/1986 | Green et al. | |
| 4,580,712 A | 4/1986 | Green | |
| 4,610,383 A | 9/1986 | Rothfuss et al. | |
| 4,619,262 A | 10/1986 | Taylor | |
| 4,629,107 A | 12/1986 | Fedotov et al. | |
| 4,632,290 A | 12/1986 | Green et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,743,214 A * | 5/1988 | Tai-Cheng | 446/129 |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,844,068 A | 7/1989 | Arata et al. | |
| 4,869,414 A | 9/1989 | Green et al. | |
| 4,869,415 A | 9/1989 | Fox | |
| 4,941,623 A | 7/1990 | Pruitt | |
| 4,944,443 A | 7/1990 | Oddsen et al. | |
| 5,065,929 A | 11/1991 | Schulze et al. | |
| 5,071,430 A | 12/1991 | de Salis et al. | |
| 5,129,570 A | 7/1992 | Schulze et al. | |
| 5,137,198 A | 8/1992 | Nobis et al. | |
| 5,139,513 A | 8/1992 | Segato | |
| 5,142,932 A | 9/1992 | Moya et al. | |
| 5,158,567 A | 10/1992 | Green | |
| 5,221,036 A | 6/1993 | Takase | |
| 5,222,975 A | 6/1993 | Crainich | |
| 5,236,440 A | 8/1993 | Hlavacek | |
| 5,258,009 A | 11/1993 | Conners | |
| 5,271,543 A * | 12/1993 | Grant et al. | 227/179.1 |
| 5,282,829 A | 2/1994 | Hermes | |
| 5,304,204 A | 4/1994 | Bregen | |
| 5,312,023 A | 5/1994 | Green et al. | |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,395,033 A | 3/1995 | Byrne et al. | |
| 5,405,072 A | 4/1995 | Zlock et al. | |
| 5,413,272 A | 5/1995 | Green et al. | |
| 5,415,334 A | 5/1995 | Williamson, IV et al. | |
| 5,417,361 A | 5/1995 | Williamson, IV | |
| 5,425,745 A | 6/1995 | Green et al. | |
| 5,433,721 A * | 7/1995 | Hooven et al. | 606/143 |
| 5,478,354 A | 12/1995 | Tovey et al. | |
| 5,480,089 A | 1/1996 | Blewett | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,505,363 A | 4/1996 | Green et al. | |
| 5,509,596 A | 4/1996 | Green et al. | |
| 5,529,235 A | 6/1996 | Boiarski et al. | |
| 5,533,661 A | 7/1996 | Main et al. | |
| 5,535,934 A | 7/1996 | Boiarski et al. | |
| 5,540,375 A | 7/1996 | Bolanos et al. | |
| 5,542,594 A | 8/1996 | McKean et al. | |
| 5,553,765 A | 9/1996 | Knodel et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A * | 5/1997 | Schulze et al. | 227/176.1 |
| 5,632,433 A | 5/1997 | Grant et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,527 A | 9/1997 | Cook | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,711,472 A | 1/1998 | Bryan | |
| 5,713,505 A | 2/1998 | Huitema | |
| 5,715,987 A | 2/1998 | Kelley et al. | |
| 5,718,360 A | 2/1998 | Green et al. | |
| 5,725,554 A | 3/1998 | Simon et al. | |
| 5,730,758 A | 3/1998 | Allgeyer | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A | 7/1998 | Koukline | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,820,009 A | 10/1998 | Melling et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson, IV et al. | |
| 5,901,895 A | 5/1999 | Heaton et al. | |
| 5,911,353 A | 6/1999 | Bolanos et al. | |
| 5,915,616 A | 6/1999 | Viola et al. | |
| 5,937,951 A | 8/1999 | Izuchukwu et al. | |
| 5,941,442 A | 8/1999 | Geiste et al. | |
| 5,954,259 A | 9/1999 | Viola et al. | |

| Patent No. | | Date | Inventor(s) |
|---|---|---|---|
| 6,010,054 | A | 1/2000 | Johnson et al. |
| 6,032,849 | A | 3/2000 | Mastri et al. |
| 6,053,390 | A | 4/2000 | Green et al. |
| 6,083,242 | A | 7/2000 | Cook |
| 6,099,551 | A | 8/2000 | Gabbay |
| 6,102,271 | A | 8/2000 | Longo et al. |
| 6,119,913 | A | 9/2000 | Adams et al. |
| 6,126,058 | A | 10/2000 | Adams et al. |
| 6,171,330 | B1 | 1/2001 | Benchetrit |
| 6,193,129 | B1 | 2/2001 | Bittner et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,330,965 | B1 | 12/2001 | Milliman et al. |
| 6,387,113 | B1 | 5/2002 | Hawkins et al. |
| RE37,814 | E | 8/2002 | Allgeyer |
| 6,428,070 | B1 | 8/2002 | Takanashi et al. |
| 6,429,611 | B1 | 8/2002 | Li |
| 6,443,973 | B1 | 9/2002 | Whitman |
| 6,488,196 | B1 | 12/2002 | Fenton, Jr. |
| 6,488,197 | B1 | 12/2002 | Whitman |
| 6,491,201 | B1 | 12/2002 | Whitman |
| 6,505,768 | B2 | 1/2003 | Whitman |
| 6,517,565 | B1 | 2/2003 | Whitman et al. |
| 6,578,751 | B2 | 6/2003 | Hartwick |
| 6,588,643 | B2 | 7/2003 | Bolduc et al. |
| 6,601,749 | B2 | 8/2003 | Sullivan et al. |
| 6,616,686 | B2 | 9/2003 | Coleman et al. |
| 6,619,529 | B2 | 9/2003 | Green et al. |
| 6,629,630 | B2 | 10/2003 | Adams |
| 6,629,988 | B2 | 10/2003 | Weadock |
| 6,644,532 | B2 | 11/2003 | Green et al. |
| 6,681,978 | B2 | 1/2004 | Geiste et al. |
| 6,681,979 | B2 | 1/2004 | Whitman |
| 6,695,199 | B2 | 2/2004 | Whitman |
| 6,698,643 | B2 | 3/2004 | Whitman |
| 6,716,233 | B1 | 4/2004 | Whitman |
| 6,755,338 | B2 * | 6/2004 | Hahnen et al. ............ 227/175.1 |
| 6,769,594 | B2 | 8/2004 | Orban, III |
| 6,777,838 | B2 | 8/2004 | Miekka et al. |
| 6,786,382 | B1 | 9/2004 | Hoffman |
| 6,805,273 | B2 | 10/2004 | Bilotti et al. |
| 6,817,508 | B1 | 11/2004 | Racenet et al. |
| 6,817,509 | B2 | 11/2004 | Geiste et al. |
| 6,830,174 | B2 | 12/2004 | Hillstead et al. |
| 6,843,403 | B2 | 1/2005 | Whitman |
| RE38,708 | E | 3/2005 | Bolanos et al. |
| 6,874,669 | B2 | 4/2005 | Adams et al. |
| 6,877,647 | B2 | 4/2005 | Green et al. |
| 6,905,057 | B2 | 6/2005 | Swayze et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,852 | B2 | 11/2005 | Shelton, IV et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,986,451 | B1 | 1/2006 | Mastri et al. |
| 6,988,650 | B2 | 1/2006 | Schwemberger et al. |
| 7,000,818 | B2 | 2/2006 | Shelton, IV et al. |
| 7,000,819 | B2 | 2/2006 | Swayze et al. |
| 7,032,798 | B2 | 4/2006 | Whitman et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,731 | B2 | 6/2006 | Shelton, IV et al. |
| 7,056,330 | B2 | 6/2006 | Gayton |
| 7,070,083 | B2 | 7/2006 | Jankowski |
| 7,077,856 | B2 | 7/2006 | Whitman |
| 7,080,769 | B2 | 7/2006 | Vresh et al. |
| 7,083,075 | B2 | 8/2006 | Swayze et al. |
| 7,108,709 | B2 | 9/2006 | Cummins |
| 7,111,769 | B2 | 9/2006 | Wales et al. |
| 7,114,642 | B2 | 10/2006 | Whitman |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,140,527 | B2 | 11/2006 | Ehrenfels et al. |
| 7,143,926 | B2 | 12/2006 | Shelton, IV et al. |
| 7,147,138 | B2 | 12/2006 | Shelton, IV |
| 7,147,139 | B2 | 12/2006 | Schwemberger et al. |
| 7,156,863 | B2 | 1/2007 | Sonnenschein et al. |
| 7,159,750 | B2 | 1/2007 | Racenet et al. |
| 7,168,604 | B2 | 1/2007 | Milliman et al. |
| 7,182,239 | B1 | 2/2007 | Myers |
| 7,188,758 | B2 | 3/2007 | Viola et al. |
| 7,207,471 | B2 | 4/2007 | Heinrich et al. |
| 7,207,472 | B2 | 4/2007 | Wukusick et al. |
| 7,210,609 | B2 | 5/2007 | Leiboff et |
| 7,213,736 | B2 | 5/2007 | Wales et al. |
| 7,220,272 | B2 | 5/2007 | Weadock |
| 7,225,964 | B2 | 6/2007 | Mastri et al. |
| 7,234,624 | B2 | 6/2007 | Gresham et al. |
| 7,237,708 | B1 | 7/2007 | Guy et al. |
| 7,238,195 | B2 | 7/2007 | Viola |
| 7,246,734 | B2 | 7/2007 | Shelton, IV |
| 7,258,262 | B2 | 8/2007 | Mastri et al. |
| 7,278,562 | B2 | 10/2007 | Mastri et al. |
| 7,278,563 | B1 | 10/2007 | Green |
| 7,296,724 | B2 | 11/2007 | Green et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,328,828 | B2 | 2/2008 | Ortiz et al. |
| 7,328,829 | B2 | 2/2008 | Arad et al. |
| 7,334,717 | B2 | 2/2008 | Rethy et al. |
| 7,354,447 | B2 | 4/2008 | Shelton, IV et al. |
| 7,364,060 | B2 | 4/2008 | Milliman |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,398,907 | B2 | 7/2008 | Racenet et al. |
| 7,398,908 | B2 | 7/2008 | Holsten et al. |
| 7,404,508 | B2 | 7/2008 | Smith et al. |
| 7,404,509 | B2 | 7/2008 | Ortiz et al. |
| 7,407,075 | B2 | 8/2008 | Holsten et al. |
| 7,407,078 | B2 | 8/2008 | Shelton, IV et al. |
| 7,410,086 | B2 | 8/2008 | Ortiz et al. |
| 7,416,101 | B2 | 8/2008 | Shelton, IV et al. |
| 7,419,080 | B2 | 9/2008 | Smith et al. |
| 7,422,136 | B1 | 9/2008 | Marczyk |
| 7,422,139 | B2 | 9/2008 | Shelton, IV et al. |
| 7,424,965 | B2 | 9/2008 | Racenet et al. |
| 7,431,188 | B1 | 10/2008 | Marczyk |
| 7,431,189 | B2 | 10/2008 | Shelton, IV et al. |
| 7,431,730 | B2 | 10/2008 | Viola |
| 7,434,717 | B2 | 10/2008 | Shelton, IV et al. |
| 7,438,209 | B1 | 10/2008 | Hess et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,455,208 | B2 | 11/2008 | Wales et al. |
| 7,464,846 | B2 | 12/2008 | Shelton, IV et al. |
| 7,464,849 | B2 | 12/2008 | Shelton, IV et al. |
| 7,467,740 | B2 | 12/2008 | Shelton, IV et al. |
| 7,472,815 | B2 | 1/2009 | Shelton, IV et al. |
| 7,481,347 | B2 | 1/2009 | Roy |
| 7,481,349 | B2 | 1/2009 | Holsten et al. |
| 7,490,749 | B2 | 2/2009 | Schall et al. |
| 7,494,039 | B2 | 2/2009 | Racenet et al. |
| 7,500,979 | B2 | 3/2009 | Hueil et al. |
| 7,506,790 | B2 | 3/2009 | Shelton, IV |
| 7,506,791 | B2 | 3/2009 | Omaits et al. |
| 7,510,107 | B2 * | 3/2009 | Timm et al. ................ 227/180.1 |
| 7,546,940 | B2 | 6/2009 | Milliman et al. |
| 7,556,186 | B2 | 7/2009 | Milliman |
| 7,559,450 | B2 | 7/2009 | Wales et al. |
| 7,568,604 | B2 | 8/2009 | Ehrenfels et al. |
| 7,575,144 | B2 | 8/2009 | Ortiz et al. |
| 7,611,038 | B2 | 11/2009 | Racenet et al. |
| 7,624,902 | B2 | 12/2009 | Marczyk et al. |
| 7,631,793 | B2 | 12/2009 | Rethy et al. |
| 7,651,498 | B2 | 1/2010 | Shifrin et al. |

| Patent/Publication | Date | Inventor |
|---|---|---|
| 7,665,646 B2 | 2/2010 | Prommersberger |
| 7,699,204 B2 | 4/2010 | Viola |
| 7,717,312 B2 | 5/2010 | Beetel |
| 7,721,930 B2 | 5/2010 | McKenna et al. |
| 7,726,537 B2 | 6/2010 | Olson et al. |
| 7,726,538 B2 | 6/2010 | Holsten et al. |
| 7,743,960 B2 | 6/2010 | Whitman et al. |
| 7,766,209 B2 | 8/2010 | Baxter, III et al. |
| 7,780,054 B2 | 8/2010 | Wales |
| 7,784,662 B2 | 8/2010 | Wales et al. |
| 7,793,812 B2 | 9/2010 | Moore et al. |
| 7,810,692 B2 | 10/2010 | Hall et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,850,642 B2 | 12/2010 | Moll et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,950,560 B2 | 5/2011 | Zemlok et al. |
| 7,954,686 B2 | 6/2011 | Baxter, III et al. |
| 7,959,051 B2 | 6/2011 | Smith et al. |
| 7,980,443 B2 | 7/2011 | Scheib et al. |
| 8,002,795 B2 | 8/2011 | Beetel |
| 8,011,551 B2 | 9/2011 | Marczyk et al. |
| 8,020,743 B2 | 9/2011 | Shelton, Iv |
| D650,074 S | 12/2011 | Hunt et al. |
| 2002/0117534 A1 | 8/2002 | Green et al. |
| 2002/0143252 A1* | 10/2002 | Dunne et al. .................. 600/437 |
| 2004/0006372 A1 | 1/2004 | Racenet et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0075561 A1* | 4/2005 | Golden .................. 600/424 |
| 2005/0096683 A1 | 5/2005 | Ellins et al. |
| 2005/0103819 A1 | 5/2005 | Racenet et al. |
| 2005/0145675 A1 | 7/2005 | Hartwick et al. |
| 2005/0184121 A1 | 8/2005 | Heinrich |
| 2005/0187545 A1* | 8/2005 | Hooven et al. .................. 606/41 |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025812 A1 | 2/2006 | Shelton, IV |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0108393 A1 | 5/2006 | Heinrich et al. |
| 2006/0161185 A1 | 7/2006 | Saadat et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0259073 A1 | 11/2006 | Miyamoto et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0034668 A1 | 2/2007 | Holsten et al. |
| 2007/0045379 A1 | 3/2007 | Shelton, IV |
| 2007/0073341 A1 | 3/2007 | Smith et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0135803 A1* | 6/2007 | Belson .................. 606/1 |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1* | 9/2007 | Ortiz et al. .................. 227/175.1 |
| 2007/0225562 A1 | 9/2007 | Spivey et al. |
| 2007/0233053 A1 | 10/2007 | Shelton, IV et al. |
| 2007/0246505 A1 | 10/2007 | Pace-Floridia et al. |
| 2007/0249999 A1* | 10/2007 | Sklar et al. .................. 604/101.05 |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |

| | | | | | |
|---|---|---|---|---|---|
| 2008/0237296 A1 | 10/2008 | Boudreaux et al. | 2010/0181364 A1 | 7/2010 | Shelton, IV et al. |
| 2008/0251568 A1 | 10/2008 | Zemlok et al. | 2010/0193566 A1 | 8/2010 | Scheib et al. |
| 2008/0283570 A1 | 11/2008 | Boyden et al. | 2010/0193568 A1 | 8/2010 | Scheib et al. |
| 2008/0290134 A1 | 11/2008 | Bettuchi et al. | 2010/0193569 A1 | 8/2010 | Yates et al. |
| 2008/0296343 A1 | 12/2008 | Schall et al. | 2010/0198220 A1 | 8/2010 | Boudreaux et al. |
| 2008/0296345 A1 | 12/2008 | Shelton, IV et al. | 2010/0200637 A1 | 8/2010 | Beetel |
| 2008/0296346 A1 | 12/2008 | Shelton, IV et al. | 2010/0213241 A1 | 8/2010 | Bedi et al. |
| 2008/0296347 A1 | 12/2008 | Shelton, IV et al. | 2010/0222901 A1 | 9/2010 | Swayze et al. |
| 2008/0297287 A1 | 12/2008 | Shachar et al. | 2010/0224669 A1 | 9/2010 | Shelton, IV et al. |
| 2008/0300579 A1 | 12/2008 | Broehl et al. | 2010/0237132 A1 | 9/2010 | Measamer et al. |
| 2008/0300580 A1 | 12/2008 | Shelton, IV et al. | 2010/0243707 A1 | 9/2010 | Olson et al. |
| 2008/0300613 A1 | 12/2008 | Shelton, IV et al. | 2010/0243708 A1 | 9/2010 | Aranyi et al. |
| 2008/0308601 A1 | 12/2008 | Timm et al. | 2010/0243709 A1 | 9/2010 | Hess et al. |
| 2008/0308602 A1 | 12/2008 | Timm et al. | 2010/0264193 A1 | 10/2010 | Huang et al. |
| 2008/0308603 A1 | 12/2008 | Shelton, IV et al. | 2010/0264194 A1 | 10/2010 | Huang et al. |
| 2008/0308604 A1 | 12/2008 | Timm et al. | 2010/0268030 A1* | 10/2010 | Viola et al. .................. 600/117 |
| 2008/0308606 A1 | 12/2008 | Timm et al. | 2010/0276471 A1 | 11/2010 | Whitman |
| 2008/0308607 A1 | 12/2008 | Timm et al. | 2010/0294827 A1 | 11/2010 | Boyden et al. |
| 2008/0308608 A1 | 12/2008 | Prommersberger | 2010/0294829 A1 | 11/2010 | Giordano et al. |
| 2008/0314954 A1 | 12/2008 | Boudreaux | 2010/0301095 A1 | 12/2010 | Shelton, IV et al. |
| 2008/0314955 A1 | 12/2008 | Boudreaux et al. | 2010/0301096 A1 | 12/2010 | Moore et al. |
| 2008/0314956 A1 | 12/2008 | Boudreaux | 2010/0305552 A1 | 12/2010 | Shelton, IV et al. |
| 2008/0314957 A1 | 12/2008 | Boudreaux | 2010/0308100 A1 | 12/2010 | Boudreaux |
| 2008/0314960 A1 | 12/2008 | Marczyk et al. | 2011/0003528 A1* | 1/2011 | Lam ............................. 446/330 |
| 2008/0314961 A1 | 12/2008 | Boudreaux et al. | 2011/0006099 A1 | 1/2011 | Hall et al. |
| 2008/0314962 A1 | 12/2008 | Boudreaux | 2011/0006101 A1 | 1/2011 | Hall et al. |
| 2009/0001121 A1 | 1/2009 | Hess et al. | 2011/0006103 A1 | 1/2011 | Laurent et al. |
| 2009/0001122 A1 | 1/2009 | Prommersberger et al. | 2011/0011914 A1 | 1/2011 | Baxter, III et al. |
| 2009/0001123 A1 | 1/2009 | Morgan et al. | 2011/0011915 A1 | 1/2011 | Shelton, IV |
| 2009/0001124 A1 | 1/2009 | Hess et al. | 2011/0017801 A1 | 1/2011 | Zemlok et al. |
| 2009/0001125 A1 | 1/2009 | Hess et al. | 2011/0024477 A1 | 2/2011 | Hall et al. |
| 2009/0001126 A1 | 1/2009 | Hess et al. | 2011/0024478 A1 | 2/2011 | Shelton, IV |
| 2009/0001128 A1 | 1/2009 | Weisenburgh, II et al. | 2011/0024479 A1 | 2/2011 | Swensgard et al. |
| 2009/0001130 A1 | 1/2009 | Hess et al. | 2011/0036887 A1 | 2/2011 | Zemlok et al. |
| 2009/0005807 A1 | 1/2009 | Hess et al. | 2011/0042441 A1 | 2/2011 | Shelton, IV et al. |
| 2009/0005808 A1 | 1/2009 | Hess et al. | 2011/0060363 A1 | 3/2011 | Hess et al. |
| 2009/0005809 A1 | 1/2009 | Hess et al. | 2011/0062212 A1 | 3/2011 | Shelton, IV et al. |
| 2009/0012556 A1 | 1/2009 | Boudreaux et al. | 2011/0068145 A1 | 3/2011 | Bedi et al. |
| 2009/0057369 A1 | 3/2009 | Smith et al. | 2011/0068148 A1 | 3/2011 | Hall et al. |
| 2009/0076534 A1 | 3/2009 | Shelton, IV et al. | 2011/0084112 A1 | 4/2011 | Kostrzewski |
| 2009/0108048 A1 | 4/2009 | Zemlok et al. | 2011/0084113 A1 | 4/2011 | Bedi et al. |
| 2009/0114701 A1 | 5/2009 | Zemlok et al. | 2011/0084115 A1 | 4/2011 | Bedi et al. |
| 2009/0149871 A9 | 6/2009 | Kagan et al. | 2011/0087276 A1 | 4/2011 | Bedi et al. |
| 2009/0206125 A1 | 8/2009 | Huitema et al. | 2011/0101065 A1 | 5/2011 | Milliman |
| 2009/0206126 A1 | 8/2009 | Huitema et al. | 2011/0114697 A1 | 5/2011 | Baxter, III et al. |
| 2009/0206131 A1 | 8/2009 | Weisenburgh, II et al. | 2011/0114698 A1 | 5/2011 | Baxter, III et al. |
| 2009/0206132 A1 | 8/2009 | Hueil et al. | 2011/0114699 A1 | 5/2011 | Baxter, III et al. |
| 2009/0206133 A1 | 8/2009 | Morgan et al. | 2011/0114700 A1 | 5/2011 | Baxter, III et al. |
| 2009/0206137 A1 | 8/2009 | Hall et al. | 2011/0118761 A1 | 5/2011 | Baxter, III et al. |
| 2009/0206139 A1 | 8/2009 | Hall et al. | 2011/0121051 A1 | 5/2011 | Shelton, IV et al. |
| 2009/0206141 A1 | 8/2009 | Huitema et al. | 2011/0121052 A1 | 5/2011 | Shelton, IV et al. |
| 2009/0206142 A1 | 8/2009 | Huitema et al. | 2011/0125176 A1 | 5/2011 | Yates et al. |
| 2009/0206143 A1 | 8/2009 | Huitema et al. | 2011/0125177 A1 | 5/2011 | Yates et al. |
| 2009/0209946 A1 | 8/2009 | Swayze et al. | 2011/0132962 A1 | 6/2011 | Hall et al. |
| 2009/0209990 A1 | 8/2009 | Yates et al. | 2011/0132963 A1 | 6/2011 | Giordano et al. |
| 2009/0218384 A1 | 9/2009 | Aranyi | 2011/0132964 A1 | 6/2011 | Weisenburgh, II et al. |
| 2009/0242610 A1 | 10/2009 | Shelton, IV et al. | 2011/0132965 A1 | 6/2011 | Moore et al. |
| 2009/0255974 A1 | 10/2009 | Viola | 2011/0139852 A1 | 6/2011 | Zingman |
| 2009/0255975 A1 | 10/2009 | Zemlok et al. | 2011/0144430 A1 | 6/2011 | Spivey et al. |
| 2009/0255976 A1 | 10/2009 | Marczyk et al. | 2011/0147433 A1 | 6/2011 | Shelton, IV et al. |
| 2009/0255977 A1 | 10/2009 | Zemlok | 2011/0147434 A1 | 6/2011 | Hueil et al. |
| 2009/0255978 A1 | 10/2009 | Viola et al. | 2011/0155780 A1 | 6/2011 | Boudreaux |
| 2010/0001036 A1 | 1/2010 | Marczyk et al. | 2011/0155781 A1 | 6/2011 | Swensgard et al. |
| 2010/0012704 A1 | 1/2010 | Tarinelli Racenet et al. | 2011/0155785 A1 | 6/2011 | Laurent et al. |
| 2010/0032470 A1 | 2/2010 | Hess et al. | 2011/0155787 A1 | 6/2011 | Baxter, III et al. |
| 2010/0057087 A1* | 3/2010 | Cha .................................. 606/80 | 2011/0163147 A1 | 7/2011 | Laurent et al. |
| 2010/0065605 A1 | 3/2010 | Shelton, IV et al. | 2011/0174860 A1 | 7/2011 | Shelton, IV et al. |
| 2010/0069942 A1 | 3/2010 | Shelton, IV | 2011/0174863 A1 | 7/2011 | Shelton, IV et al. |
| 2010/0072254 A1 | 3/2010 | Aranyi et al. | 2011/0192882 A1 | 8/2011 | Hess et al. |
| 2010/0076474 A1 | 3/2010 | Yates et al. | 2011/0226837 A1 | 9/2011 | Baxter, III et al. |
| 2010/0076475 A1 | 3/2010 | Yates et al. | 2011/0233258 A1 | 9/2011 | Boudreaux |
| 2010/0089970 A1 | 4/2010 | Smith et al. | 2011/0253766 A1 | 10/2011 | Baxter, III et al. |
| 2010/0089972 A1 | 4/2010 | Marczyk | 2011/0288573 A1 | 11/2011 | Yates et al. |
| 2010/0108741 A1 | 5/2010 | Hessler et al. | 2011/0290851 A1 | 12/2011 | Shelton, IV |
| 2010/0127042 A1 | 5/2010 | Shelton, IV | 2011/0290853 A1 | 12/2011 | Shelton, IV et al. |
| 2010/0133317 A1 | 6/2010 | Shelton, IV et al. | 2011/0290854 A1 | 12/2011 | Timm et al. |
| 2010/0133318 A1 | 6/2010 | Boudreaux | 2011/0290855 A1 | 12/2011 | Moore et al. |
| 2010/0163598 A1 | 7/2010 | Belzer | 2011/0290856 A1 | 12/2011 | Shelton, IV et al. |
| 2010/0179382 A1 | 7/2010 | Shelton, IV et al. | 2011/0290857 A1 | 12/2011 | Shelton, IV et al. |

| | | | | | | |
|---|---|---|---|---|---|---|
| 2011/0295242 | A1 | 12/2011 | Spivey et al. | EP | 0248844 B1 | 1/1993 |
| 2011/0295269 | A1 | 12/2011 | Swensgard et al. | EP | 0545029 A1 | 6/1993 |
| 2011/0295270 | A1 | 12/2011 | Giordano et al. | EP | 0277959 B1 | 10/1993 |
| 2011/0295295 | A1 | 12/2011 | Shelton, IV et al. | EP | 0233940 B1 | 11/1993 |
| 2012/0024934 | A1 | 2/2012 | Shelton, IV et al. | EP | 0261230 B1 | 11/1993 |
| 2012/0024935 | A1 | 2/2012 | Shelton, IV et al. | EP | 0639349 A2 | 2/1994 |
| 2012/0024936 | A1 | 2/2012 | Baxter, III et al. | EP | 0324636 B1 | 3/1994 |
| 2012/0029272 | A1 | 2/2012 | Shelton, IV et al. | EP | 0593920 A1 | 4/1994 |
| 2012/0029544 | A1 | 2/2012 | Shelton, IV et al. | EP | 0523174 B1 | 6/1994 |
| 2012/0029547 | A1 | 2/2012 | Shelton, IV et al. | EP | 0600182 A2 | 6/1994 |
| 2012/0061448 | A1 | 3/2012 | Zingman | EP | 0310431 B1 | 11/1994 |
| 2012/0071711 | A1 | 3/2012 | Shelton, IV et al. | EP | 0375302 B1 | 11/1994 |
| 2012/0071866 | A1 | 3/2012 | Kerr et al. | EP | 0376562 B1 | 11/1994 |
| 2012/0074196 | A1 | 3/2012 | Shelton, IV et al. | EP | 0630612 A1 | 12/1994 |
| 2012/0074198 | A1 | 3/2012 | Huitema et al. | EP | 0634144 A1 | 1/1995 |
| 2012/0074200 | A1 | 3/2012 | Schmid et al. | EP | 0646356 A2 | 4/1995 |
| 2012/0074201 | A1 | 3/2012 | Baxter, III et al. | EP | 0646357 A1 | 4/1995 |
| 2012/0080332 | A1 | 4/2012 | Shelton, IV et al. | EP | 0653189 A2 | 5/1995 |
| 2012/0080333 | A1 | 4/2012 | Woodard, Jr. et al. | EP | 0669104 A1 | 8/1995 |
| 2012/0080334 | A1 | 4/2012 | Shelton, IV et al. | EP | 0511470 B1 | 10/1995 |
| 2012/0080335 | A1 | 4/2012 | Shelton, IV et al. | EP | 0679367 A2 | 11/1995 |
| 2012/0080336 | A1 | 4/2012 | Shelton, IV et al. | EP | 0392547 B1 | 12/1995 |
| 2012/0080337 | A1 | 4/2012 | Shelton, IV et al. | EP | 0685204 A1 | 12/1995 |
| 2012/0080338 | A1 | 4/2012 | Shelton, IV et al. | EP | 0364216 B1 | 1/1996 |
| 2012/0080339 | A1 | 4/2012 | Shelton, IV et al. | EP | 0699418 A1 | 3/1996 |
| 2012/0080340 | A1 | 4/2012 | Shelton, IV et al. | EP | 0702937 A1 | 3/1996 |
| 2012/0080344 | A1 | 4/2012 | Shelton, IV | EP | 0705571 A1 | 4/1996 |
| 2012/0080345 | A1 | 4/2012 | Morgan et al. | EP | 0711611 A2 | 5/1996 |
| 2012/0080477 | A1 | 4/2012 | Leimbach et al. | EP | 0484677 B2 | 6/1996 |
| 2012/0080478 | A1 | 4/2012 | Morgan et al. | EP | 0541987 B1 | 7/1996 |
| 2012/0080479 | A1 | 4/2012 | Shelton, IV | EP | 0667119 B1 | 7/1996 |
| 2012/0080480 | A1 | 4/2012 | Woodard, Jr. et al. | EP | 0708618 B1 | 3/1997 |
| 2012/0080481 | A1 | 4/2012 | Widenhouse et al. | EP | 0770355 A1 | 5/1997 |
| 2012/0080482 | A1 | 4/2012 | Schall et al. | EP | 0503662 B1 | 6/1997 |
| 2012/0080483 | A1 | 4/2012 | Riestenberg et al. | EP | 0447121 B1 | 7/1997 |
| 2012/0080484 | A1 | 4/2012 | Morgan et al. | EP | 0625077 B1 | 7/1997 |
| 2012/0080485 | A1 | 4/2012 | Woodard, Jr. et al. | EP | 0633749 B1 | 8/1997 |
| 2012/0080486 | A1 | 4/2012 | Woodard, Jr. et al. | EP | 0710090 B1 | 8/1997 |
| 2012/0080487 | A1 | 4/2012 | Woodard, Jr. et al. | EP | 0578425 B1 | 9/1997 |
| 2012/0080488 | A1 | 4/2012 | Shelton, IV et al. | EP | 0625335 B1 | 11/1997 |
| 2012/0080489 | A1 | 4/2012 | Shelton, IV et al. | EP | 0552423 B1 | 1/1998 |
| 2012/0080490 | A1 | 4/2012 | Shelton, IV et al. | EP | 0592244 B1 | 1/1998 |
| 2012/0080491 | A1 | 4/2012 | Shelton, IV et al. | EP | 0648476 B1 | 1/1998 |
| 2012/0080493 | A1 | 4/2012 | Shelton, IV et al. | EP | 0649290 B1 | 3/1998 |
| 2012/0080496 | A1 | 4/2012 | Schall et al. | EP | 0598618 B1 | 9/1998 |
| 2012/0080498 | A1 | 4/2012 | Shelton, IV et al. | EP | 0676173 B1 | 9/1998 |
| 2012/0080499 | A1 | 4/2012 | Schall et al. | EP | 0678007 B1 | 9/1998 |
| 2012/0080500 | A1 | 4/2012 | Morgan et al. | EP | 0603472 B1 | 11/1998 |
| 2012/0080501 | A1 | 4/2012 | Morgan et al. | EP | 0605351 B1 | 11/1998 |
| 2012/0080502 | A1 | 4/2012 | Morgan et al. | EP | 0878169 A1 | 11/1998 |
| 2012/0080503 | A1 | 4/2012 | Woodard, Jr. et al. | EP | 0879742 A1 | 11/1998 |
| 2012/0083833 | A1 | 4/2012 | Shelton, IV et al. | EP | 0695144 B1 | 12/1998 |
| 2012/0083834 | A1 | 4/2012 | Shelton, IV et al. | EP | 0722296 B1 | 12/1998 |
| 2012/0083835 | A1 | 4/2012 | Shelton, IV et al. | EP | 0760230 B1 | 2/1999 |
| 2012/0083836 | A1 | 4/2012 | Shelton, IV et al. | EP | 0623316 B1 | 3/1999 |
| | | | | EP | 0650701 B1 | 3/1999 |
| FOREIGN PATENT DOCUMENTS | | | | EP | 0537572 B1 | 6/1999 |
| CA | | 2514274 A1 | 1/2006 | EP | 0923907 A1 | 6/1999 |
| CN | | 1868411 A | 11/2006 | EP | 0843906 B1 | 3/2000 |
| CN | | 1915180 A | 2/2007 | EP | 0552050 B1 | 5/2000 |
| DE | | 273689 C | 5/1914 | EP | 0833592 81 | 5/2000 |
| DE | | 1775926 A | 1/1972 | EP | 0830094 B1 | 9/2000 |
| DE | | 3036217 A1 | 4/1982 | EP | 1034747 A1 | 9/2000 |
| DE | | 9412228 U | 9/1994 | EP | 1034748 A1 | 9/2000 |
| DE | | 19509116 A1 | 9/1996 | EP | 0694290 B1 | 11/2000 |
| DE | | 19851291 A1 | 1/2000 | EP | 1050278 A1 | 11/2000 |
| DE | | 19924311 A1 | 11/2000 | EP | 1053719 A1 | 11/2000 |
| DE | | 69328576 T2 | 1/2001 | EP | 1053720 A1 | 11/2000 |
| DE | | 10052679 A1 | 5/2001 | EP | 1055399 A1 | 11/2000 |
| DE | | 20112837 U1 | 10/2001 | EP | 1055400 A1 | 11/2000 |
| DE | | 20121753 U1 | 4/2003 | EP | 1080694 A1 | 3/2001 |
| DE | | 10314072 A1 | 10/2004 | EP | 1090592 A1 | 4/2001 |
| DE | | 3210466 A1 | 6/2007 | EP | 1095627 A1 | 5/2001 |
| DE | | 202007003114 U1 | 6/2007 | EP | 1256318 B1 | 5/2001 |
| EP | | 0122046 A1 | 10/1984 | EP | 0806914 B1 | 9/2001 |
| EP | | 0070230 B1 | 10/1985 | EP | 0768840 B1 | 12/2001 |
| EP | | 0387980 B1 | 10/1985 | EP | 0908152 B1 | 1/2002 |
| EP | | 0033548 B1 | 5/1986 | EP | 0872213 B1 | 5/2002 |
| EP | | 0276104 A2 | 7/1988 | EP | 0862386 B1 | 6/2002 |

| | | | | | | | |
|---|---|---|---|---|---|---|---|
| EP | 0949886 | B1 | 9/2002 | EP | 1484024 | B1 | 1/2007 |
| EP | 1238634 | A2 | 9/2002 | EP | 1754445 | A2 | 2/2007 |
| EP | 0858295 | B1 | 12/2002 | EP | 1759812 | A1 | 3/2007 |
| EP | 0656188 | B1 | 1/2003 | EP | 1767163 | A1 | 3/2007 |
| EP | 1284120 | A1 | 2/2003 | EP | 1769756 | A1 | 4/2007 |
| EP | 1287788 | A1 | 3/2003 | EP | 1769758 | A1 | 4/2007 |
| EP | 0717966 | B1 | 4/2003 | EP | 1581128 | B1 | 5/2007 |
| EP | 0869742 | B1 | 5/2003 | EP | 1785097 | A2 | 5/2007 |
| EP | 0829235 | B1 | 6/2003 | EP | 1790293 | A2 | 5/2007 |
| EP | 0887046 | B1 | 7/2003 | EP | 1800610 | A1 | 6/2007 |
| EP | 0852480 | B1 | 8/2003 | EP | 1300117 | B1 | 8/2007 |
| EP | 0891154 | B1 | 9/2003 | EP | 1813199 | A1 | 8/2007 |
| EP | 0813843 | B1 | 10/2003 | EP | 1813201 | A1 | 8/2007 |
| EP | 0873089 | B1 | 10/2003 | EP | 1813203 | A2 | 8/2007 |
| EP | 0856326 | B1 | 11/2003 | EP | 1813207 | A1 | 8/2007 |
| EP | 1374788 | A1 | 1/2004 | EP | 1813209 | A1 | 8/2007 |
| EP | 0741996 | B1 | 2/2004 | EP | 1487359 | B1 | 10/2007 |
| EP | 0814712 | B1 | 2/2004 | EP | 1599146 | B1 | 10/2007 |
| EP | 1402837 | A1 | 3/2004 | EP | 1839596 | A1 | 10/2007 |
| EP | 0705570 | B1 | 4/2004 | EP | 1402821 | B1 | 12/2007 |
| EP | 0959784 | B1 | 4/2004 | EP | 1872727 | A1 | 1/2008 |
| EP | 1407719 | A2 | 4/2004 | EP | 1897502 | A1 | 3/2008 |
| EP | 1086713 | B1 | 5/2004 | EP | 1330201 | B1 | 6/2008 |
| EP | 0996378 | B1 | 6/2004 | EP | 1702568 | B1 | 7/2008 |
| EP | 1426012 | A1 | 6/2004 | EP | 1943957 | A2 | 7/2008 |
| EP | 0833593 | B2 | 7/2004 | EP | 1943976 | A2 | 7/2008 |
| EP | 1442694 | A1 | 8/2004 | EP | 1593337 | B1 | 8/2008 |
| EP | 0888749 | B1 | 9/2004 | EP | 1970014 | A1 | 9/2008 |
| EP | 0959786 | B1 | 9/2004 | EP | 1980213 | A2 | 10/2008 |
| EP | 1459695 | A1 | 9/2004 | EP | 1759645 | B1 | 11/2008 |
| EP | 1473819 | A1 | 11/2004 | EP | 1990014 | A2 | 11/2008 |
| EP | 1477119 | A1 | 11/2004 | EP | 1693008 | B1 | 12/2008 |
| EP | 1479345 | A1 | 11/2004 | EP | 1759640 | B1 | 12/2008 |
| EP | 1479347 | A1 | 11/2004 | EP | 2000102 | A2 | 12/2008 |
| EP | 1479348 | A1 | 11/2004 | EP | 1736104 | B1 | 3/2009 |
| EP | 0754437 | B2 | 12/2004 | EP | 1749486 | B1 | 3/2009 |
| EP | 1025807 | B1 | 12/2004 | EP | 1721576 | B1 | 4/2009 |
| EP | 1001710 | B1 | 1/2005 | EP | 1733686 | B1 | 4/2009 |
| EP | 1520521 | A1 | 4/2005 | EP | 2044890 | A1 | 4/2009 |
| EP | 1520523 | A1 | 4/2005 | EP | 1745748 | B1 | 8/2009 |
| EP | 1520525 | A1 | 4/2005 | EP | 2090256 | A2 | 8/2009 |
| EP | 1522264 | A1 | 4/2005 | EP | 1813208 | B1 | 11/2009 |
| EP | 1523942 | A2 | 4/2005 | EP | 1607050 | B1 | 12/2009 |
| EP | 1550408 | A1 | 7/2005 | EP | 1566150 | B1 | 4/2010 |
| EP | 1557129 | A1 | 7/2005 | EP | 1813206 | B1 | 4/2010 |
| EP | 1064883 | B1 | 8/2005 | EP | 1769754 | B1 | 6/2010 |
| EP | 1067876 | B1 | 8/2005 | EP | 1535565 | B1 | 10/2010 |
| EP | 0870473 | B1 | 9/2005 | EP | 1702570 | B1 | 10/2010 |
| EP | 1157666 | B1 | 9/2005 | EP | 1785098 | B1 | 10/2010 |
| EP | 0880338 | B1 | 10/2005 | EP | 1813205 | B1 | 6/2011 |
| EP | 1158917 | B1 | 11/2005 | FR | 999646 | A | 2/1952 |
| EP | 1344498 | B1 | 11/2005 | FR | 1112936 | A | 3/1956 |
| EP | 1330989 | B1 | 12/2005 | FR | 2765794 | A | 1/1999 |
| EP | 0771176 | B2 | 1/2006 | GB | 939929 | A | 10/1963 |
| EP | 1621138 | A2 | 2/2006 | GB | 1210522 | A | 10/1970 |
| EP | 1621139 | A2 | 2/2006 | GB | 1217159 | A | 12/1970 |
| EP | 1621141 | A2 | 2/2006 | GB | 1339394 | A | 12/1973 |
| EP | 1621145 | A2 | 2/2006 | GB | 2109241 | A | 6/1983 |
| EP | 1621151 | A2 | 2/2006 | GB | 2272159 | A | 5/1994 |
| EP | 1034746 | B1 | 3/2006 | GB | 2284242 | A | 5/1995 |
| EP | 1632191 | A2 | 3/2006 | GB | 2336214 | A | 10/1999 |
| EP | 1065981 | B1 | 5/2006 | GB | 2425903 | A | 11/2006 |
| EP | 1082944 | B1 | 5/2006 | JP | 6007357 | A | 1/1994 |
| EP | 1652481 | A2 | 5/2006 | JP | 7051273 | A | 2/1995 |
| EP | 1382303 | B1 | 6/2006 | JP | 8033641 | A | 2/1996 |
| EP | 1253866 | B1 | 7/2006 | JP | 8229050 | A | 9/1996 |
| EP | 1032318 | B1 | 8/2006 | JP | 2000033071 | A | 2/2000 |
| EP | 1045672 | B1 | 8/2006 | JP | 2000171730 | A | 6/2000 |
| EP | 1617768 | B1 | 8/2006 | JP | 2000287987 | A | 10/2000 |
| EP | 1693015 | A2 | 8/2006 | JP | 2000325303 | A | 11/2000 |
| EP | 1400214 | B1 | 9/2006 | JP | 2001286477 | A | 10/2001 |
| EP | 1702567 | A2 | 9/2006 | JP | 2002143078 | A | 5/2002 |
| EP | 1129665 | B1 | 11/2006 | JP | 2002369820 | A | 12/2002 |
| EP | 1400206 | B1 | 11/2006 | JP | 2005505322 | T | 2/2005 |
| EP | 1721568 | A1 | 11/2006 | JP | 2005103293 | A | 4/2005 |
| EP | 1256317 | B1 | 12/2006 | JP | 2005131163 | A | 5/2005 |
| EP | 1728473 | A1 | 12/2006 | JP | 2005131164 | A | 5/2005 |
| EP | 1728475 | A2 | 12/2006 | JP | 2005131173 | A | 5/2005 |
| EP | 1479346 | B1 | 1/2007 | JP | 2005131211 | A | 5/2005 |

| | | | | | | |
|---|---|---|---|---|---|---|
| JP | 2005131212 | A | 5/2005 | WO | WO 98/47436 A1 | 10/1998 |
| JP | 2005137423 | A | 6/2005 | WO | WO 99/03407 A1 | 1/1999 |
| JP | 2005152416 | A | 6/2005 | WO | WO 99/03408 A1 | 1/1999 |
| JP | 2006-281405 | A | 10/2006 | WO | WO 99/03409 A1 | 1/1999 |
| RU | 2008830 | C1 | 3/1994 | WO | WO 99/12483 A1 | 3/1999 |
| RU | 2187249 | C2 | 8/2002 | WO | WO 99/12487 A1 | 3/1999 |
| RU | 2225170 | C2 | 3/2004 | WO | WO 99/12488 A1 | 3/1999 |
| SU | 189517 | A | 1/1967 | WO | WO 99/15086 A1 | 4/1999 |
| SU | 328636 | A | 9/1972 | WO | WO 99/15091 A1 | 4/1999 |
| SU | 886900 | A1 | 12/1981 | WO | WO 99/23933 A2 | 5/1999 |
| SU | 1009439 | A | 4/1983 | WO | WO 99/23959 A1 | 5/1999 |
| SU | 1333319 | A2 | 8/1987 | WO | WO 99/25261 A1 | 5/1999 |
| SU | 1377053 | A1 | 2/1988 | WO | WO 99/29244 A1 | 6/1999 |
| SU | 1561964 | A1 | 5/1990 | WO | WO 99/34744 A1 | 7/1999 |
| SU | 1722476 | A1 | 3/1992 | WO | WO 99/45849 A1 | 9/1999 |
| WO | WO 91/15157 A1 | | 10/1991 | WO | WO 99/48430 A1 | 9/1999 |
| WO | WO 92/20295 A1 | | 11/1992 | WO | WO 99/51158 A1 | 10/1999 |
| WO | WO 92/21300 A1 | | 12/1992 | WO | WO 00/24322 A1 | 5/2000 |
| WO | WO 93/08755 A1 | | 5/1993 | WO | WO 00/24330 A1 | 5/2000 |
| WO | WO 93/13718 A1 | | 7/1993 | WO | WO 00/41638 A1 | 7/2000 |
| WO | WO 93/14690 A1 | | 8/1993 | WO | WO 00/48506 A1 | 8/2000 |
| WO | WO 93/15648 A1 | | 8/1993 | WO | WO 00/53112 A2 | 9/2000 |
| WO | WO 93/15850 A1 | | 8/1993 | WO | WO 00/54653 A1 | 9/2000 |
| WO | WO 93/19681 A1 | | 10/1993 | WO | WO 00/64365 A1 | 11/2000 |
| WO | WO 94/00060 A1 | | 1/1994 | WO | WO 00/72762 A1 | 12/2000 |
| WO | WO 94/11057 A1 | | 5/1994 | WO | WO 00/72765 A1 | 12/2000 |
| WO | WO 94/12108 A1 | | 6/1994 | WO | WO 01/03587 A1 | 1/2001 |
| WO | WO 94/18893 A1 | | 9/1994 | WO | WO 01/05702 A1 | 1/2001 |
| WO | WO 94/22378 A1 | | 10/1994 | WO | WO 01/10482 A1 | 2/2001 |
| WO | WO 94/23659 A1 | | 10/1994 | WO | WO 01/35845 A1 | 5/2001 |
| WO | WO 95/02369 A1 | | 1/1995 | WO | WO 01/54594 A1 | 8/2001 |
| WO | WO 95/03743 A1 | | 2/1995 | WO | WO 01/58371 A1 | 8/2001 |
| WO | WO 95/06817 A1 | | 3/1995 | WO | WO 01/62158 A2 | 8/2001 |
| WO | WO 95/09576 A1 | | 4/1995 | WO | WO 01/62161 A1 | 8/2001 |
| WO | WO 95/09577 A1 | | 4/1995 | WO | WO 01/62162 A1 | 8/2001 |
| WO | WO 95/14436 A1 | | 6/1995 | WO | WO 01/62164 A2 | 8/2001 |
| WO | WO 95/17855 A1 | | 7/1995 | WO | WO 01/62169 A2 | 8/2001 |
| WO | WO 95/18383 A1 | | 7/1995 | WO | WO 01/78605 A2 | 10/2001 |
| WO | WO 95/18572 A1 | | 7/1995 | WO | WO 01/91646 A1 | 12/2001 |
| WO | WO 95/19739 A1 | | 7/1995 | WO | WO 02/07608 A2 | 1/2002 |
| WO | WO 95/20360 A1 | | 8/1995 | WO | WO 02/07618 A1 | 1/2002 |
| WO | WO 95/23557 A1 | | 9/1995 | WO | WO 02/17799 A1 | 3/2002 |
| WO | WO 95/24865 A1 | | 9/1995 | WO | WO 02/19920 A1 | 3/2002 |
| WO | WO 95/25471 A3 | | 9/1995 | WO | WO 02/19932 A1 | 3/2002 |
| WO | WO 95/26562 A1 | | 10/1995 | WO | WO 02/30297 A2 | 4/2002 |
| WO | WO 95/29639 A1 | | 11/1995 | WO | WO 02/32322 A2 | 4/2002 |
| WO | WO 96/04858 A1 | | 2/1996 | WO | WO 02/36028 A1 | 5/2002 |
| WO | WO 96/19151 A1 | | 6/1996 | WO | WO 02/43571 A2 | 6/2002 |
| WO | WO 96/19152 A1 | | 6/1996 | WO | WO 02/058568 A1 | 8/2002 |
| WO | WO 96/20652 A1 | | 7/1996 | WO | WO 02/060328 A1 | 8/2002 |
| WO | WO 96/21119 A1 | | 7/1996 | WO | WO 02/067785 A2 | 9/2002 |
| WO | WO 96/22055 A1 | | 7/1996 | WO | WO 02/098302 A1 | 12/2002 |
| WO | WO 96/23448 A1 | | 8/1996 | WO | WO 03/000138 A1 | 1/2003 |
| WO | WO 96/24301 A1 | | 8/1996 | WO | WO 03/001329 A2 | 1/2003 |
| WO | WO 96/27337 A1 | | 9/1996 | WO | WO 03/013363 A1 | 2/2003 |
| WO | WO 96/31155 A1 | | 10/1996 | WO | WO 03/015604 A2 | 2/2003 |
| WO | WO 96/35464 A1 | | 11/1996 | WO | WO 03/020106 A2 | 3/2003 |
| WO | WO 96/39085 A1 | | 12/1996 | WO | WO 03/020139 A2 | 3/2003 |
| WO | WO 96/39086 A1 | | 12/1996 | WO | WO 03/024339 A1 | 3/2003 |
| WO | WO 96/39087 A1 | | 12/1996 | WO | WO 03/079909 A3 | 3/2003 |
| WO | WO 96/39088 A1 | | 12/1996 | WO | WO 03/030743 A2 | 4/2003 |
| WO | WO 96/39089 A1 | | 12/1996 | WO | WO 03/037193 A1 | 5/2003 |
| WO | WO 97/00646 A1 | | 1/1997 | WO | WO 03/047436 A3 | 6/2003 |
| WO | WO 97/00647 A1 | | 1/1997 | WO | WO 03/055402 A1 | 7/2003 |
| WO | WO 97/06582 A1 | | 2/1997 | WO | WO 03/057048 A1 | 7/2003 |
| WO | WO 97/10763 A1 | | 3/1997 | WO | WO 03/057058 A1 | 7/2003 |
| WO | WO 97/10764 A1 | | 3/1997 | WO | WO 03/063694 A1 | 8/2003 |
| WO | WO 97/11648 A2 | | 4/1997 | WO | WO 03/077769 A1 | 9/2003 |
| WO | WO 97/11649 A1 | | 4/1997 | WO | WO 03/079911 A1 | 10/2003 |
| WO | WO 97/15237 A1 | | 5/1997 | WO | WO 03/082126 A1 | 10/2003 |
| WO | WO 97/24073 A1 | | 7/1997 | WO | WO 03/088845 A2 | 10/2003 |
| WO | WO 97/24993 A1 | | 7/1997 | WO | WO 03/090630 A1 | 11/2003 |
| WO | WO 97/30644 A1 | | 8/1997 | WO | WO 03/094743 A1 | 11/2003 |
| WO | WO 97/34533 A1 | | 9/1997 | WO | WO 03/094745 A1 | 11/2003 |
| WO | WO 97/37598 A1 | | 10/1997 | WO | WO 03/094746 A1 | 11/2003 |
| WO | WO 97/39688 A2 | | 10/1997 | WO | WO 03/094747 A1 | 11/2003 |
| WO | WO 98/17180 A1 | | 4/1998 | WO | WO 03/101313 A1 | 12/2003 |
| WO | WO 98/27880 A1 | | 7/1998 | WO | WO 03/105698 A2 | 12/2003 |
| WO | WO 98/30153 A1 | | 7/1998 | WO | WO 03/105702 A2 | 12/2003 |

| | | |
|---|---|---|
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 00/57796 A1 | 10/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

U.S. Appl. No. 12/366,538, filed Feb. 5, 2009.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
International Search Report for PCT/US2010/022328, dated May 21, 2010, included on the PCT Publication WO 2010/090934 (110 pages).

* cited by examiner

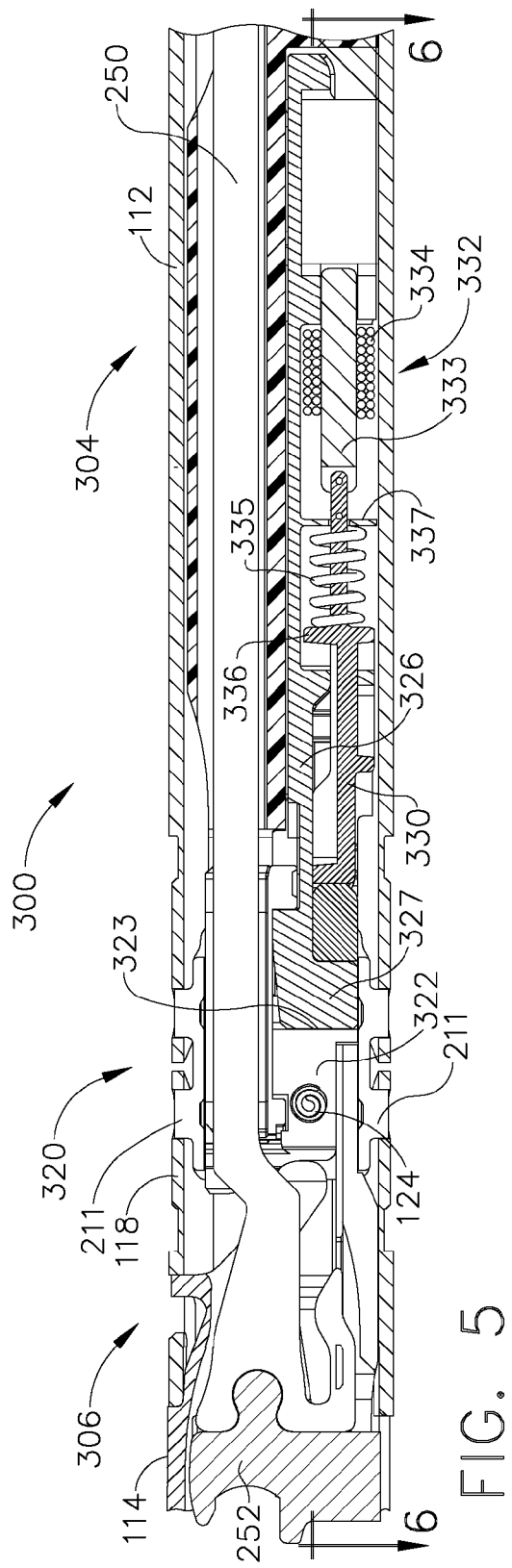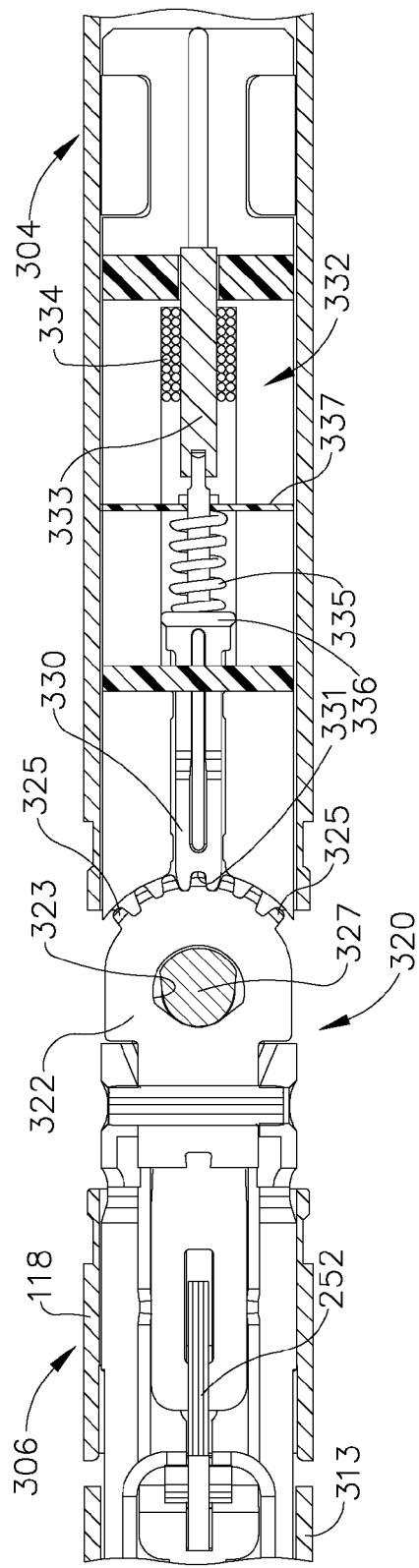
FIG. 5
FIG. 6

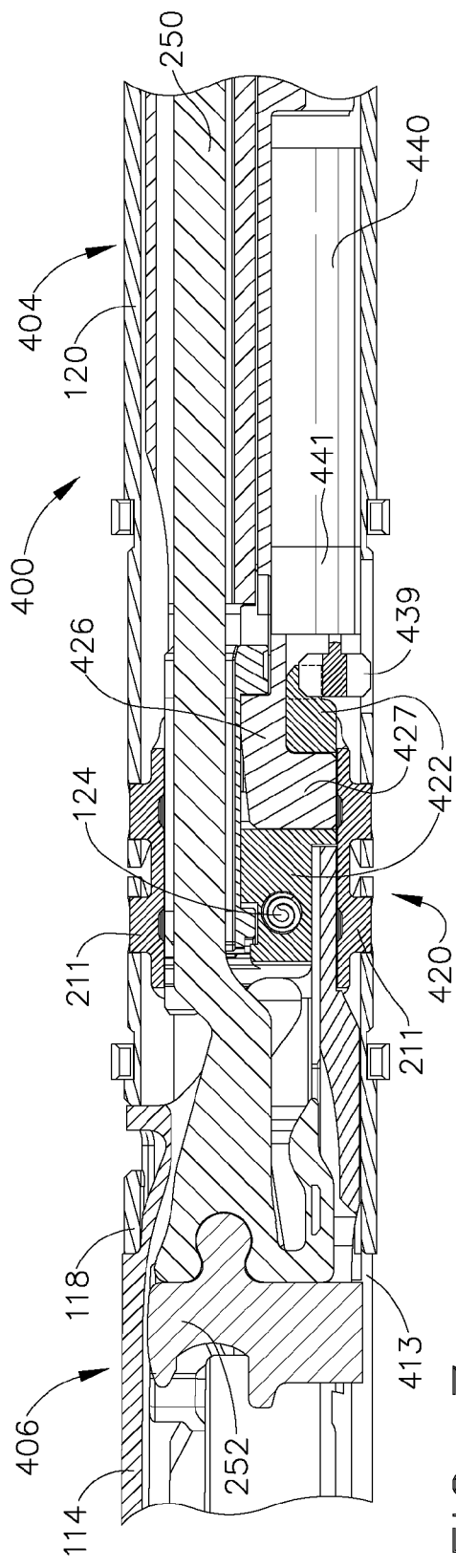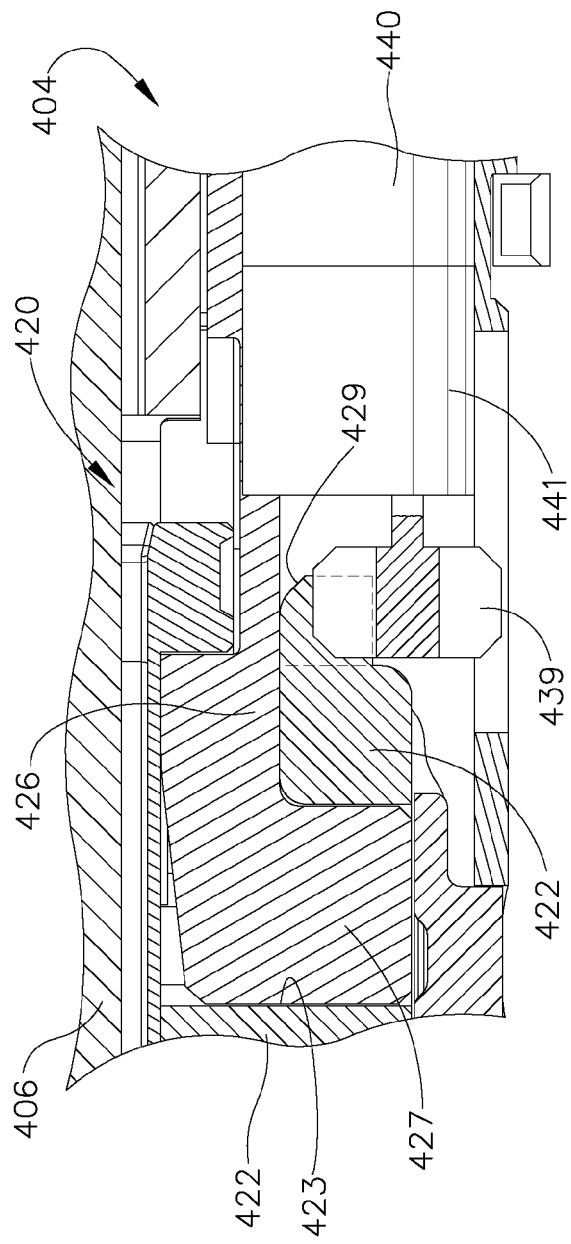
FIG. 7
FIG. 8

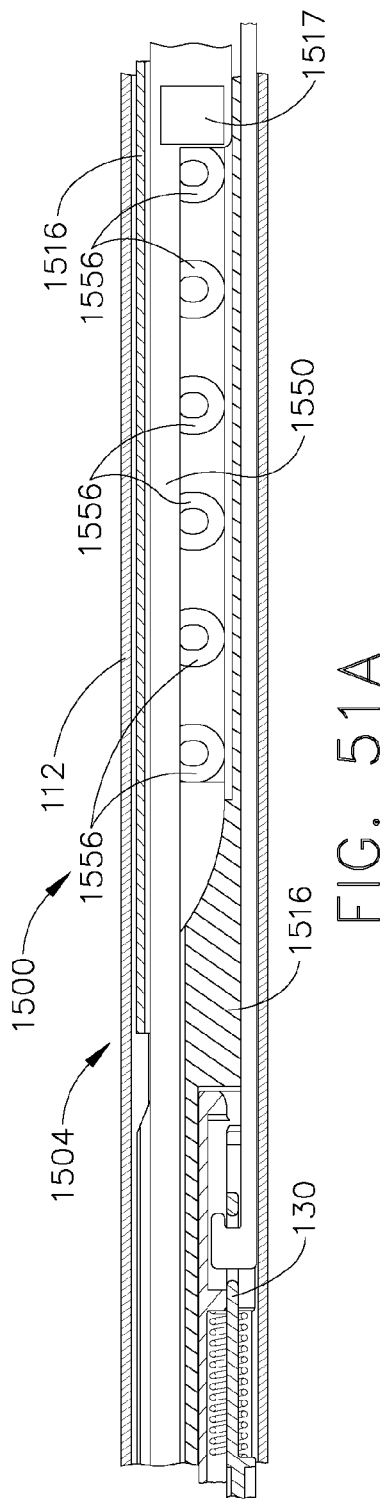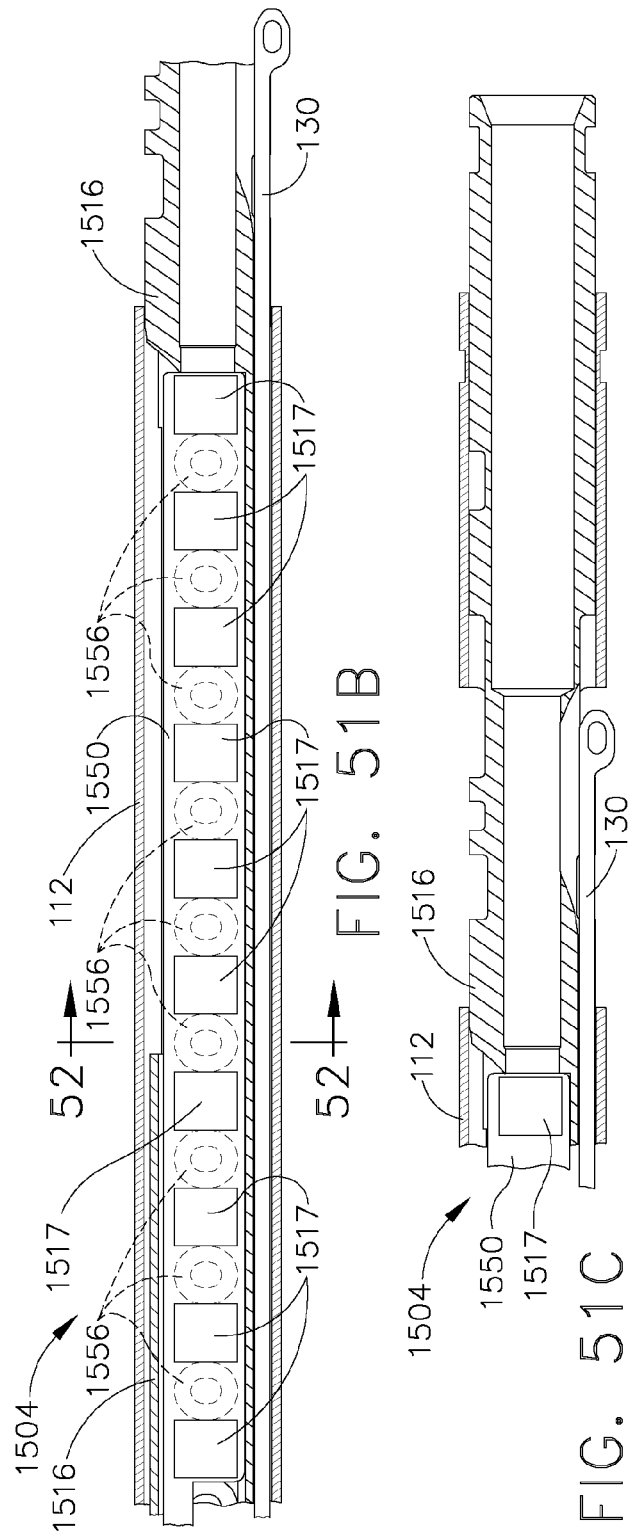

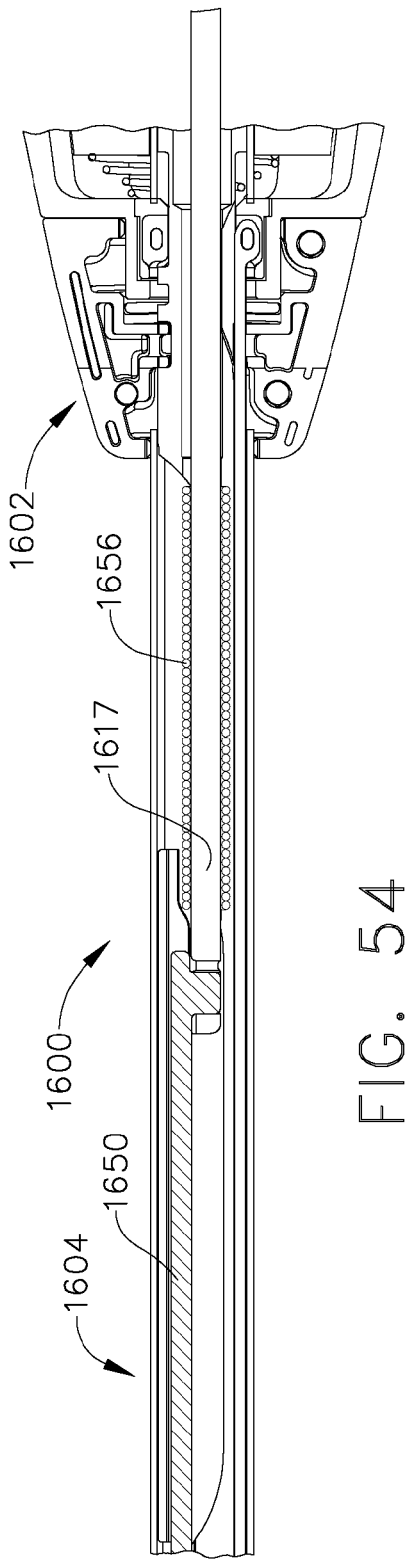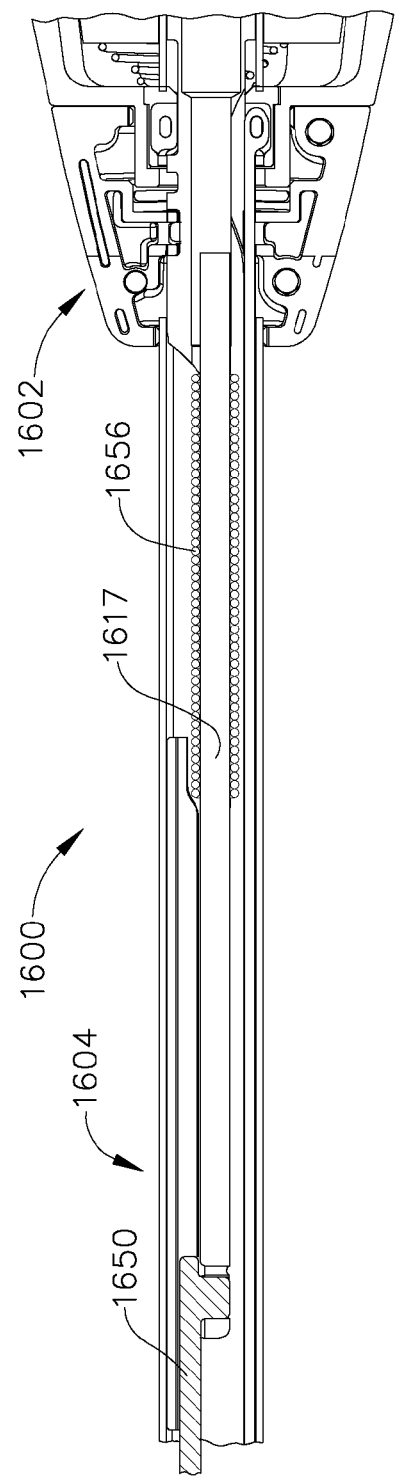

SURGICAL STAPLING INSTRUMENT COMPRISING AN ARTICULATION JOINT

BACKGROUND i. Technical Field

The present invention relates, in general, to surgical instruments and, more particularly, to surgical stapling instruments.

ii. Background of the Related Art

Surgical stapling instruments have been used to simultaneously make an incision in tissue and apply lines of staples on opposing sides of the incision. Such instruments commonly include a pair of cooperating jaw members that, if the instrument is intended for endoscopic or laparoscopic applications, are capable of passing through a cannula passageway. In various embodiments, one of the jaw members can receive a staple cartridge having at least two laterally spaced rows of staples. The other jaw member can define an anvil having staple-forming pockets aligned with the rows of staples in the cartridge. The instrument can further include a plurality of wedges, or a staple sled, which, when driven distally, passes through openings in the staple cartridge and engages drivers supporting the staples in order to effect the firing of the staples toward the anvil. The simultaneous severing of tissue while forming rows of staples on each side of the cut can reduce bleeding and simplify various surgical procedures. In certain circumstances, however, the force required to form the staples and incise the tissue simultaneously may be significant.

Previous surgical stapling instruments have included a handle assembly, an elongate shaft extending from the handle assembly, and an end effector movably mounted to the elongate shaft, wherein the end effector can be articulated relative to the elongate shaft. Often, a surgeon is required to use both hands in order to articulate the end effector relative to the shaft, i.e., the surgeon is often required to use one hand to hold the handle assembly of the surgical instrument, for example, and use their other hand to operate a lever, for example, which articulates the end effector. While such surgical instruments can be suitable in many circumstances, a surgeon may not have a hand free to perform another step in the surgical procedure. The foregoing discussion is intended only to illustrate some of the shortcomings present in the field of the invention at the time, and should not be taken as a disavowal of claim scope.

SUMMARY

In one general aspect, a surgical instrument can comprise a plurality of magnetic elements configured to articulate an end effector of the surgical instrument. The surgical instrument can comprise at least one electromagnet which can be selectively activated, or polarized, to generate a magnetic field sufficient to motivate at least one second magnetic element, such as a permanent magnet and/or an iron core, for example, mounted to the end effector. In various embodiments, a surgical instrument can comprise a first electromagnet configured to generate a first magnetic field which rotates an end effector in a first direction and, in addition, a second electromagnet configured to generate a second magnetic field which rotates the end effector in a second direction. In certain embodiments, a surgical instrument can comprise at least one solenoid which can be configured to pivot an end effector of the surgical instrument.

In one general aspect, a surgical instrument can comprise a motor which can be configured to pivot an end effector of the surgical instrument. In certain embodiments, the motor can comprise windings which can be selectively energized to rotate an iron core. In at least one embodiment, the motor can comprise at least one electromagnet which can be configured to rotate a shaft having at least one magnetic element mounted thereto. In various embodiments, a surgical instrument can further comprise a lock and/or brake which can be configured to prevent, or at least inhibit, the articulation of the end effector of the surgical instrument. In certain embodiments, a lock can comprise at least one solenoid, motor, and/or electromagnet which can be configured to move a locking element between locked and unlocked positions in order to engage and disengage the locking element with the end effector.

In one general aspect, a surgical instrument can comprise a plurality of magnetic elements configured to open and close an end effector of the surgical instrument. In certain embodiments, the surgical instrument can comprise at least one electromagnet which can be selectively activated, or polarized, to generate a magnetic field sufficient to motivate at least one second magnetic element, such as a permanent magnet and/or an iron core, for example, mounted to an anvil of the end effector. In another general aspect, a surgical stapling instrument can comprise a plurality of magnetic elements configured to advance and/or retract a firing bar, cutting member, and/or staple sled within the surgical instrument in order to incise and/or staple tissue positioned within an end effector of the surgical instrument. In certain embodiments, the cutting element can comprise at least one electromagnet mounted thereto which can be configured to generate a magnetic field configured to interact with one or more permanent magnets, for example, mounted to the end effector.

This Summary is intended to briefly outline certain embodiments of the subject application. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5 is a side cross-sectional view of an articulation joint connecting an end effector and an elongate shaft of a surgical instrument in accordance with at least one embodiment of the present invention;

FIG. 6 is a bottom cross-sectional view of the surgical instrument of FIG. 5 taken along line 6-6 in FIG. 5 illustrating a solenoid-driven articulation lock;

FIG. 7 is a cross-sectional view of an articulation joint connecting an end effector and an elongate shaft of a surgical instrument in accordance with at least one embodiment of the present invention;

FIG. 8 is a detail view of the articulation joint of FIG. 7 illustrating a motor configured to articulate the end effector;

FIGS. 51A-51C illustrate distal, middle, and proximal portions of an elongate shaft of a surgical instrument and a movable firing bar positioned within the elongate shaft in accordance with at least one embodiment of the present invention;

FIG. 51A is a cross-sectional view of the distal portion of the elongate shaft and the movable firing bar illustrating an array of electromagnets positioned within the elongate shaft;

FIG. 51B is a cross-sectional view of the middle portion of the elongate shaft and the movable firing bar of FIG. 51A illustrating permanent magnets mounted to the firing bar and electromagnets positioned within the shaft;

FIG. 51C is a cross-sectional view of the proximal portion of the elongate shaft and the movable firing bar of FIG. 51A;

FIG. 54 is a cross-sectional view of an elongate shaft of a surgical instrument according to at least one embodiment of the present invention illustrating a firing bar in an unfired position; and FIG. 55 is a cross-sectional view of the surgical instrument of FIG. 54 illustrating the firing bar moved into a fired position by an electromagnetic coil.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The disclosures of the following commonly-owned, contemporaneously-filed United States Patent Applications are incorporated herein by reference in their entirety:
(1) U.S. patent application Ser. No. 12/366,539, entitled SURGICAL STAPLING INSTRUMENT; and
(2) U.S. patent application Ser. No. 12/366,538, entitled SURGICAL STAPLING INSTRUMENT COMPRISING A MAGNETIC ELEMENT DRIVER.

Figure 1A:
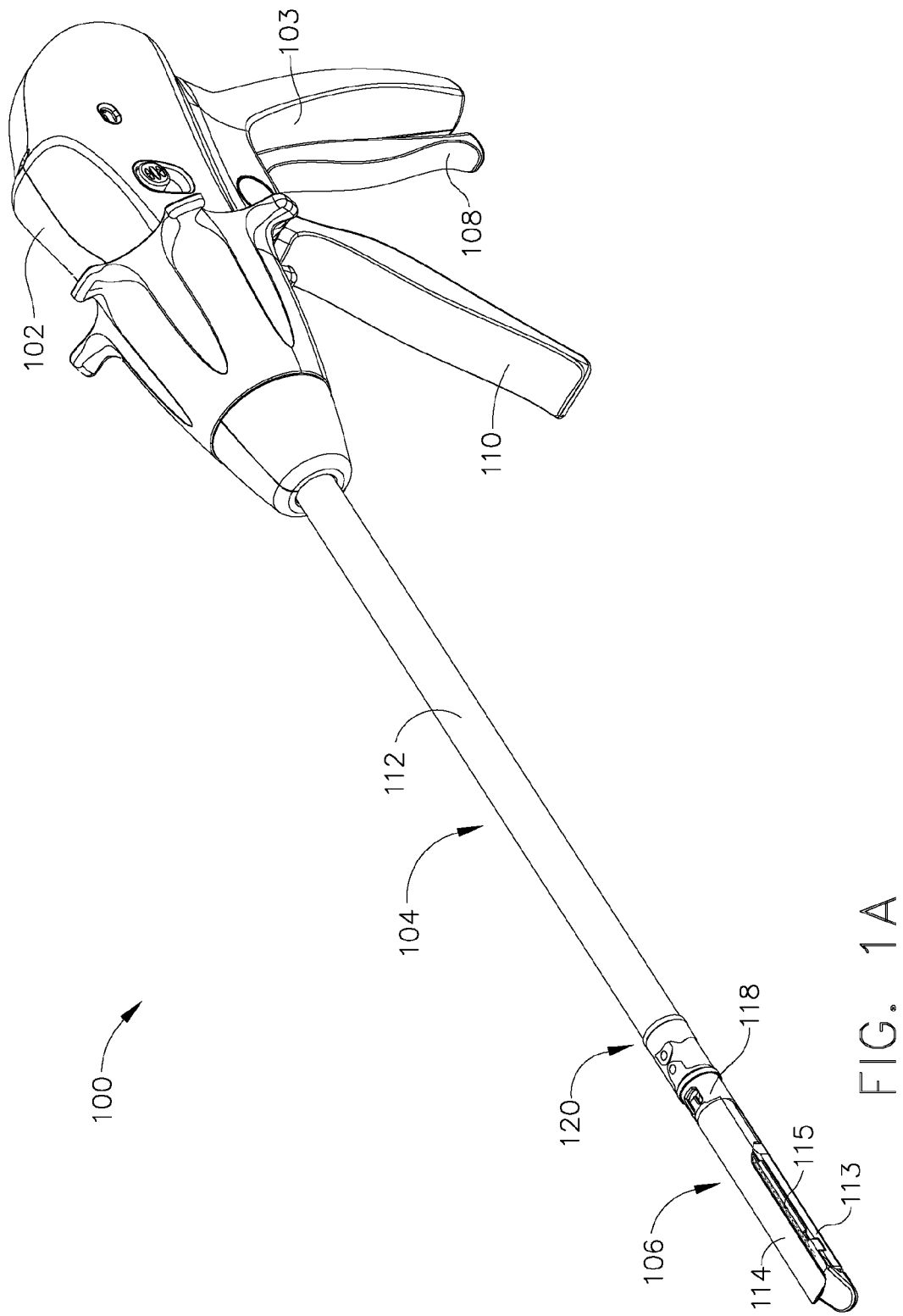
FIG. 1A is a perspective view of a surgical stapling instrument comprising a handle assembly, an elongate shaft extending from the handle assembly, and an articulatable end effector extending from the elongate shaft.
Figure 1B:
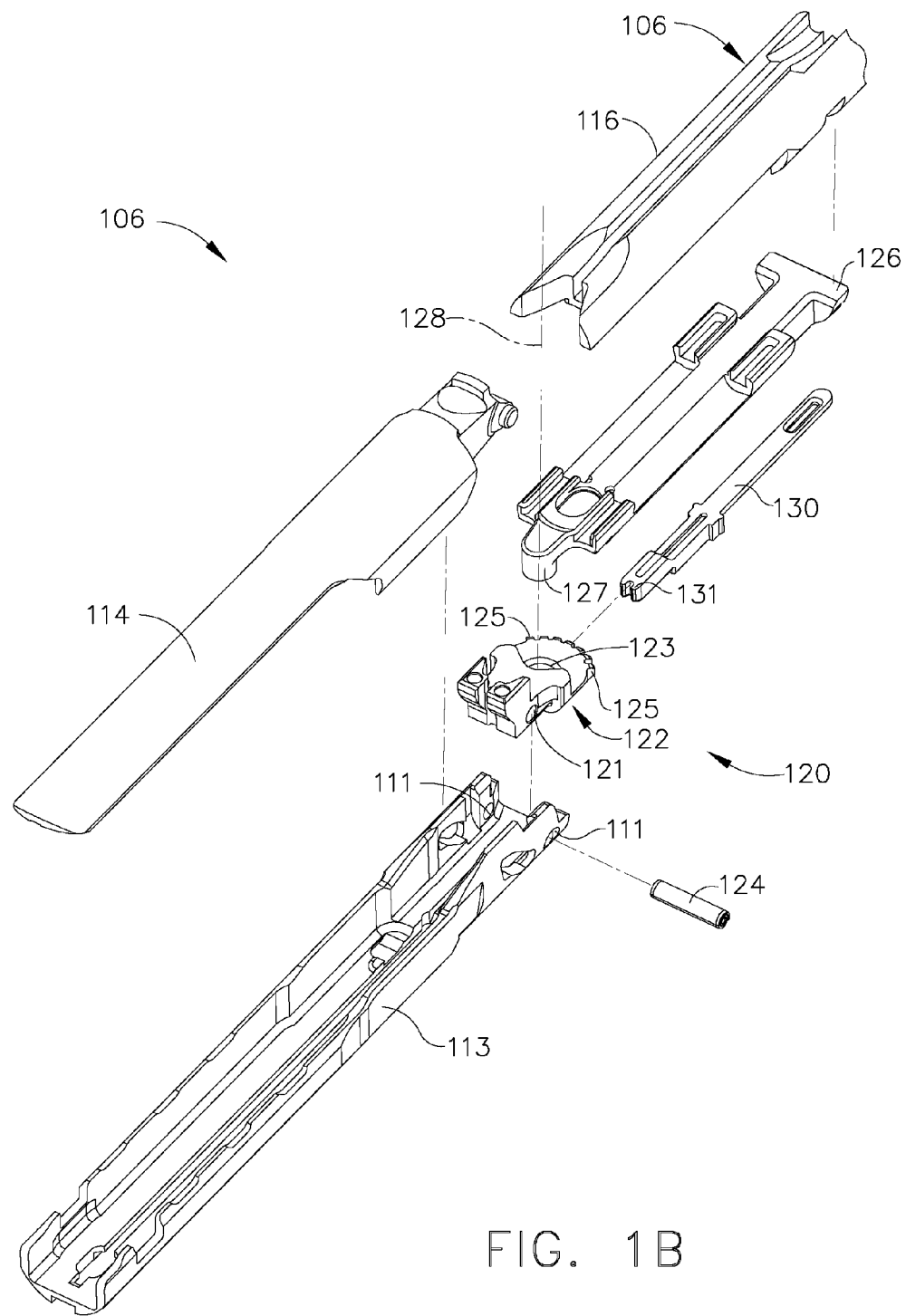
FIG. 1B is an exploded view of the end effector of the surgical instrument of FIG. 1.

In various embodiments, referring to FIGS. 1A and 1B, a surgical instrument, such as surgical instrument 100, for example, can comprise a handle assembly 102, an elongate shaft 104 extending from handle assembly 102, and an end effector 106 which can be moved, or articulated, relative to elongate shaft 104 as described in greater detail further below. In at least one embodiment, handle assembly 102 can comprise a closure trigger 108 which can be configured to open and close end effector 106. More particularly, end effector 106 can comprise anvil 114 and, in addition, elongate shaft 104 can comprise closure tube 112 wherein the actuation of closure trigger 108 can displace closure tube 112 longitudinally in order to rotate anvil 114 between opened and closed positions relative to staple cartridge channel 113 and staple cartridge 115. In at least one embodiment, closure tube 112 can be configured to slide relative to a stationary portion of elongate shaft 104, such as spine 116 (FIG. 1B), for example. In certain embodiments, end effector 106 can further comprise a tube portion, such as distal tube portion 118, for example, which can be displaced by closure tube 112 in order open and/or close anvil 114. In at least one embodiment, surgical instrument 100 can further comprise one or more pivot links 211 (FIGS. 2 and 3) which can be configured to connect closure tube 112 to distal tube portion 118 and permit distal tube portion 118 to articulate relative to closure tube 112 when end effector 106 articulates relative to elongate shaft 104. In any event, once anvil 114 has been closed, firing trigger 110 of handle assembly 112 can be actuated to move a cutting and/or stapling member through end effector 106 in order to incise and/or staple tissue captured within end effector 106. After the tissue has been sufficiently incised and/or stapled, closure trigger 108 can be released in order to move closure tube 112 in an opposite longitudinal direction and open anvil 114. Other surgical instruments are disclosed in U.S. Pat. No. 7,441,685, entitled SURGICAL STAPLING INSTRUMENT WITH A RETURN MECHANISM, which issued on Oct. 28, 2008, the entire disclosure of which is hereby incorporated by reference herein. Further surgical instruments are disclosed in U.S. patent application Ser. No. 12/008,303, entitled SURGICAL STAPLING INSTRUMENT WITH A GEARED RETURN MECHANISM, which was filed on Jan. 10, 2008, and U.S. patent application Ser. No. 12/008,266, entitled SURGICAL STAPLING INSTRUMENT WITH A FIRING MEMBER RETURN MECHANISM, which was filed on Jan. 10, 2008, the entire disclosures of which are hereby incorporated by reference herein.

In various embodiments, referring once again to FIGS. 1A and 1B, a surgical instrument can further comprise an articulation joint, such as articulation joint 120, for example, which can be configured to permit end effector 106 to move relative to elongate shaft 104. In at least one embodiment, end effector 106 can further comprise a pivot plate 122 which can be retained within staple cartridge channel 113 by channel pin 124. As illustrated in FIG. 1B, channel pin 124 can be inserted, press-fit, and/or snap-fit into and/or through apertures 111 in cartridge channel 113 and aperture 121 in pivot plate 122 in order to secure pivot plate 122 to cartridge channel 113. In certain embodiments, pivot plate 122 can be immovably retained within staple cartridge channel 113. Further to the above, elongate shaft 104 can further comprise pin insert plate 126 which can be secured in position by spine 116 wherein, in at least one embodiment, pin insert plate 126 can be immovably retained within elongate shaft 104. Referring primarily to FIG. 1B, pivot plate 122 can further comprise pin aperture 123 which can be configured to receive articulation pin 127 extending from pin insert plate 126. In various embodiments, pin 127 and pin aperture 123 can be sized and configured to define an axis, such as axis 128, for example, about which staple cartridge channel 113 and pivot plate 122 can rotate relative to pin insert plate 126. As a result of the above, end effector 106 can be articulated relative to elongate shaft 104 in order to suitably position end effector 106 within a surgical site, for example. Once suitably positioned, end effector 106 can be locked in position relative to shaft 104. In certain embodiments, elongate shaft 104 can further comprise a lock or brake, such as lock 130, for example, which can be configured to selectively engage pivot plate 122, for example, and hold it in position relative to pin insert plate 126. In at least one such embodiment, pivot plate 122 can include one or more teeth 125 which can be captured within, or meshed with, one or more grooves 131 in the distal end of lock 130 such that relative movement between teeth 125 and grooves 131 is prevented, or at least limited.

In use, lock 130 can be disengaged from pivot plate 122 such that end effector 106 can be rotated relative to elongate shaft 104. Once lock 130 has been disengaged from pivot plate 122, in at least one such embodiment, end effector 106 can be placed against a cavity wall within a surgical site, such as the peritoneal cavity wall, for example, and a longitudinal force can be applied to shaft 104 via handle assembly 102 in order to rotate end effector 106 relative to elongate shaft 104. In certain circumstances, such articulation can be referred to as passive articulation. In any event, once end effector 106 has been suitably articulated, lock 130 can be re-engaged with pivot plate 122 and closure tube 112 can be advanced longitudinally by trigger 108 in order to close anvil 114 as described above. The reader will note that, when end effector 106 is moved between a straight position, i.e., a position in which it is aligned or at least substantially aligned with elongate shaft 104, and an articulated position, distal tube portion 118 can be moved between a first angle with respect to closure tube 112 and a second, or different, angle with respect to closure tube 112. In order to accommodate such relative movement, referring to FIGS. 2 and 3, pivot links 211 can be pivotably connected to distal tube portion 118 and closure tube 112 via pin projections 109 extending from pivot links 211 and via apertures 107 within tube portion 118 and closure tube 112. Pin projections 109 and pin apertures 107 can be configured such that pivot links 211 can provide at least one degree of freedom between distal tube portion 118 and closure tube 112. In such embodiments, pivot links 211 can permit distal tube 118 to articulate relative to closure tube 112 even though at least a portion of closure tube 112 has been advanced distally past articulation joint 120. In any event, once anvil 114 has been suitably closed, trigger 110 can be actuated to advance a firing bar distally into end effector 106. Although a firing bar is not illustrated in FIGS. 1A and 1B, surgical instrument 200, referring to FIGS. 2-4, includes a suitable firing bar 250 and cutting member 252 which can be configured to be advanced into and/or within end effector 106. In at least one embodiment, the elongate shaft and/or end effector of surgical instrument 100, for example, can include one or more slots configured for receiving and/or guiding firing bar 250 and/or cutting member 252 when they are advanced and/or retracted within the shaft and/or end effector of surgical instrument 100.

Figure 2:
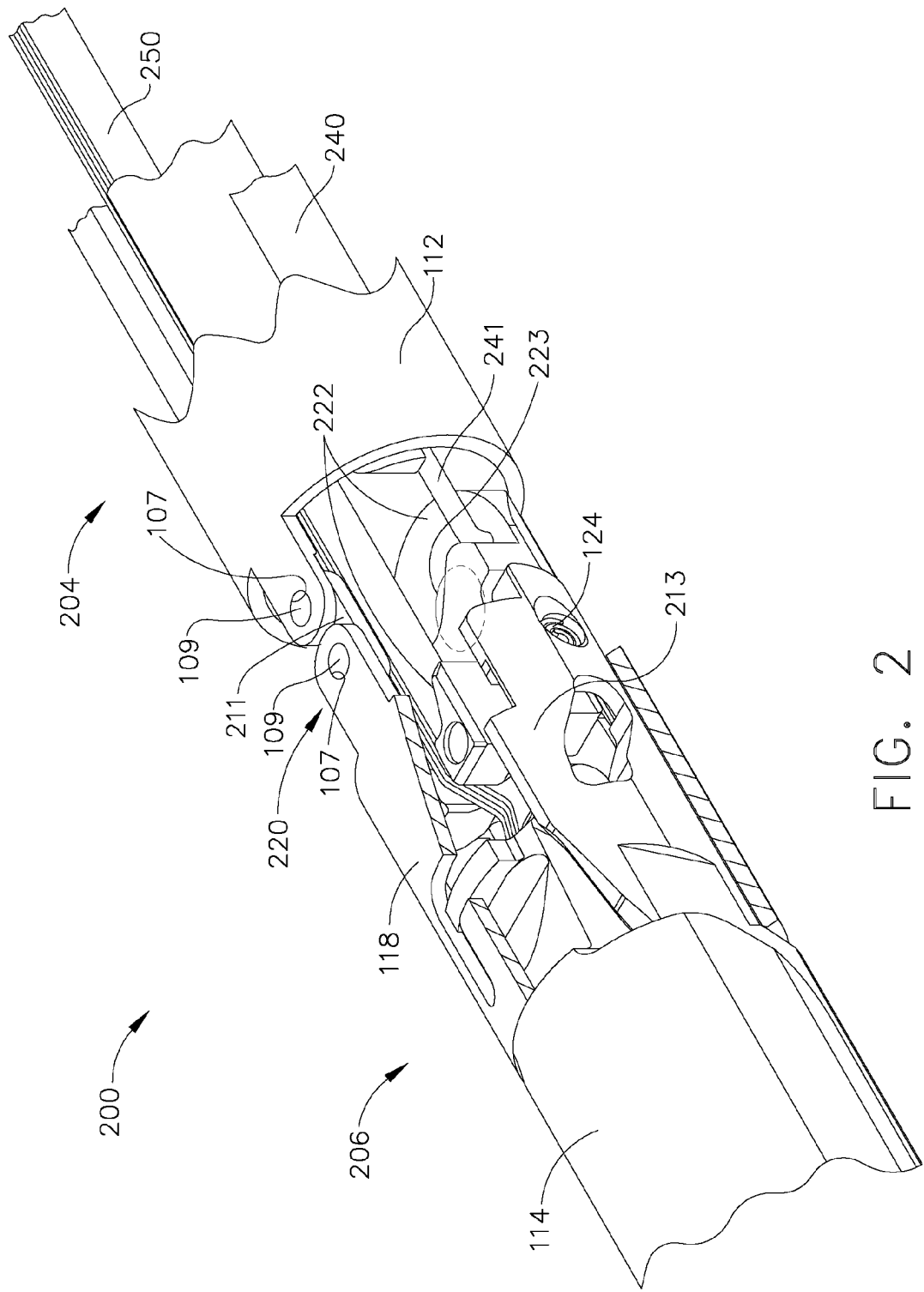
FIG. 2 is a perspective view of an articulation joint connecting an end effector and an elongate shaft of a surgical instrument in accordance with at least one embodiment of the present invention, the articulation joint being illustrated with some components removed.
Figure 3:
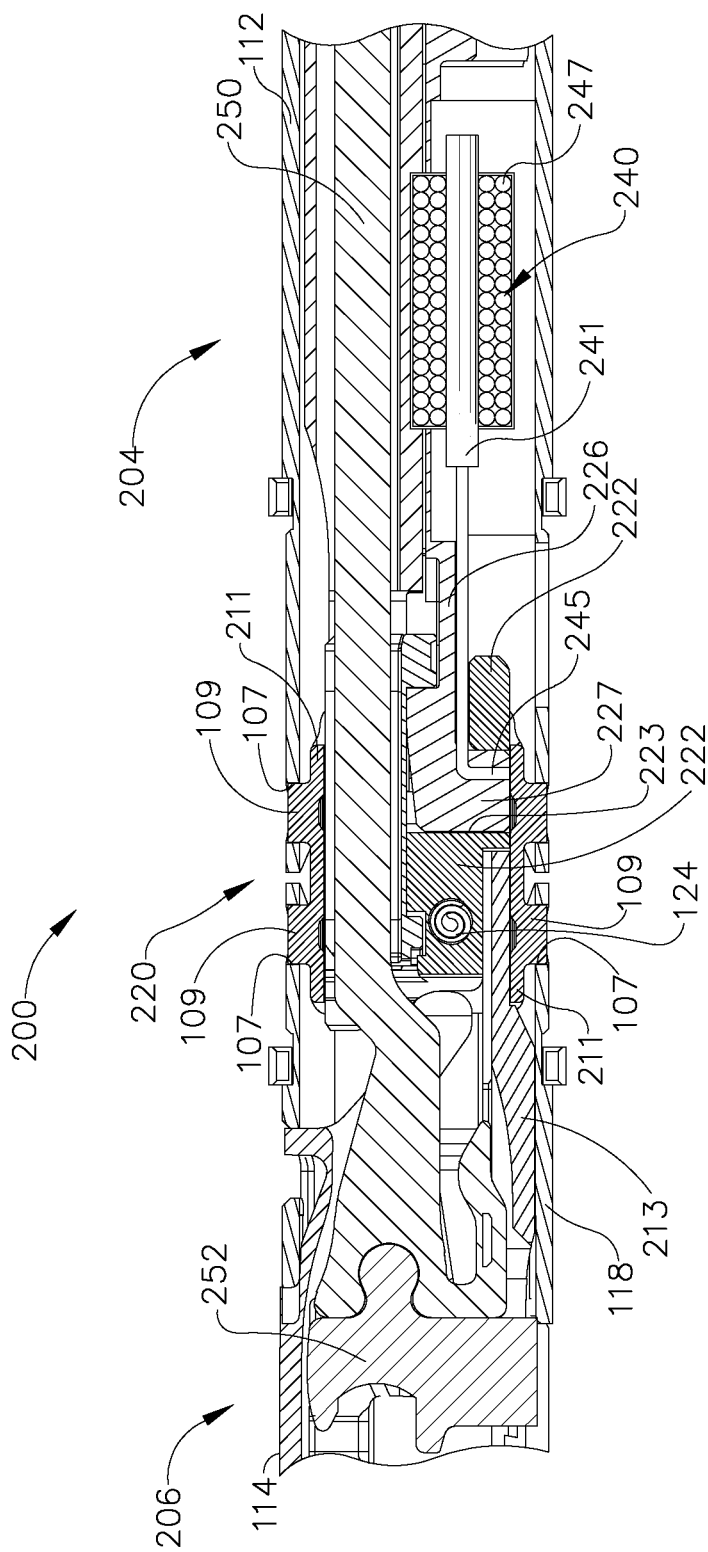
FIG. 3 is across-sectional view of the end effector of FIG. 2 illustrating a solenoid positioned within the elongate shaft of the surgical instrument, wherein the solenoid is configured to articulate the end effector.
Figure 4:
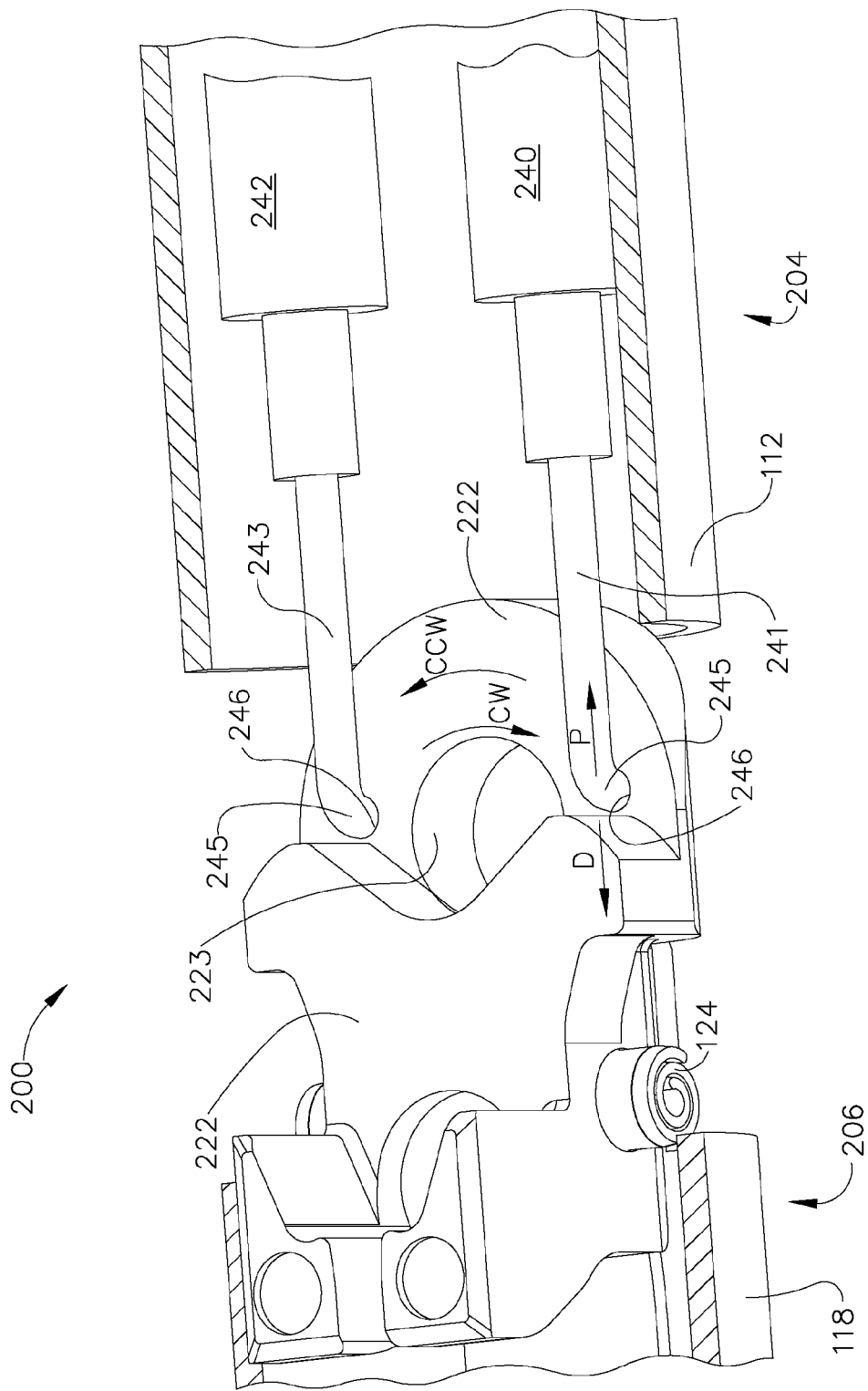
FIG. 4 is a partial perspective view of the end effector, articulation joint, and elongate shaft of FIG. 2 illustrated with some components removed.
Figure 9:
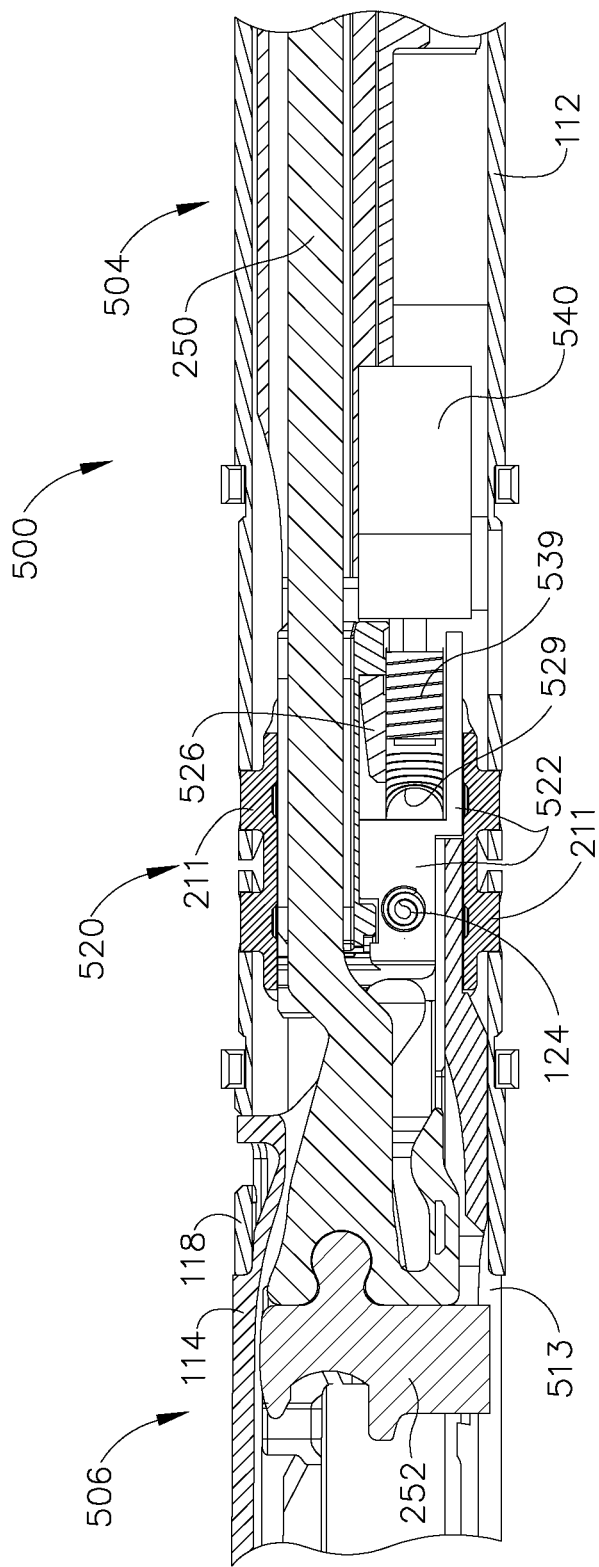
FIG. 9 is a cross-sectional view of an articulation joint connecting an end effector and an elongate shaft of a surgical instrument in accordance with at least one embodiment of the present invention.
Figure 10:
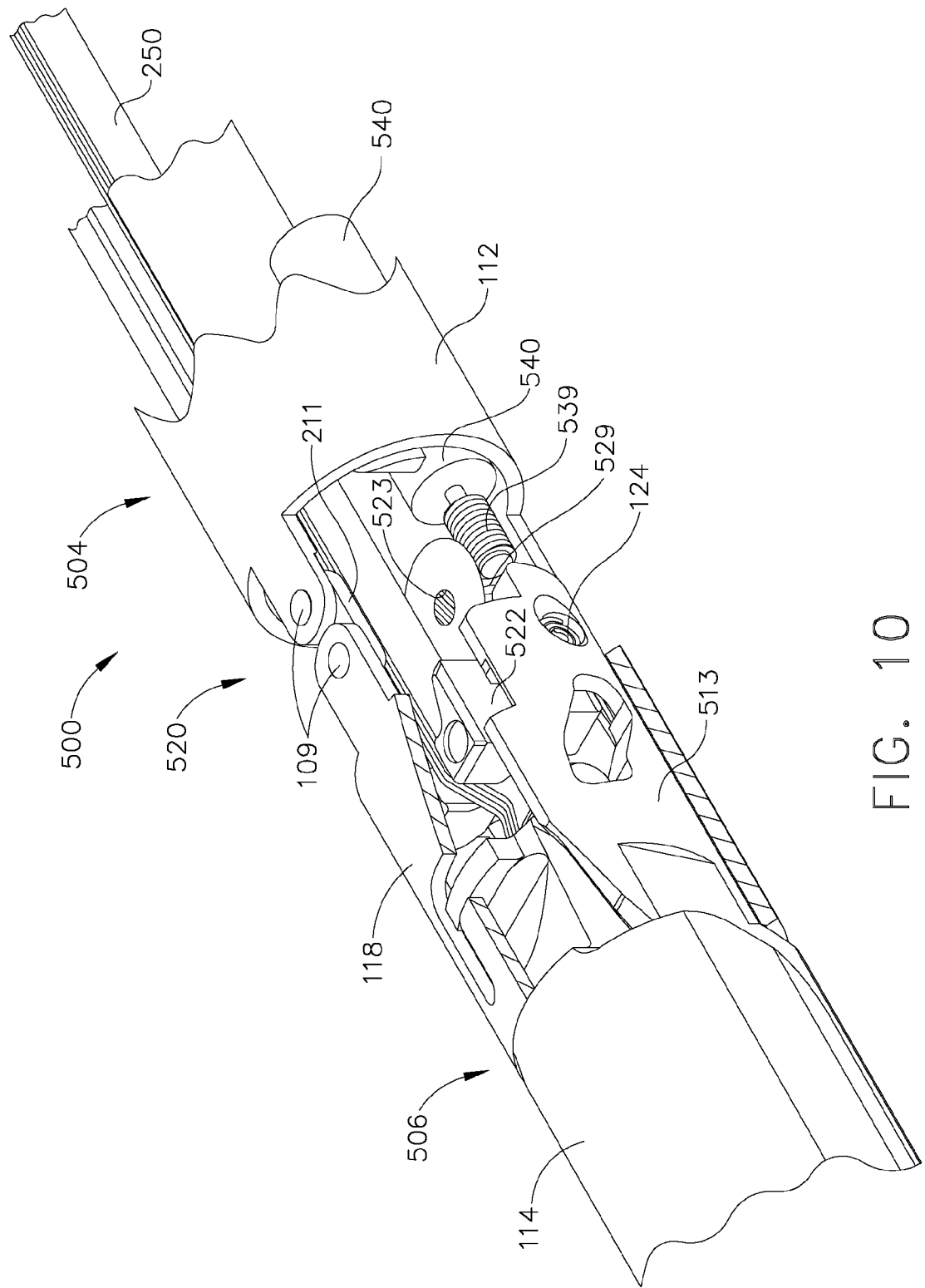
FIG. 10 is a partial perspective view of the end effector, the articulation joint, and the elongate shaft of FIG. 9 illustrating a motor operably engaged with a worm gear configured to articulate the end effector.
Figure 11:
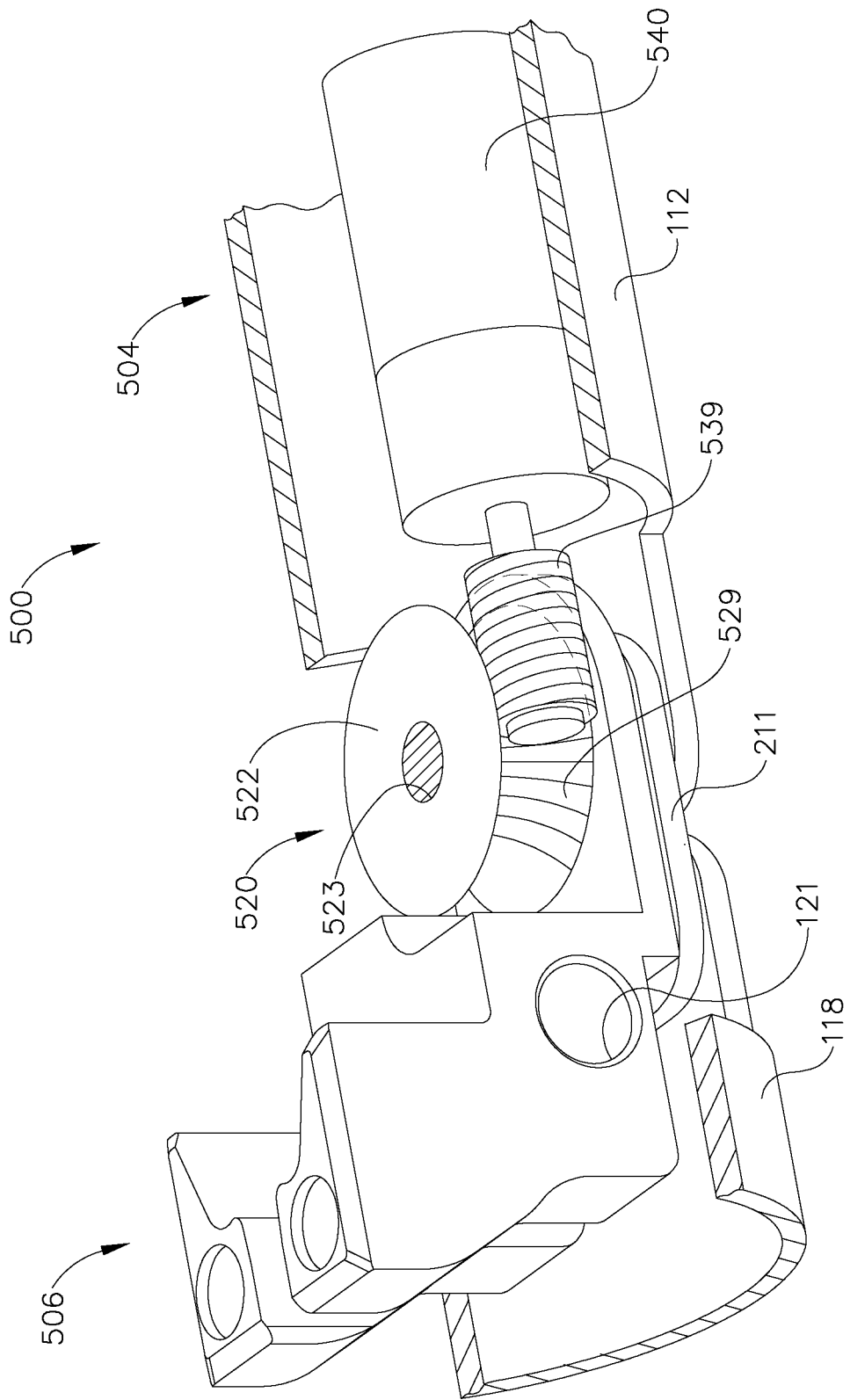
FIG. 11 is another partial perspective view of the end effector, the articulation joint, and the elongate shaft of FIG. 9 illustrated with some components removed.
Figure 12:
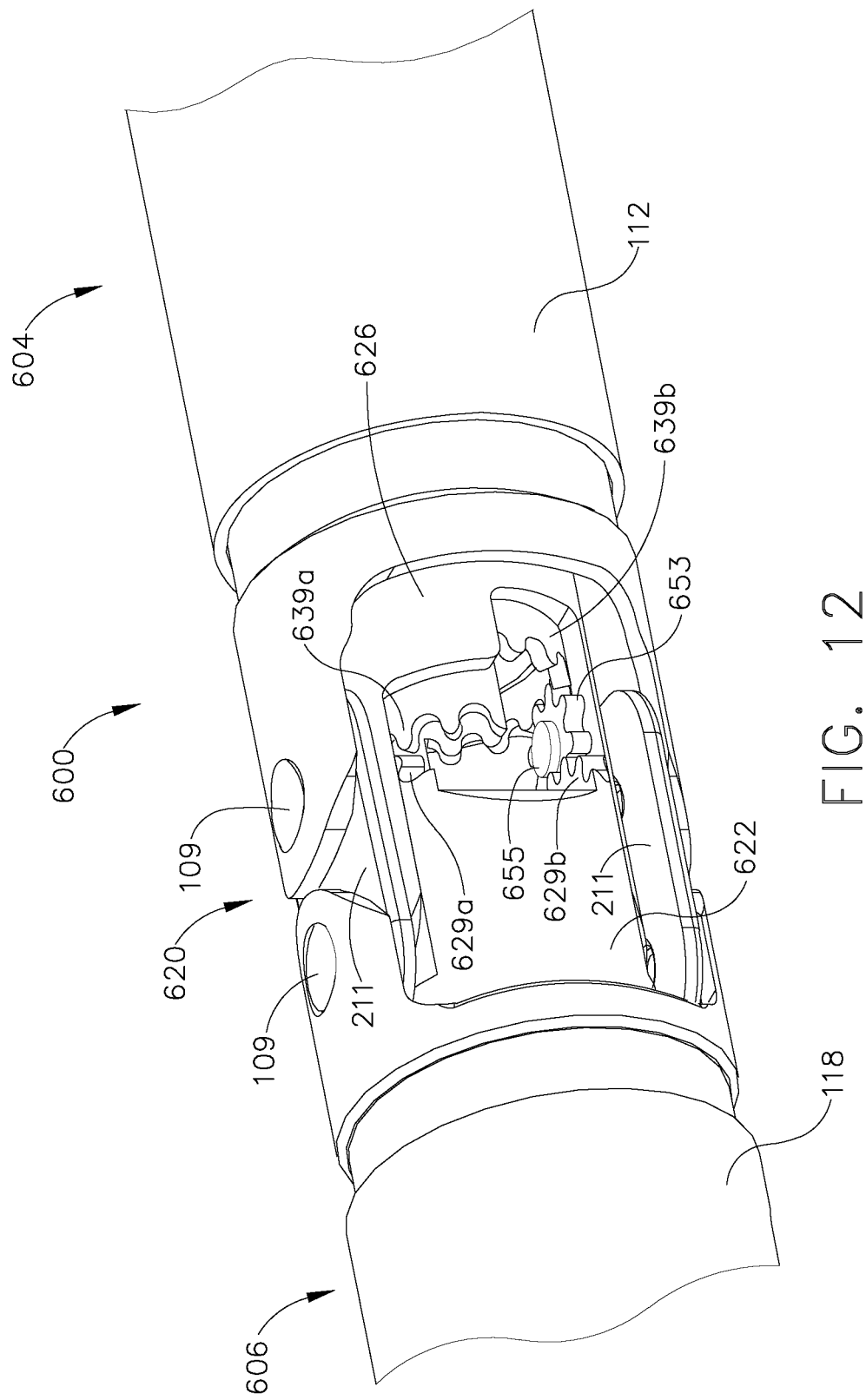
FIG. 12 is a partial perspective view of an articulation joint connecting an end effector and an elongate shaft of a surgical instrument in accordance with at least one embodiment of the present invention.
Figure 13:
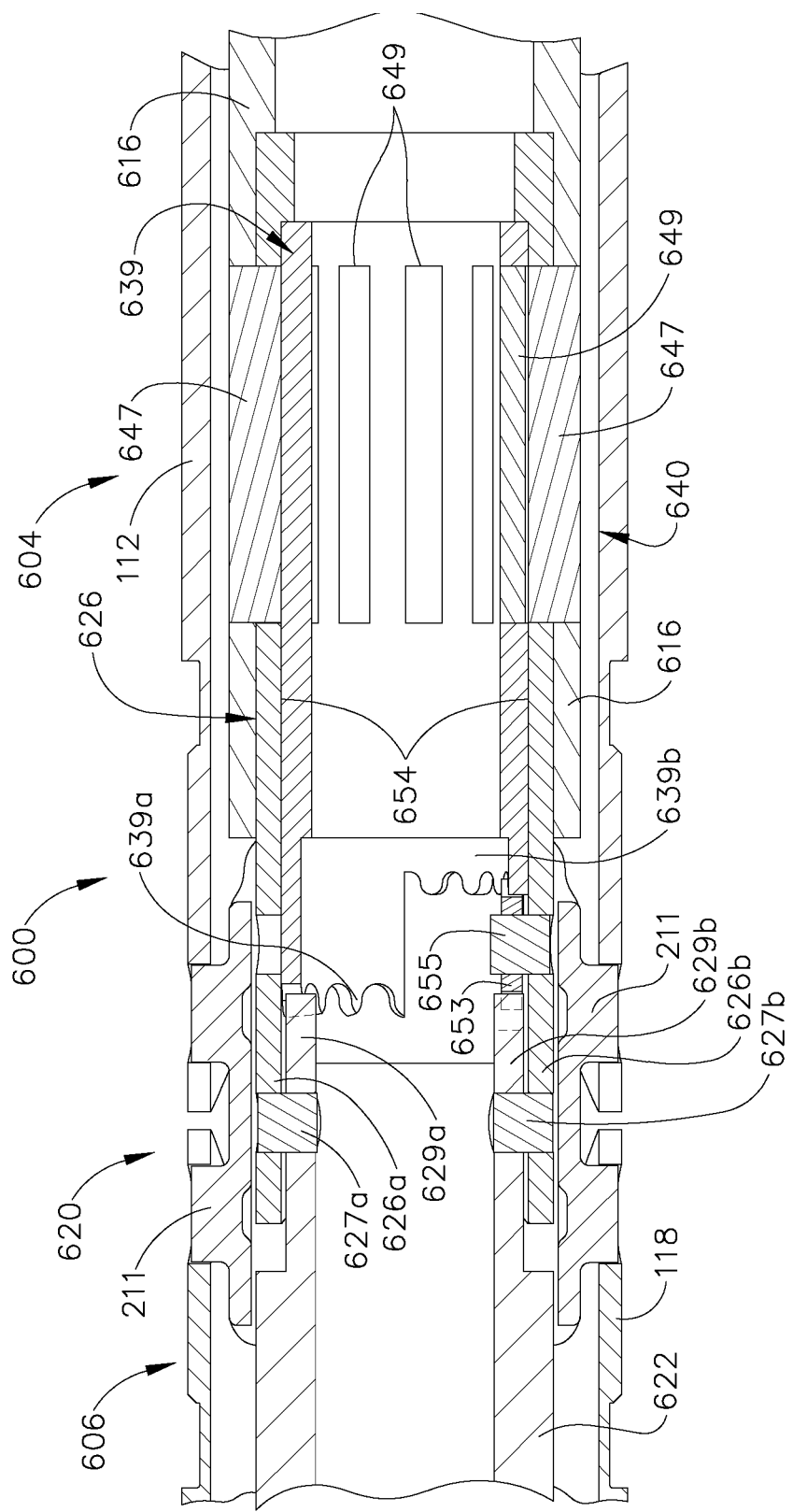
FIG. 13 is a cross-sectional view of the end effector, the articulation joint, and the elongate shaft of FIG. 12 illustrating a motor driven tube configured to articulate the end effector.
Figure 14:
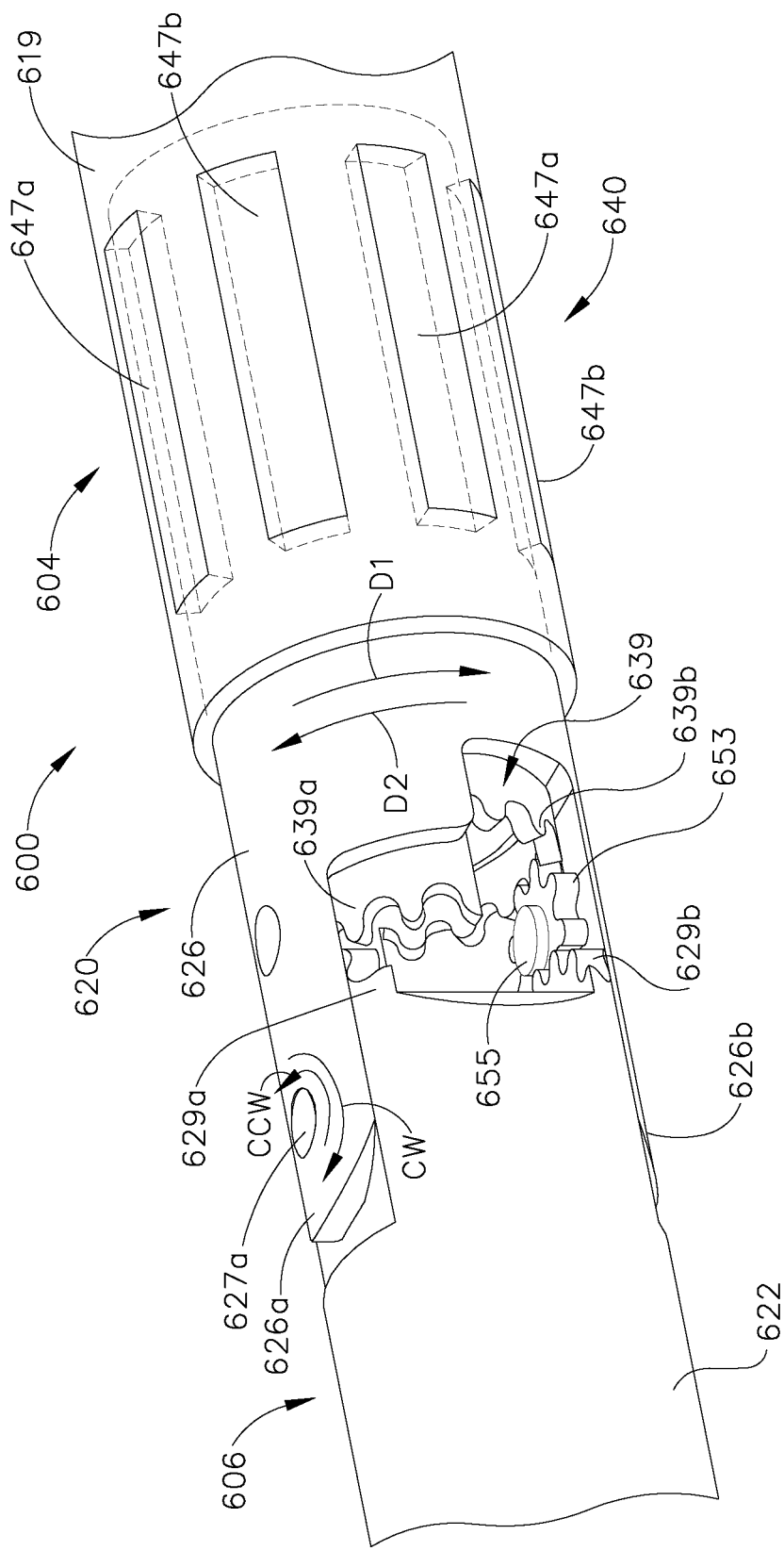
FIG. 14 is another partial perspective view of the end effector, the articulation joint, and the elongate shaft of FIG. 12 with some components removed and others illustrated in phantom lines.

In various embodiments, referring to FIGS. 2-4, a surgical instrument, such as surgical instrument 200, for example, can include an elongate shaft 204 and an end effector 206, wherein end effector 206 can be configured to articulate relative to elongate shaft 204 about articulation joint 220. Similar to surgical instrument 100, end effector 206 can comprise a pivot plate 222 retained within a staple cartridge channel 213, wherein pivot plate 222 can comprise a pin aperture 223 configured to receive articulation pin 227 extending from pin insert plate 226. In various embodiments, referring primarily to FIG. 4, elongate shaft 204 can further comprise one or more actuators which can be configured to rotate, or pivot, end effector 206 relative to shaft 204. In at least one such embodiment, elongate shaft 204 can further comprise first solenoid 240 and second solenoid 242 mounted therein which can be operably engaged with pivot plate 222 such that the actuation of first solenoid 240 and/or second solenoid 242 can rotate pivot plate 222 about an axis, for example. In certain embodiments, first solenoid 240 can comprise a piston and/or rod 241 sufficiently mounted to pivot plate 222 such that pivot plate 222 can be pushed distally and/or pulled proximally by first solenoid 240 in order to rotate end effector 206 in clockwise (CW) and/or counter-clockwise (CCW) directions. In certain circumstances, such articulation can be referred to as active articulation.

In various embodiments, further to the above, rod 241 can be advanced distally in a direction indicated by arrow "D" in order to rotate end effector 206 in a clockwise direction indicated by arrow "CW". In order to rotate end effector 206 in a counter-clockwise direction indicated by arrow "CCW", rod 241 can be retracted proximally in a direction indicated by arrow "P". In certain embodiments, rod 241 can include a distal end 245 which can be positioned within an aperture 246 in pivot plate 222 such that rod 241 can pivot relative pivot plate 222. In at least one embodiment, rod 241 can be suitably flexible to accommodate relative movement between pivot plate 222 and solenoid 240. In certain embodiments, solenoid 240 can be slidably and/or rotatably mounted within elongate shaft 204 such that rod 241 does not unsuitably bend or bind when it is extended or retracted to drive pivot plate 222 about an axis. In any event, referring to FIG. 3, solenoid 240 can include coils or windings 247 which can be energized by an electrical current and/or voltage in order to create a sufficient magnetic field to move rod 241 in a distal and/or proximal direction, depending on the direction in which the current is flowing through, and/or the polarity of the voltage applied to, the windings. In at least one such embodiment, piston and/or rod 241 can comprise an iron core, for example, which can be configured to interact with the magnetic field produced by the solenoid windings 247.

In certain embodiments, further to the above, elongate shaft 204 can include at least one additional solenoid, such as solenoid 242, for example, which can be configured to rotate pivot plate 222 contemporaneously with, and/or independently of, solenoid 240. In at least one such embodiment, solenoid 242 can comprise a piston and/or rod 243 which can be advanced distally and/or proximally in order to rotate end effector 206 in a clockwise and/or clockwise direction. Conversely to solenoid 240, rod 243 can be extended distally to rotate pivot plate 222 in a counter-clockwise direction and/or retracted proximally to rotate pivot plate 222 in a clockwise direction. Similar to solenoid 240, rod 243 can include a distal end 245 which can be pivotably mounted within an aperture 246 in pivot plate 222. Also similar to solenoid 240, solenoid 242 can be rotatably and/or slidably mounted within elongate shaft 204 in order to add at least one degree of freedom to a system of linkages comprising pivot plate 222, pin insert plate 226, solenoid 242, and rod 243 in order to permit articulation between end effector 206 and shaft 204.

As described above, an end effector of a surgical instrument can be locked into position once the end effector has been suitably articulated. In various embodiments, referring to FIGS. 5 and 6, a surgical instrument, such as surgical instrument 300, for example, can include an elongate shaft 304 and an end effector 306, wherein end effector 306 can be configured to articulate relative to elongate shaft 304 about articulation joint 320. Similar to surgical instrument 100, end effector 306 can comprise a pivot plate 322 retained within a staple cartridge channel 313, wherein pivot plate 322 can comprise a pin aperture 323 configured to receive articulation pin 327 extending from a pin insert plate 326 retained within elongate shaft 304. In certain embodiments, elongate shaft 304 can further comprise a lock, or brake, and a lock actuator which can be configured to engage the lock with pivot plate 322 and, as a result, hold pivot plate 322 in position relative to elongate shaft 304. In at least one embodiment, elongate shaft 304 can comprise lock actuator 332 which can be configured to move lock 330 distally to engage lock 330 with plate 322 and/or move lock 330 proximally to disengage lock 330 from plate 322. In at least one such embodiment, lock actuator 332 can comprise a solenoid mounted within elongate shaft 304 wherein the solenoid can comprise a piston and/or rod 333 which can be extended distally and/or retracted proximally by coils or windings 334. In certain embodiments, lock 330 can be mounted to rod 333 such that the displacement of rod 333 can displace lock 330 toward and/or away from pivot plate 322. Similar to the above, lock 330 can be biased into contact with pivot plate 322 such that groove 331 in the distal end of lock 330 can engage, or mesh with, a projection, or tooth, 325 extending from pivot plate 322. In at least one embodiment, lock actuator 332 can further comprise a biasing element, such as spring 335, for example, which can be configured to bias lock 330 into engagement with pivot plate 322. In at least one such embodiment, the solenoid of lock actuator 332 can overcome the biasing force applied by spring 335 in order to disengage lock 330 from pivot plate 322. In certain embodiments, spring 335 can be compressed between a flange 336 extending from lock 330 and a stationary, or at least substantially stationary, flange 337 in elongate shaft 306 such that spring 335 can apply a biasing force to lock 330. In at least one embodiment, spring 335 can comprise a linear spring wherein the force in which it applies can be proportional to the distance in which it is compressed.

In various embodiments, referring to FIGS. 7 and 8, a surgical instrument, such as surgical instrument 400, for example, can include one or more motors configured to articulate an end effector of the surgical instrument. In such embodiments, a motor can comprise an induction motor, a brushless DC motor, a stepper motor, and/or a synchronous motor, for example. In certain embodiments, surgical instrument 400 can comprise an elongate shaft 404 and an end effector 406, wherein end effector 406 can be configured to articulate relative to elongate shaft 404 about articulation joint 420. Similar to surgical instrument 100, end effector 406 can comprise a pivot plate 422 retained within a staple cartridge channel 413, wherein pivot plate 422 can comprise a pin aperture 423 configured to receive articulation pin 427 extending from a pin insert plate 426 retained within elongate shaft 404. In at least one embodiment, elongate shaft 404 can further comprise a motor, such as motor 440, for example, mounted therein which can be operably engaged with pivot plate 422 in order to rotate, or articulate, end effector 406 relative to shaft 404. More particularly, in at least one such embodiment, motor 440 can be configured to rotate a gear, such as spur gear 439, for example, which can be meshingly engaged with one or more teeth, such as teeth 429, for example, on pivot plate 422 such that the rotation of spur gear 439 can be transmitted to pivot plate 422. In at least one such embodiment, teeth 429 can be arranged in an at least partially annular array around the perimeter of pivot plate 422. In various embodiments, elongate shaft 404 can further comprise a gear box, such as gear box 441, for example, for reducing, and/or increasing, the gear ratio between an input shaft driven by motor 440 and an output shaft which drives spur gear 439.

Similar to the above, a surgical instrument, such as surgical instrument 500, for example, can include one or more motors configured to articulate an end effector of the surgical instrument using a worm drive arrangement. In various embodiments, surgical instrument 500 can comprise an elongate shaft 504 and an end effector 506, wherein end effector 506 can be configured to articulate relative to elongate shaft 504 about articulation joint 520. Similar to surgical instrument 400, end effector 506 can comprise a pivot plate 522 retained within a staple cartridge channel 513, wherein pivot plate 522 can comprise a pin aperture 523 configured to receive an articulation pin extending from a pin insert plate 526 retained within elongate shaft 504. In at least one embodiment, elongate shaft 504 can further comprise a motor, such as motor 540, for example, mounted therein which can be operably engaged with pivot plate 522 in order to rotate, or articulate, end effector 506 relative to shaft 504. More particularly, in at least one such embodiment, motor 540 can be configured to rotate a worm, such as worm 539, for example, which can be meshingly engaged with a worm gear, or concave worm wheel portion, 529 on pivot plate 522 such that the rotation of worm 539 can be transmitted to pivot plate 522. A worm drive arrangement, such as the one described above, for example, can provide a very large gear ratio such that a gear box is not required to reduce the speed of the motor, although a gear box can be used. In certain embodiments, a worm drive arrangement can be self-locking. More particularly, the lead angle of the helical thread on worm 539 can be such that end effector 506 and worm gear portion 529 cannot be rotated in order to drive worm 539 and motor 540 in reverse. Stated another way, worm gear portion 529 and worm 539 can be configured such that they are friction-locked together if a rotational force is applied to end effector 506. In certain embodiments, as a result, the articulation of end effector 506 relative to elongate shaft 504 can only be controlled by the selective rotation of worm 539 by motor 540 in clockwise and counter-clockwise directions in order to rotate end effector 506 in left and right directions, for example, about articulation joint 520. In at least one such embodiment, a separate articulation lock, such as those described above, for example, may not be required, although they can be used.

Figure 15:
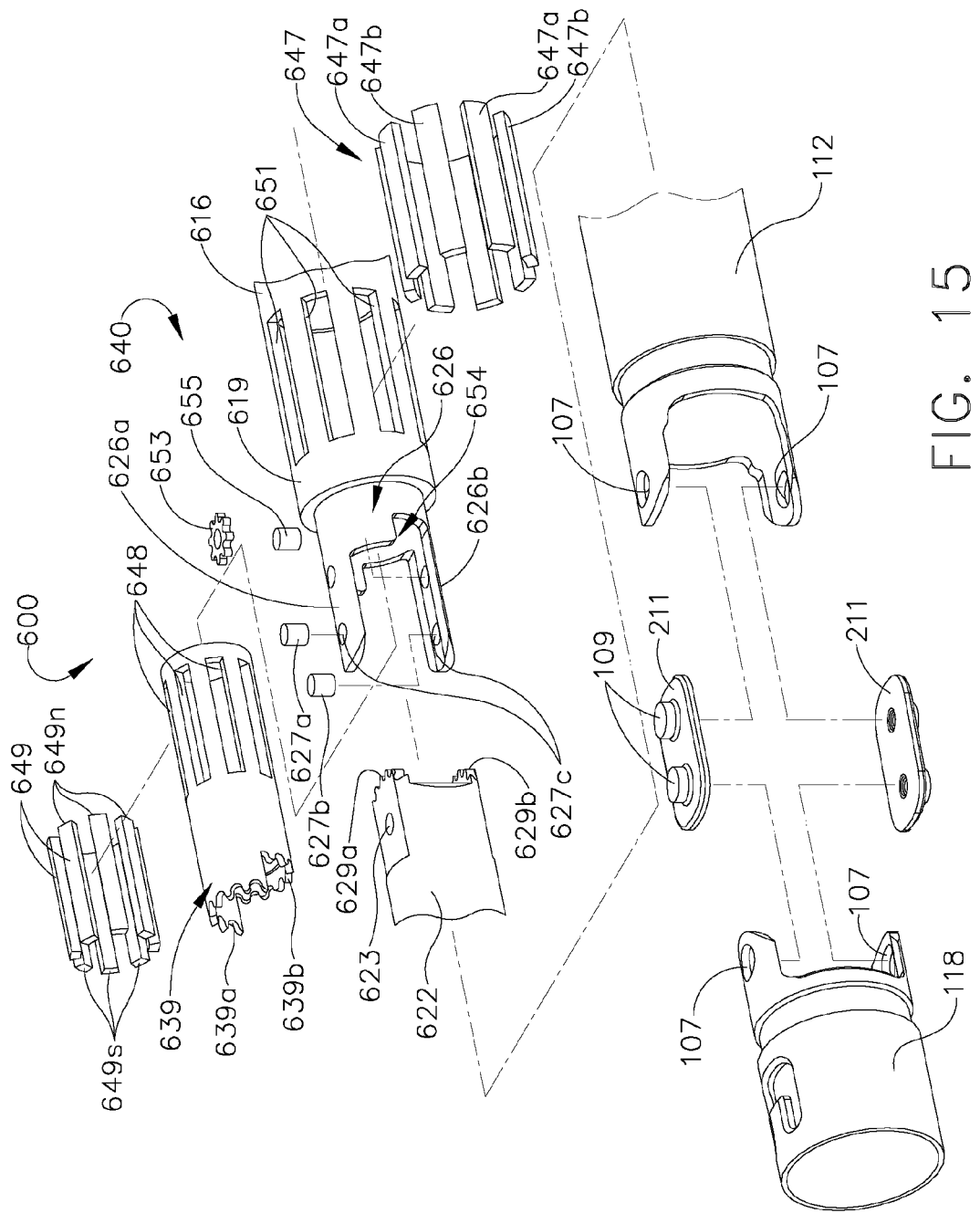
FIG. 15 is an exploded view of the articulation joint of FIG. 12.

In various embodiments, at least a portion of an elongate shaft of a surgical instrument, such as surgical instrument 600, for example, can comprise a motor configured to articulate an end effector of a surgical instrument. In various embodiments, referring to FIGS. 12-15, surgical instrument 600 can comprise an elongate shaft 604 and an end effector 606, wherein end effector 606 can be configured to articulate relative to elongate shaft 604 about articulation joint 620. In various embodiments, end effector 606 can further comprise a pivot member 622 mounted therein wherein, in at least some embodiments, pivot member 622 can be immovably mounted within end effector 606. In addition, elongate shaft 604 can comprise one or more motors, such as motor 640, for example, which can be configured to rotate pivot member 622 about an axis defined by pivot pins 627a and 627b. In at least one embodiment, motor 640 can comprise a spine portion 616 mounted within elongate shaft 604 and, in addition, a pivot pin member 626 mounted to spine portion 616, wherein spine portion 616 and pivot pin member 626 can be immovably mounted within elongate shaft 604. Referring to FIG. 15, pivot pin member 626 can comprise upper and lower tines 626a, 626b extending therefrom, wherein pivot pins 627a and 627b can extend from tines 626a and 626b, respectively, and can be mounted within apertures 627c within tines 626a and 626b in any suitable manner such as by a press-fit relationship and/or an adhesive, for example. In various embodiments, pivot member 622 can include one or more apertures, such as aperture 623, for example, configured to closely receive pivot pins 627a and 627b such that pivot member 622 and end effector 606 can be rotated or articulated about an axis as described above.

In various embodiments, further to the above, spine portion 616 and/or pivot pin member 626 can include one or more apertures or recesses, such as apertures 651, for example, which can be configured to receive one or more electromagnets, such as electromagnets 647, for example, mounted therein. Although not illustrated, surgical instrument 600 can further comprise one or more conductors, such as insulated wires, for example, which can be configured to conduct an electrical current through the wires when a current source and/or voltage source, such as a battery, for example, is operably coupled with the conductors. In at least one such embodiment, the conductors can extend from a handle assembly of the surgical instrument, such as handle assembly 102, for example, to the distal end of elongate shaft 606, wherein the conductors can be wrapped or coiled around ferromagnetic cores, which can be comprised of iron and/or cobalt, for example, to comprise electromagnets 647a and 647b. In use, in at least one embodiment, a surgical instrument can further include a switch, or actuator, which can be operated to selectively couple the current source and/or voltage source to the conductors. In certain embodiments, when electrical current is not flowing through the conductors, electromagnets 647a, 647b may not generate a magnetic field and, when sufficient electrical current is flowing through the conductors, the electrical current can generate one or more magnetic fields which can be utilized to rotate driver 639. Referring primarily to FIG. 15, driver 639 can include one or more magnetic elements mounted thereto which, when exposed to the magnetic field, or fields, created by electromagnets 647, can interact with the magnetic field, or fields, and cause driver 639 to rotate. In at least one such embodiment, driver 639 can comprise one or more apertures ore recesses, such as apertures 648, for example, which can be configured to receive one or more permanent magnets 649 therein.

In various embodiments, further to the above, permanent magnets 649 can comprise a magnetic polarity regardless of whether they are present in a magnetic field. In at least one embodiment, each permanent magnet 649 can comprise a positive, or north, pole 649n and a negative, or south, pole 649s, wherein poles 649n and 649s can be arranged such that, when the magnetic field, or fields, produced by the electromagnets 647a and 647b are selectively produced, such magnetic fields can interact with magnetic fields produced by permanent magnets 649 and, as a result, rotate driver 639. In various embodiments, driver 639 can be closely received and rotatably supported within aperture 654 in spine 616 such that driver 639 can be rotated about an axis when permanent magnets 649 are displaced within the magnetic field produced by electromagnets 647a and 647b. As outlined above, electromagnets 647a and 647b can be selectively energized to create a magnetic field which, owing to the polarity of permanent magnets 649, causes permanent magnets 649 to be displaced within the magnetic field(s). In various embodiments, electromagnets 647a and 647b can be energized such that electromagnets 647a have a different polarity than the polarity of electromagnets 647b. In at least one embodiment, electromagnets 647a and 647b can be energized such that they have opposite polarities, or different positive (north) and negative (south) poles, and such that the poles of electromagnets 647a and 647b are arranged in an alternating fashion. In various embodiments, the direction of current flowing through the conductors wrapped around the cores of electromagnets 647a, 647b can determine the polarity of the magnetic field(s) generated by the electromagnets. In use, the direction of the current flowing through the conductors as described above can be repeatedly switched, or alternated, such that the polarities of one or more of the electromagnets 647a and 647b can be repeatedly switched, or alternated, in order to attract and/or repel permanent magnets 649 in a manner such that driver 639 can be continuously rotated in clockwise and/or counter-clockwise directions, for example.

As described above, the operation of permanent magnets 647a, 647b can rotate driver 639 in a clockwise and/or counter-clockwise direction. In various embodiments, driver 639 can further comprise one or more gear portions, or drive teeth, which can be configured to engage or mate with a corresponding gear portion, or drive teeth, on pivot member 622. More particularly, in at least one embodiment, driver 639 can include a first gear portion 639a extending therefrom which can be configured to engage a first gear portion 629a extending from pivot member 622 such that, when driver 639 is rotated as described above, first gear portion 639a can drive first gear portion 629a to pivot or articulate pivot member 622 and, correspondingly, end effector 606 about pivot pins 627a and 627b. In at lest one such embodiment, referring primarily to FIG. 14, driver 639 can be rotated in a first direction indicated by arrow D1 in order to rotate end effector 606 in a clockwise direction indicated by arrow CW and, in addition, driver 639 can be rotated in a second direction indicated by arrow D2 in order to rotate end effector 606 in a counter-clockwise direction indicated by arrow CCW. In at least one embodiment, as a result, driver 639 can be rotated about a first axis and end effector 606 can be rotated about a second axis, wherein the first axis and the second axis can be perpendicular, or at least substantially perpendicular, to each other. In other embodiments, the first and second axes may be non-parallel, transverse, and/or skew to one another. In various embodiments, referring again to FIG. 14, driver 639 can further include a second gear portion 639b which can be operably engaged with a second gear portion 629b of pivot member 622 via a transmission gear 653. In at least one such embodiment, transmission gear 653 can be rotatably mounted to pivot pin member 626 by a pin, such as pin 655, for example, such that, when driver 639 is rotated in direction D1 as described above, second gear portion 639b can assist first gear portion 639a in rotating pivot member 622 in a clockwise direction CW, for example.

Figure 16:
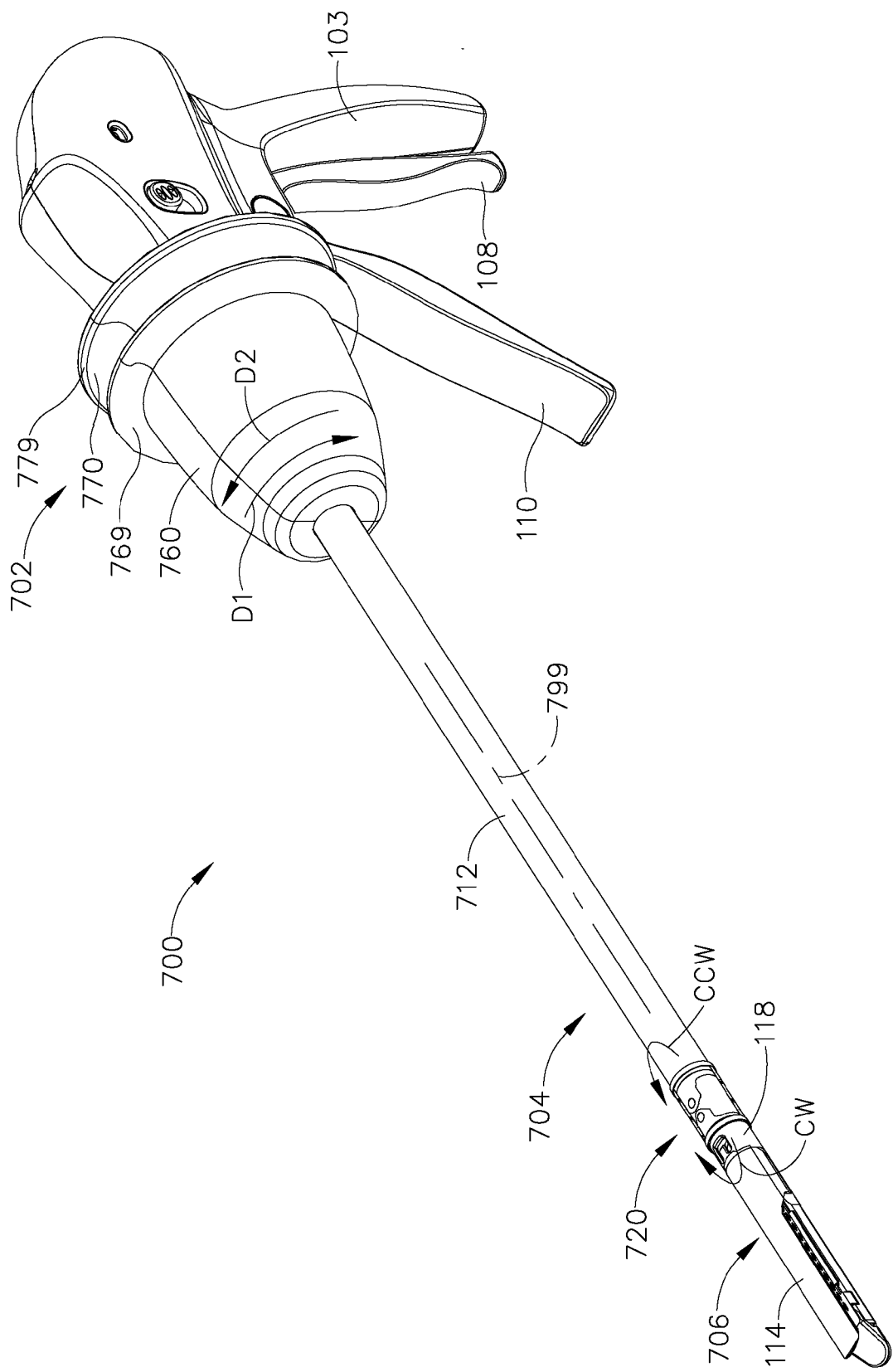
FIG. 16 is a perspective view of a surgical instrument having an articulation knob for articulating an end effector of the surgical instrument and a rotation knob for rotating the end effector.

As outlined above, a surgical instrument can include a handle assembly for operating the surgical instrument. In various embodiments, referring now to FIGS. 16 and 17, a surgical instrument, such as surgical instrument 700, for example, can comprise a frame 701, a closure trigger 108 pivotably mounted to frame 701, and, in addition, a firing trigger 110 also pivotably mounted to frame 701. Similar to surgical instrument 100, the operation of closure trigger 108, and the closure drive associated therewith, can displace closure tube 712 longitudinally along elongate shaft 704 in order to open and close anvil 114. In certain embodiments, referring primarily now to FIG. 17, the closure drive can comprise a retaining collar 108b slidably positioned within frame 701 and, in addition, a closure link 108a pivotably mounted to retaining collar 108b and trigger 108. In at least one such embodiment, at least a portion of closure tube 712 can be retained within retaining collar 108b such that the rotation of closure trigger 108 toward pistol grip 103 can displace closure link 108a, retaining collar 108b, and closure tube 712 distally, i.e., in a direction indicated by arrow D.

Figure 19:
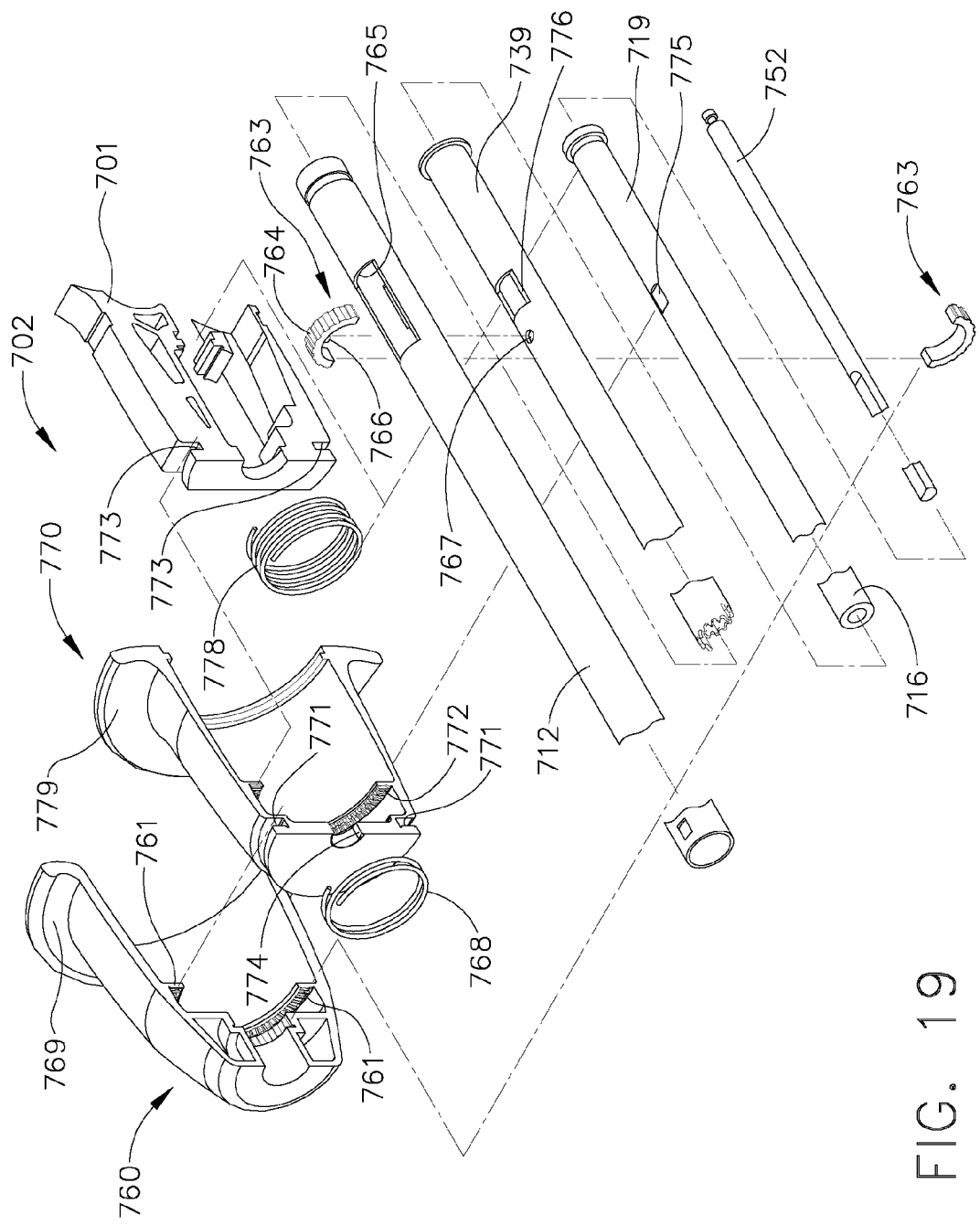
FIG. 19 is an exploded view of the handle portion of FIG. 17.

In addition to the closure drive described above, handle assembly 702 can further comprise an articulation system configured to rotate a driver, such as driver 739, for example, in order to articulate end effector 706 relative to elongate shaft 704. In at least one such embodiment, handle assembly 702 can further comprise articulation knob 760 which can be moved between locked and unlocked positions wherein, in certain embodiments, referring primarily to FIG. 17, articulation knob 760 can be slid between a first, or distal, position in which it is locked to rotation knob 770 and a second, or proximal, position in which it is unlocked from rotation knob 770. Referring primarily to FIG. 19, articulation knob 760 can comprise one or more locking teeth, or projections, 761 which can be configured to be engaged with one or more locking teeth, or projections, 771 on rotation knob 770 such that articulation knob 760 cannot be rotated relative to rotation knob 770 when articulation knob 760 is positioned in its locked, or distal, position. In at least one such embodiment, as a result, articulation knob 760 cannot be utilized to rotate driver 739 and articulate end effector 706 when articulation knob 760 is in its locked position.

Figure 18:
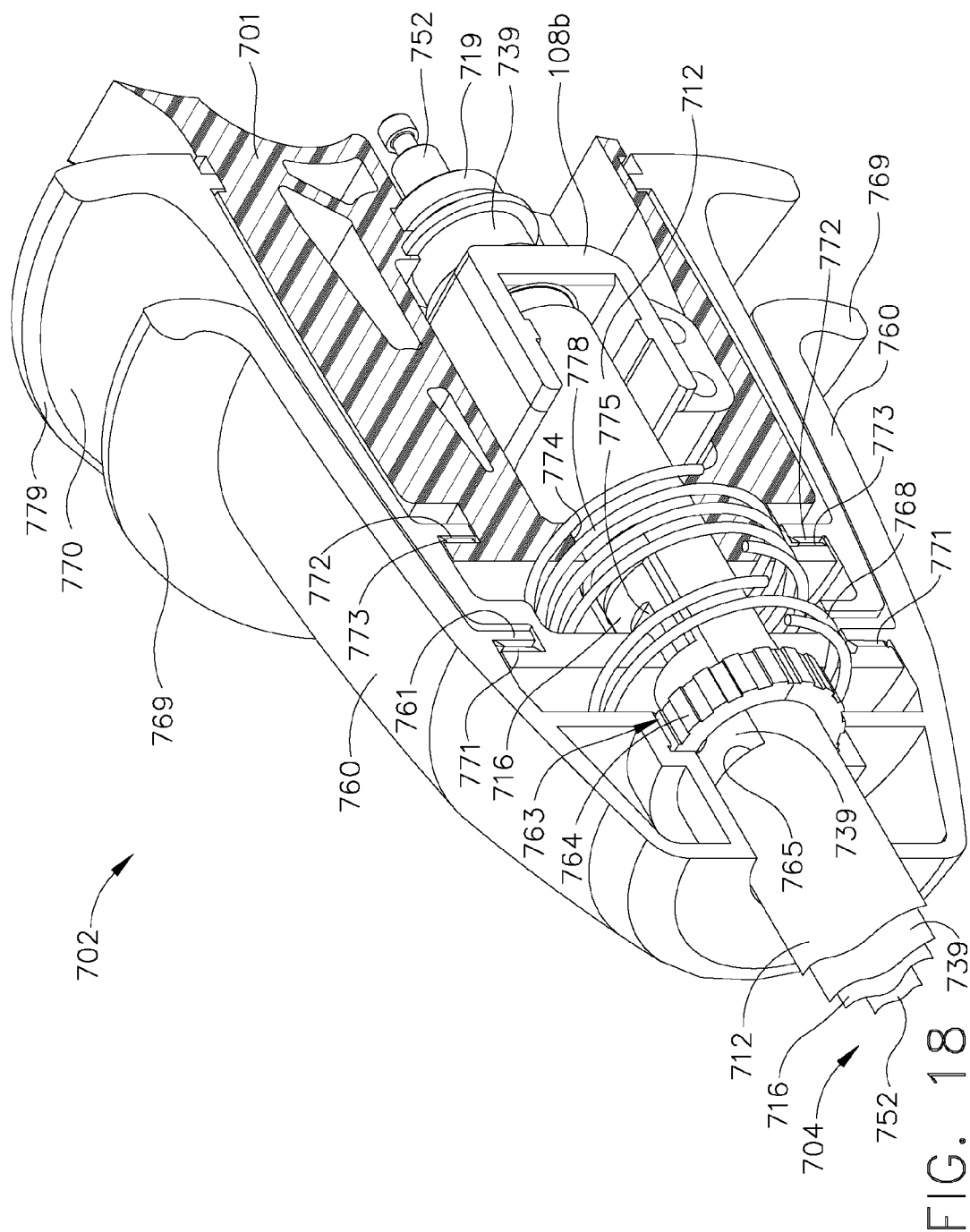
FIG. 18 is a perspective cross-sectional view of the handle portion of FIG. 17.

Further to the above, when articulation knob 760 is moved into its unlocked, or proximal, position, locking teeth 761 can be sufficiently disengaged from locking teeth 771 such that articulation knob 760 can be rotated relative to rotation knob 770. In at least one such embodiment, referring again to FIG. 16, articulation knob 760 can be rotated in a first direction indicated by arrow D1 in order to rotate end effector 706 in a clockwise direction indicated by arrow CW and, correspondingly, articulation knob 760 can be rotated in a second direction indicated by arrow D2 in order to rotate end effector 706 in a counter-clockwise direction indicated by arrow CCW, for example. Referring primarily to FIG. 18, articulation knob 760 can be operably engaged with spline ring 763 such that, when articulation knob 760 is rotated, spline ring 763 can be rotated by articulation knob 760. In at least one such embodiment, referring to FIG. 18, spline ring 763 can include one or more splines 764 which can be configured to permit articulation knob 760 to be slid between its locked and unlocked positions, yet transmit rotational motion to spline ring 763. In various embodiments, referring now to FIG. 19, spline ring 763 can comprise two or more portions which can be assembled together such that spline ring 763 encompasses at least a portion of closure tube 712. In at least one such embodiment, closure tube 712 can include an aperture, or window, 765 which can be configured to permit at least a portion of spline ring 763 to extend through closure tube 712 and operably engage driver 739. More particularly, spline ring 763 can further comprise one or more projections, or keys, 766 extending therefrom which can be received within one or more apertures 767 in driver 739 such that, when spline ring 763 is rotated by articulation knob 760, spline ring 763 can rotate driver 739. In various embodiments, as a result, articulation knob 760 and driver 739 can be rotated relative to closure tube 712 and spine member 716 when articulation knob 760 is in its unlocked position.

In use, as outlined above, articulation knob 760 can be pulled proximally to disengage locking teeth 761 from locking teeth 771 of rotation knob 770. In various embodiments, referring generally to FIG. 16, articulation knob 760 can further comprise lip 769 extending therefrom wherein, in at least one embodiment, lip 769 can be configured to allow a surgeon to grasp lip 769 with one or more fingers and pull articulation knob 760 proximally. In such circumstances, referring to FIG. 17, articulation knob 760 can compress a biasing member, such as spring 768, for example, positioned intermediate articulation knob 760 and rotation knob 770. In certain embodiments, articulation knob 760, driver 739, and end effector 706 can be configured such that, when articulation knob 760 is rotated substantially 10 degrees in direction D1, for example, end effector 706 can be rotated substantially 10 degrees in direction CW. Such embodiments can be referred to as having a 1:1 gear ratio, although other embodiments are envisioned which can have a smaller gear ratio or a larger gear ratio. In any event, once end effector 706 has been satisfactorily articulated, the surgeon can release articulation knob 760 such that spring 768 can move articulation knob 760 from its unlocked position into its locked position once again. Referring to FIG. 19, lock teeth 761 and/or lock teeth 771 can each comprise an array of teeth which can be configured such that at least some of lock teeth 761 and 771 can intermesh, or be interlocked, regardless of the degree in which articulation knob 760 is rotated relative to rotation knob 770. In the illustrated embodiment, teeth 761 and teeth 771 are each arranged in an annular, or at least substantially annular, and a concentric, or at least substantially concentric, array.

In various embodiments, further to the above, rotation knob 770 can be configured to rotate end effector 706 about a longitudinal axis, such as longitudinal axis 799, for example. In at least one such embodiment, referring primarily to FIG. 17, rotation knob 770 can be moved between a locked, distal, position in which it is locked to frame 701 and an unlocked, proximal, position in which it is unlocked from frame 701. In various embodiments, referring to FIG. 17 once again, rotation knob 770 can further comprise lip 779 extending therefrom wherein, in at least one embodiment, lip 779 can be configured to allow a surgeon to grasp lip 779 with one or more fingers and pull rotation knob 770 proximally. Similar to the above, referring primarily to FIG. 19, rotation knob 770 can comprise one or more locking teeth, or projections, 772 which can be configured to be engaged with one or more locking teeth 773, or projections, on frame 701 such that rotation knob 770 cannot be rotated relative to frame 701 when rotation knob 770 is positioned in its locked, or distal, position. When rotation knob 770 is unlocked from frame 701, however, rotation knob 770 can be rotated relative to frame 701 in order to rotate end effector 706 about longitudinal axis 799. More particularly, in at least one embodiment, rotation knob 770 can further include one or more driver portions, such as flat driver portions 774, for example, which can be configured to transmit the rotation of rotation knob 770 to spine portion 716 via corresponding flat portions 775 on spine portion 716. In at least one such embodiment, referring primarily to FIG. 19, flat driver portions 774 can be configured to extend through window 765 in closure tube 712 and, in addition, window 776 in driver 739 such that flat driver portions 774 can directly engage flat portions 775 on spine 716.

Figure 17:
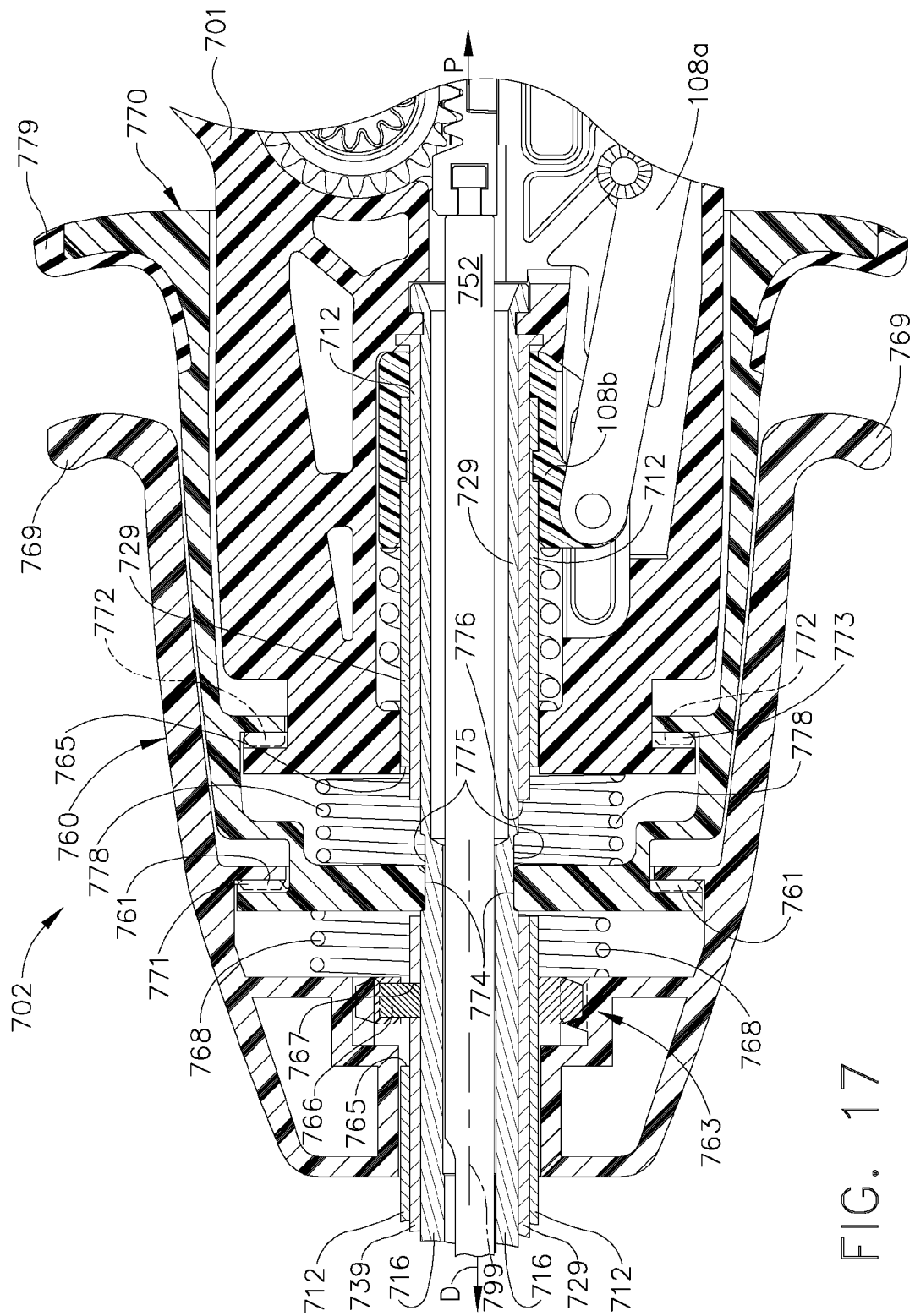
FIG. 17 is a side cross-sectional view of a handle portion of the surgical instrument of FIG. 16.

In addition to the above, referring to FIG. 17, rotation knob 770 can be configured such that, when it is pulled proximally into its unlocked position as described above, locking teeth 771 can transmit the rotation of rotation knob 770 to articulation knob 760 via locking teeth 761. In at least one such embodiment, as a result, articulation knob 760 can turn synchronously with rotation knob 770 such that spine member 716 can turn synchronously with driver 739 when rotation knob 770 is in its unlocked position. In at least one embodiment, owing to the synchronous rotation of spine member 716 and driver 739, end effector 706 may not articulate relative to elongate shaft 704 when rotation knob 770 is rotated relative to handle frame 701. Stated another way, as rotation knob 770 is not being rotated relative to articulation knob 760 and driver 739 is not being rotated relative to spine 716, driver 739 may not be able to articulate end effector 706 relative to shaft 704. In any event, once end effector 706 has been properly rotated about axis 799, rotation knob 770 can be released in order to re-engage locking teeth 772 of rotation knob 770 with locking teeth 773 of handle frame 701. In at least one embodiment, referring to FIGS. 17-19, handle assembly 702 can further comprise a biasing member, such as spring 778, for example, positioned intermediate rotation knob 770 and frame 701, wherein spring 778 can be compressed between rotation knob 770 and frame 701 when rotation knob 770 is moved from its locked, distal, position into its unlocked, proximal, position and, when rotation knob 770 is released, as described above, spring 778 can bias rotation knob 770 away from frame 701 such that lock teeth 772 are re-engaged with lock teeth 773. Referring again to FIG. 19, lock teeth 772 and/or lock teeth 773 can each comprise an array of teeth which can be configured such that at least some of lock teeth 772 and 773 can intermesh, or be interlocked, regardless of the degree in which rotation knob 770 is rotated relative to frame 701. In the illustrated embodiment, lock teeth 772 and lock teeth 773 are each arranged in an annular, or at least substantially annular, and a concentric, or at least substantially concentric, array.

In various embodiments, further to the above, a surgeon can hold handle assembly 702 in one hand, such as their right hand, for example, and operate surgical instrument 700. In at least one embodiment, as outlined above, the surgeon can retract triggers 108 and 110 toward pistol grip 103 by positioning their thumb, for example, on the proximal side of pistol grip 103 and positioning one or more fingers of the same hand on the distal side of triggers 108 and 110 in order to apply a force thereto and pull them toward pistol grip 103. As also outlined above, a surgeon can extend one or more of their fingers of the same hand distally in order to grasp lip 769 of articulation knob 760 and/or lip 779 of rotation knob 770 and pull them proximally. Stated another way, a surgeon can open and close anvil 114 via closure trigger 108, incise and staple tissue via firing trigger 110, articulate end effector 706 relative to elongate shaft 704 about articulation joint 720, and, in addition, rotate end effector 706 about longitudinal axis 799 all with one hand. As a result, the surgeon can have their other hand available to perform other tasks during a surgery. In various circumstances, however, the operation of knobs 760 and 770 and triggers 108 and 110 may require a surgeon to use two hands to operate the surgical instrument, especially if the surgeon's hands are too small or are otherwise unable to perform the tasks set forth above, thereby defeating one or more possible advantages. In various alternative embodiments, referring now to FIGS. 20 and 21, a surgical instrument, such as surgical instrument 800, for example, may include a system of magnetic elements for articulating end effector 706 relative to elongate shaft 704 and, in addition, a system of magnetic elements for rotating end effector 706 about longitudinal axis 799. In various embodiments, surgical instrument 800 can further comprise additional systems of magnetic elements for moving articulation knob 760 and rotation knob 770 between their locked and unlocked positions. In any event, surgical instrument 800 can be similar to surgical instrument 700 in many respects although various differences are discussed in greater detail further below.

Figure 20:
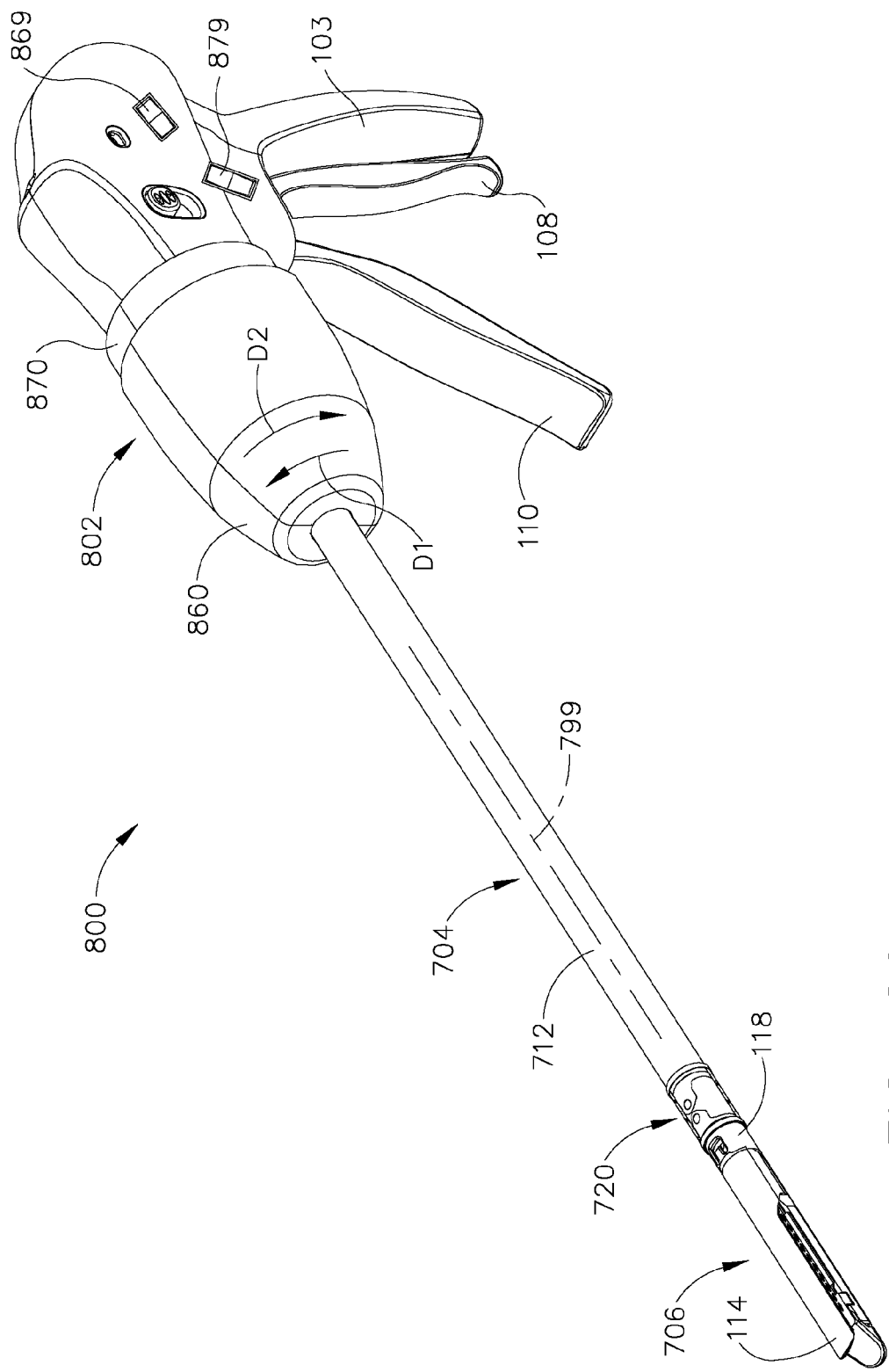
FIG. 20 is a perspective view of a surgical instrument in accordance with at least one embodiment of the present invention comprising an articulation switch and a rotation switch.
Figure 21:
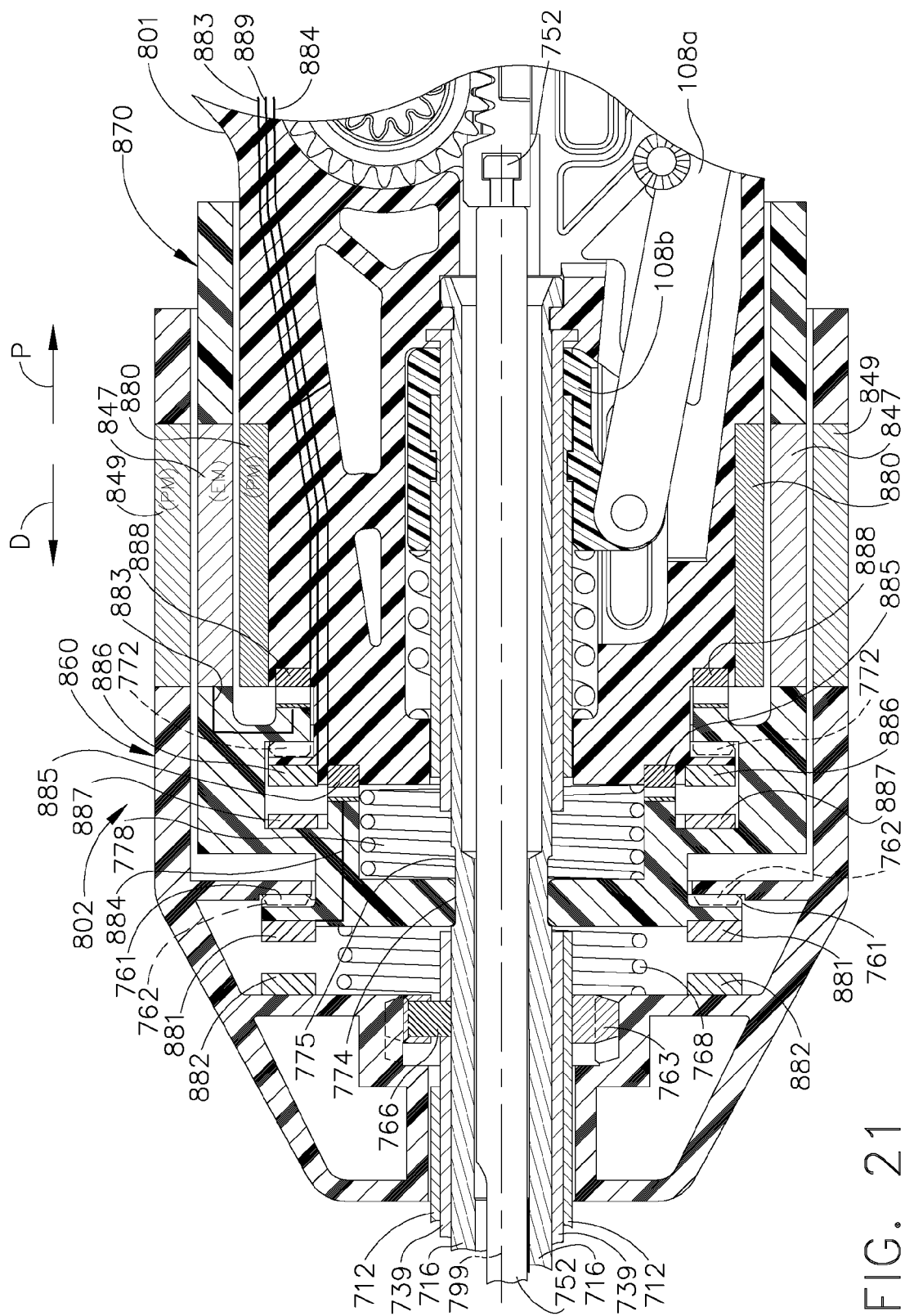
FIG. 21 is a cross-sectional view of a handle portion of the surgical instrument of FIG. 20.

Similar to articulation knob 760 of surgical instrument 700, referring now to FIG. 20, articulation knob 860 of surgical instrument 800 can be moved between a locked, distal, position and an unlocked, proximal, position. Also similar to articulation knob 760, referring to FIG. 21, articulation knob 860 can include lock teeth 761 which can be engaged and disengaged from lock teeth 762 on rotation knob 870 when articulation knob 860 is moved between its locked and unlocked positions, respectively. In various embodiments, articulation knob 860 can be pulled back, or proximally, by a system of electromagnets 881 and magnetic elements 882, for example. In at least one embodiment, referring again to FIG. 21, electromagnets 881 can be mounted to rotation knob 870 in a circular, or at least substantially circular array, which can be concentric, or at least substantially concentric, with a circular, or at least substantially circular, array of magnetic elements 882 mounted to articulation knob 860. In various embodiments, a surgeon can operate a switch on handle assembly 802, for example, in order to place a current source and/or voltage source in communication with electromagnets 881 such that electromagnets 881 can be sufficiently energized, or polarized, in order to attract magnetic elements 882 toward electromagnets 881 and, correspondingly, move articulation knob 860 proximally. In at least one such embodiment, electromagnets 881 can apply a sufficient magnetomotive force (mmf) to magnetic elements 882 in order to sufficiently displace articulation knob 860 and disengage lock teeth 761 from lock teeth 762 such that articulation knob 860 can be rotated relative to rotation knob 870, as described in greater detail further below. In various embodiments, similar to the above, a biasing member, such as spring 768, for example, can be positioned intermediate articulation knob 860 and rotation knob 870 such that spring 768 is compressed when articulation knob 860 is moved into, and held in, its proximal, unlocked position by electromagnets 881. After electromagnets 881 have been sufficiently de-energized, or de-polarized, spring 768 can be configured to bias articulation knob 860 back into its locked, distal position. In various embodiments, further to the above, magnetic elements 882 can be comprised of iron, and/or any suitable ferromagnetic material, for example, which can interact with a magnetic field. In at least some embodiments, magnetic elements 882 can comprise permanent magnets, such as neodymium magnets, samarium-cobalt magnets, and/or any suitable rare earth magnets, for example. In at least one such embodiment, magnetic elements 882 can be arranged and configured to attract, or repel, at least a portion of electromagnets 881 such that the mmf applied to electromagnets 881 can preload spring 768 and/or provide a resistive force to the proximal movement of articulation knob 860.

Once articulation knob 860 has been sufficiently unlocked, as described above, articulation knob 860 can be rotated relative to rotation knob 870 in order to articulate end effector 706 relative to elongate shaft 704. In various embodiments, articulation knob 860 can include one or more magnetic elements 849 which can be configured to interact with a magnetic field, or fields, produced by one or more electromagnets 847 mounted to rotation knob 870. In at least one such embodiment, magnetic elements 849 can be comprised of iron, and/or any other suitable ferromagnetic material, for example, and can be embedded within and/or otherwise suitably mounted to articulation knob 860. In various embodiments, electromagnets 847 can apply a magnetomotive force (mmf) to magnetic elements 849 in order to displace magnetic elements 849, and articulation knob 860, relative to electromagnets 847 and rotation knob 870. In at least one embodiment, the polarity of electromagnets 847 can be switched between first and second polarities in order to drive articulation knob 860 in a first direction indicated by arrow D1 (FIG. 20) and/or a second direction indicated by arrow D2. In use, referring to FIG. 20, a surgeon can actuate switch 869 to place a current source and/or voltage source in communication with electromagnets 847 such that electromagnets 847 can produce a magnetic field sufficient to displace articulation knob 860 relative to rotation knob 870 in a desired direction and, accordingly, articulate end effector 706 relative to elongate shaft 704 in the same manner, or an at least similar manner, as described above in connection with surgical instrument 700, for example.

Similar to rotation knob 770 of surgical instrument 700, rotation knob 870 of surgical instrument 800 can be moved between a distal position in which it is locked to frame 801 and a proximal position in which it is unlocked from frame 801. In various embodiments, further to the above, a system of electromagnets and magnetic elements, for example, can be utilized to move rotation knob 870 between its locked and unlocked positions. In at least one such embodiment, referring to FIG. 21, frame 801 can include a plurality or electromagnets 886 mounted thereto which are arranged in a circular, or at least substantially circular, array, wherein electromagnets 886 can be configured to generate a magnetic field, or fields, configured to attract and/or repel magnetic elements 887 mounted to rotation knob 870. Similar to the above, electromagnets 886 can be sufficiently energized, or polarized, in order to pull magnetic elements 887, and rotation knob 870, toward electromagnets 886 in order to disengage lock teeth 772 from lock teeth on frame 701. Once rotation knob 870 is in its unlocked position, rotation knob 870 can be rotated relative to frame 801 by another system of electromagnets and magnetic elements. In at least one such embodiment, referring again to FIG. 21, frame 801 can include a plurality of magnetic elements 880 mounted thereto which can be configured to interact with a magnetic field, or fields, produced by electromagnets 847. Similar to the above, referring to FIG. 20, a surgeon can operate a switch 879 in order to selectively energize, or polarize, magnetic elements 847 in order to produce a first magnetic field for rotating rotation knob 870 in a first direction and a second magnetic field for rotating rotation knob 870 in a second direction. In such embodiments, when rotation knob 870 is rotated, rotation knob 870 can rotate end effector 706 about longitudinal axis 799 in the same manner, or an at least similar manner, as described above in connection with surgical instrument 700, for example.

Although not illustrated, the reader will appreciate that the electromagnets of surgical instrument 800 can be powered by a common power source, such as a battery, for example, and/or different power sources. Referring once again to FIG. 21, surgical instrument 800 may further include one or more conductors, or wires, for placing the power source, or sources, in communication with the electromagnets of surgical instrument 800. In various embodiments, handle assembly 802 can further comprise one or more conductors, or wires, 883 which can supply current and/or apply voltage to electromagnets 847. In some embodiments, although not illustrated, conductors 883 can have sufficient flexibility and/or slack in order to accommodate relative movement between rotation knob 870 and frame 801. In other embodiments, referring to FIG. 21, handle assembly 802 can comprise one or more brushes 888 positioned intermediate frame 801 and rotation knob 870 which can be configured to conduct current between a power source and electromagnets 847 regardless of whether rotation knob 870 is moving relative to frame 801 and/or regardless of the degree of rotation between rotation knob 870 and frame 801. In at least one such embodiment, brushes 888 can be positioned in an annular, or at least substantially annular, array around frame 801 and rotation knob 870. In various embodiments, brushes 888 can comprise metal fiber brushes, such as braided copper brushes, for example, carbon brushes, and/or any other suitable brush. In at least one embodiment, a "brush" can comprise one or more blocks of material, such as a carbon block, for example, which can be configured to conduct current and permit relative sliding contact of an opposing "brush" across a face thereof. In certain embodiments, a "brush" can comprise any suitable compliant member. In any event, brushes 888 can be sufficiently resilient such that they can flex, or compress, when rotation knob 870 is pulled distally and re-expand when rotation knob 870 is moved back into its locked position.

In various embodiments, similar to the above, handle assembly 802 can further comprise one or more conductors, or wires, 884 which can supply current and/or apply voltage to electromagnets 881. In some embodiments, although not illustrated, conductors 884 can have sufficient flexibility and/or slack in order to accommodate relative movement between rotation knob 870 and frame 801. In other embodiments, similar to the above, handle assembly 802 can comprise one or more brushes 885 positioned intermediate rotation knob 870 and frame 801 which can be configured to conduct current between a power source and electromagnets 881 regardless of whether rotation knob 860 is moving relative to frame 801 and/or regardless of the degree of rotation between rotation knob 870 and frame 801. Similar to the above, brushes 885 comprise metal fiber brushes, such as braided copper brushes, for example, carbon brushes, and/or any other suitable brush which can be sufficiently resilient such that they can flex, or compress, when rotation knob 870 is pulled distally and re-expand when rotation knob 870 is moved back into its locked position. In addition to the above, brushes 885, and/or brushes 888, can permit relative sliding movement between two halves of the brush. More particularly, in at least one embodiment, a brush 885, for example, can comprise a first half mounted to rotation knob 870 having bristles extending therefrom, wherein the second half of brush 885 can comprise a contact plate, or plates, mounted to frame 801 against which the bristles can contact and slide thereover. In other various embodiments, a brush 885, for example, can comprise first and second halves each having bristles extending therefrom, wherein the first and second halves can be mounted to rotation knob 870 and frame 801 and can contact and slide over one another. In any event, brushes 885 can be positioned in an annular, or at least substantially annular, array around frame 801 and rotation knob 870. In various embodiments, referring once again to FIG. 21, handle assembly 802 can include one or more conductors, or wires, 889 which can supply current and/or apply voltage to electromagnets 886.

Figure 22:
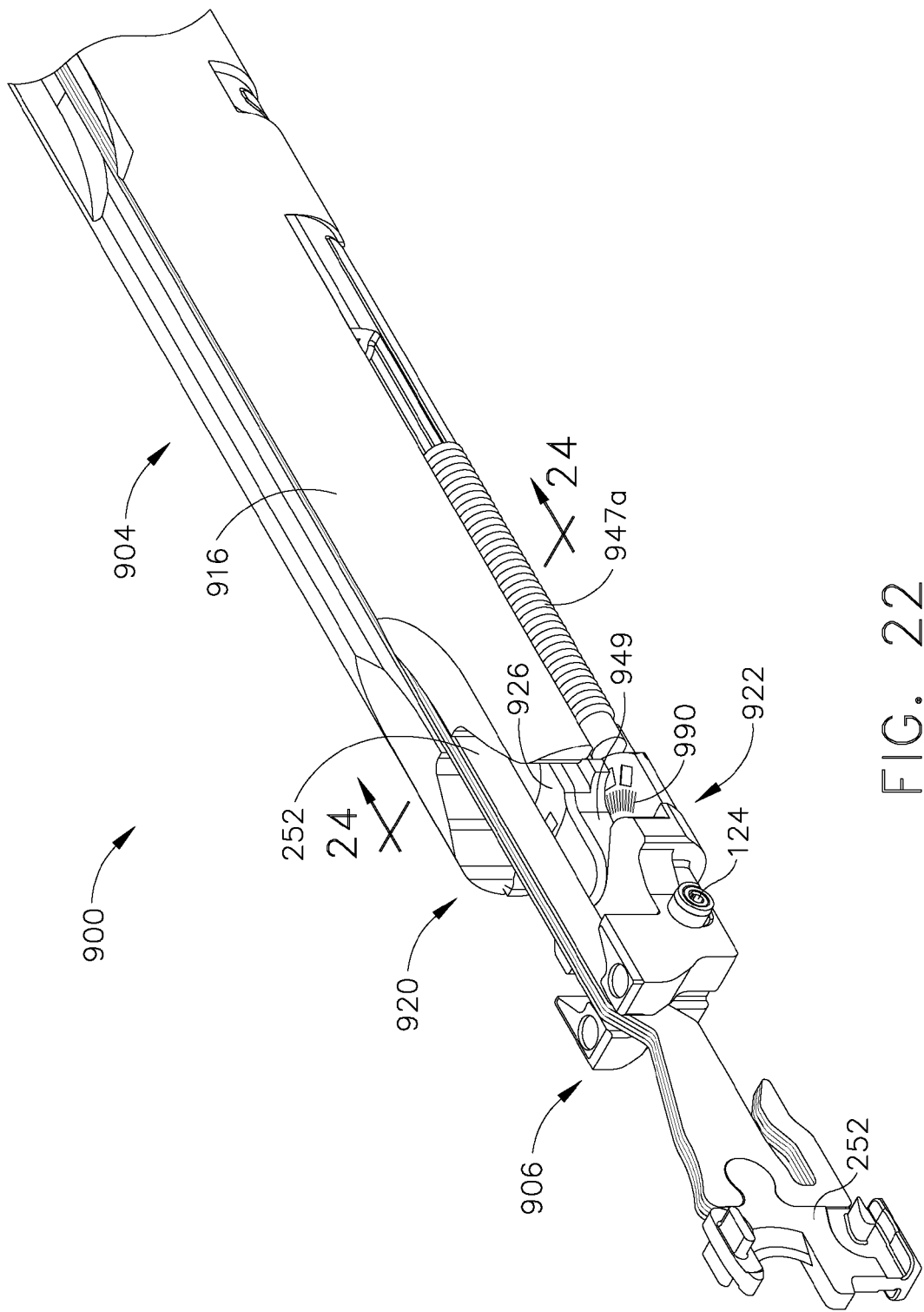
FIG. 22 is a perspective view of an articulation joint connecting an end effector and an elongate shaft of a surgical instrument in accordance with at least one embodiment of the present invention illustrated with some components removed.

In various embodiments, a surgical instrument can include one or more electromagnets positioned within an elongate shaft, wherein the electromagnets can be configured to articulate an end effector of the surgical instrument relative to the elongate shaft. In at least one embodiment, referring to FIGS. 22-24, surgical instrument 900 can comprise an elongate shaft 904 and an end effector 906 (shown with portions removed), wherein end effector 906 can be pivotably connected to elongate shaft 904 by articulation joint 920. Similar to the above, end effector 906 can comprise a pivot plate 922 and, in addition, elongate shaft 904 can comprise a pin insert plate 926 which can be secured within elongate shaft 904 by spine 916. Also similar to the above, pin insert plate 926 can include a pin extending therefrom which can be configured to be closely received within pin aperture 123 in pivot plate 922. In certain embodiments, referring primarily to FIG. 23, elongate shaft 904 can further comprise electromagnets 940a and 940b mounted therein and, in addition, pivot plate 922 can further comprise magnetic elements 949 mounted thereto wherein electromagnets 940a, 940b can be configured to generate a magnetic field, or fields, which can be configured to interact with magnetic elements 949 and rotate pivot plate 922, and end effector 906, about an axis defined by pin insert plate 926. In various embodiments, magnetic elements 949 can comprise magnets, such as rare earth magnets, for example, which can be positioned and arranged on pivot plate 922 such that the poles of the magnets are aligned in a predetermined orientation. In at least one embodiment, magnetic elements 949 can be arranged such that the poles of each magnet are arranged in an end-to-end configuration such that the positive, or north, pole of each magnet is positioned next to the negative, or south, pole of the adjacent magnet, for example. Other embodiments are envisioned in which the positive poles of magnets 949 are positioned radially outwardly with respect to their negative poles, for example.

In use, in at least one embodiment, electromagnet 940b, for example, can be energized, or polarized, such that the distal end of electromagnet 940b comprises a positive, or north, magnetic pole of a magnetic field. In such circumstances, the positive poles of magnetic elements 949 can be repulsed away from electromagnet 940b and the negative poles of magnetic elements 949 can be attracted toward electromagnet 940b. In various embodiments, as a result, the magnetic field produced by electromagnet 940b, for example, can be sufficient to displace, or rotate, pivot plate 922, and end effector 906, in a counter-clockwise direction indicated by arrow CCW, for example. In at least one such embodiment, referring to FIG. 23, the intensity of the magnetic field produced by electromagnet 940b can be controlled by controlling the magnitude of current flowing through conductor 947b, wherein a larger current can produce a more intense magnetic field and a smaller current can produce a less intense magnetic field. In certain embodiments, similar to the above, the direction in which current is supplied, or the polarity in which voltage is applied, to conductor 947b can control the polarity of the magnetic pole generated at the distal end of electromagnet 940b. More particularly, if the current flowing through conductor 947b is flowing in a first direction, the current can generate a positive pole at the distal end of core 941b whereas, if the current flowing through conductor 947b flows in the opposite direction, the current can generate a negative pole at the distal end of core 941b. In various embodiments, as a result, the direction of the current flowing through conductor 947b can be selectively changed in order to selectively change the polarity of the magnetic field produced by electromagnet 940b, for example. In at least one such embodiment, the initial polarity of the distal end of electromagnet 940b can be positive, for example, in order to repel a first magnet 949 wherein the polarity of the distal end of electromagnet 940b can then be changed from positive to negative so as to draw the next permanent magnet 949 toward electromagnet 940b in order to continue to rotate pivot plate 922 and end effector 906. Once the second permanent magnet 949 has been sufficiently positioned, the polarity of electromagnet 940b can be switched once again, i.e., from negative to positive, and repel the second electromagnet 949 away from electromagnet 940b and, again, continue to rotate pivot plate 922 and end effector 906.

In various embodiments, it may be desirable to limit the range in which end effector 906 can be rotated relative to elongate shaft 904. In certain embodiments, although not illustrated, elongate shaft 904 can include one or more stops which can be configured to stop the rotation of end effector 906 when it is moved in a clockwise direction and/or a counter-clockwise direction. In at least one such embodiment, the stops can limit the maximum rotation of end effector 906 in the clockwise and/or counter-clockwise directions. In some embodiments, referring to FIG. 23, a surgical instrument can further comprise means for detecting the position, or relative angle, between end effector 906 and elongate shaft 904 and, in addition, means for stopping the rotation of end effector 906 once end effector 906 has been sufficiently displaced. In at least one such embodiment, elongate shaft 904 can further include one or more sensors which can be configured to detect one or more markings on end effector 906 in order to determine the amount, or degree, in which end effector 906 has been rotated relative to shaft 904. More particularly, in at least one embodiment, elongate shaft 904 can further comprise at least one photosensor, such as photosensor 991, for example, which can be configured to detect encoder markings 990 as they pass under photosensor 991 when end effector 906 is rotated. In various embodiments, photosensor 991 can further comprise a light emitter and, in addition, encoder markings 990 can comprise at least partially reflective surfaces on pivot plate 922 which can be configured to reflect light produced by the light emitter in order to facilitate the detection of encoder markings 990. In certain embodiments, encoder markings 990 can be etched into a surface on pivot plate 922. In at least one embodiment, although not illustrated, end effector 906 can comprise a plurality of slits, or apertures, arranged in a suitable array similar to the arrangement of encoder markings 990, wherein the apertures can be configured to allow light to pass therethrough from a light source positioned on the opposite, or bottom, side of pivot plate 922. In at least one such embodiment, the light source can comprise one or more light emitting diodes. In certain other embodiments, although not illustrated, an end effector and elongate shaft can comprise a mechanical encoder which is indexed as the end effector is rotated.

Figure 23:
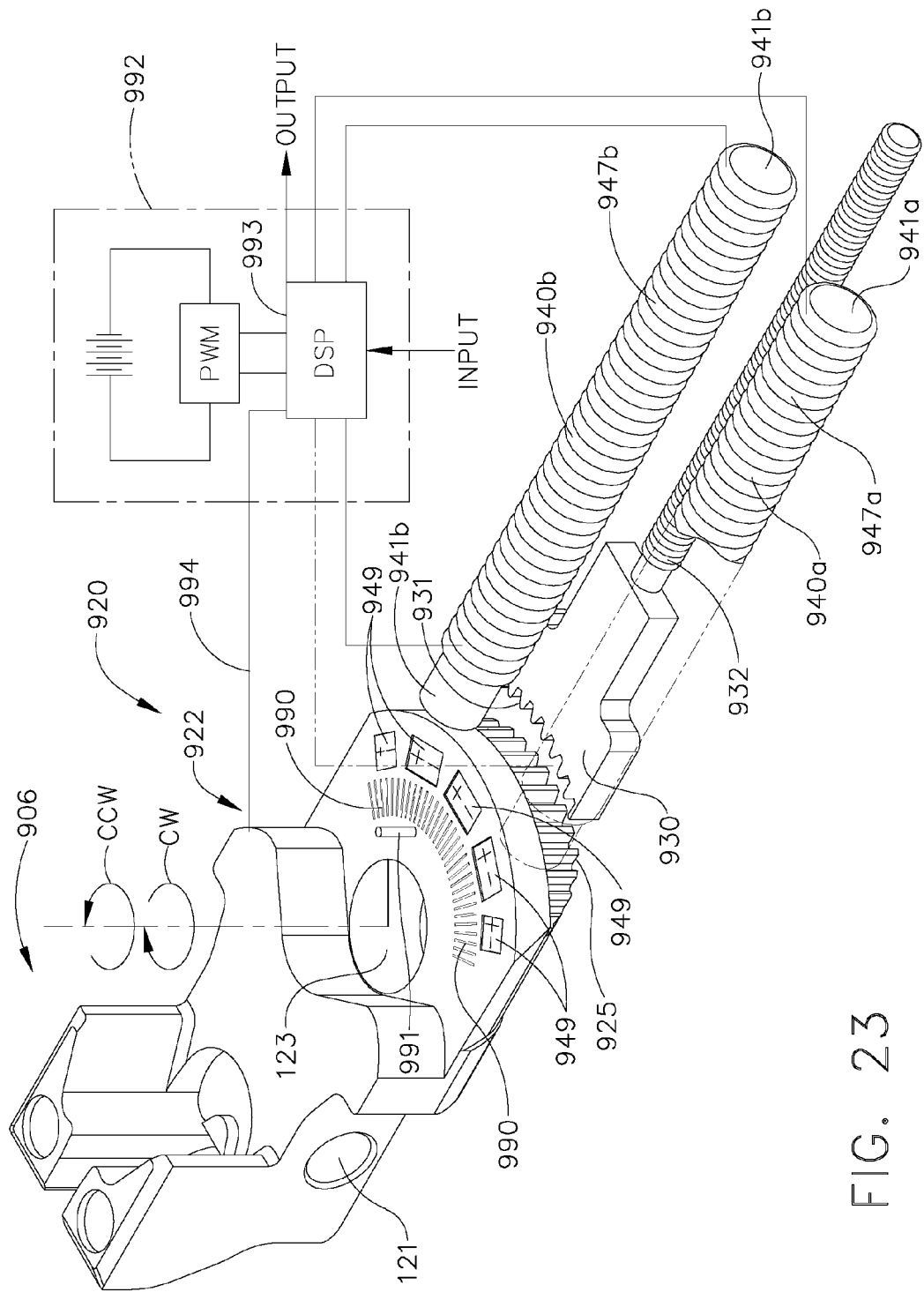
FIG. 23 is a schematic illustrating electromagnets positioned within the elongate shaft of FIG. 22 configured to apply a magnetic force to permanent magnets mounted to the end effector of FIG. 22.
Figure 24:
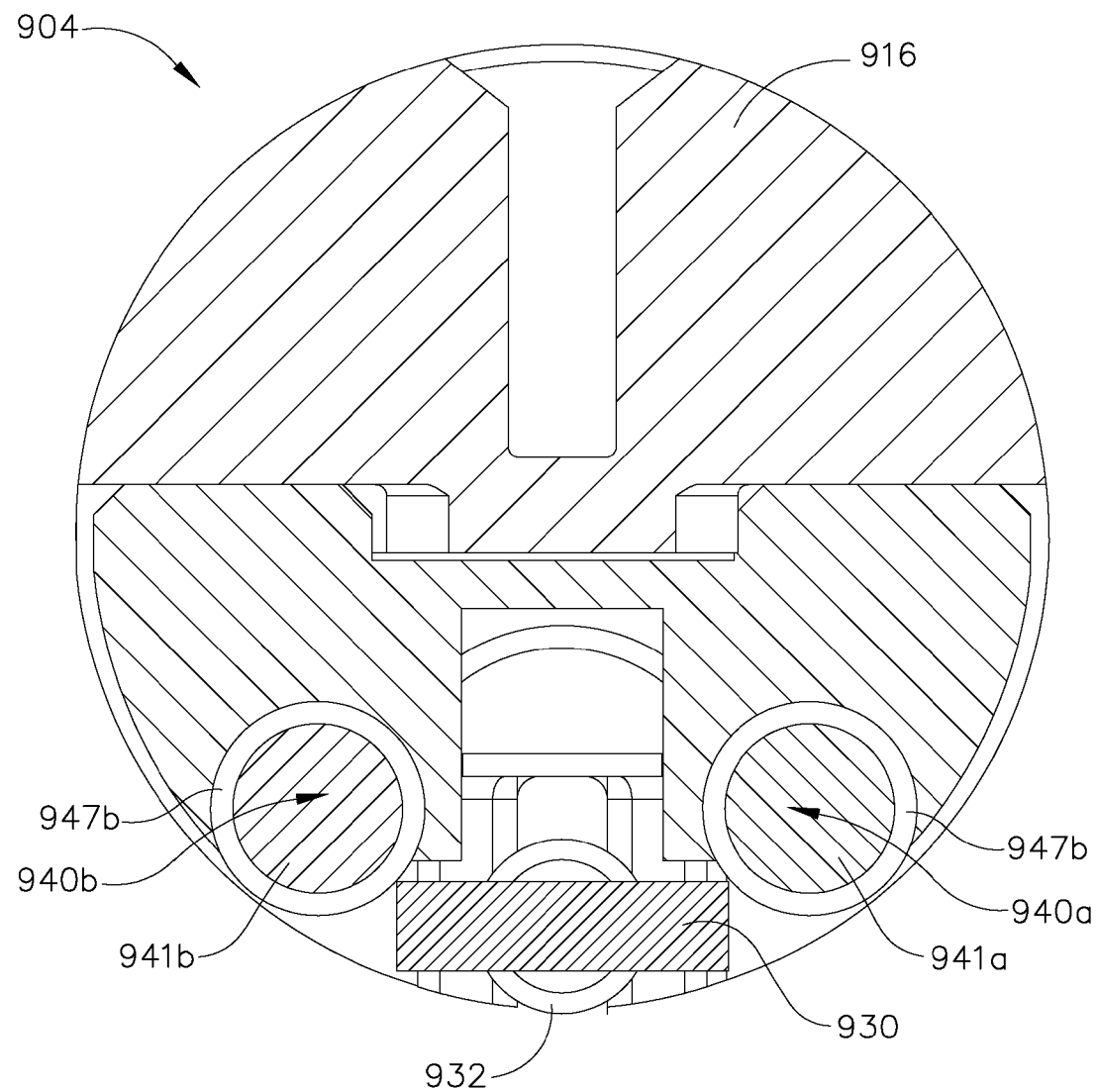
FIG. 24 is a cross-sectional view of the elongate shaft of FIG. 22.

In various embodiments, referring primarily to FIG. 23, photosensor 991, for example, can be placed in signal communication with a control unit, such as control unit 992, for example, such that data regarding the number of encoder markings 990 that pass under photosensor 991 can be transmitted to control unit 992. More particularly, in at least one embodiment, control unit 992 can comprise at least one digital signal processor, such as DSP 993, for example, which can be configured to receive signal pulses from photosensor 991 which correspond to the passing of encoder markings 990 under photosensor 991. For example, if five markings 990 pass under sensor 991, sensor 991 can transmit five signal pulses to DSP 993 via conductor 994, although such communication can be wireless via a wireless transmitter (not illustrated). In any event, DSP 993 can be configured to process such signal pulses, calculate the amount in which end effector 906 has rotated relative to end effector 904, and output such information to the surgeon. In at least one embodiment, further to the above, the detection of one encoder marking 990 can represent one degree of articulation of end effector 906, wherein DSP 993 can be configured to transmit the degree in which end effector 906 has been rotated to an LCD display on the handle assembly of the surgical instrument. In various embodiments, the LCD display can comprise a screen, wherein data can be displayed in the form of numerals, text, and/or a graphical form such as an increasing or decreasing bar scale, for example. In various embodiments, further to the above, control unit 992 can further include a pulse width modulator (PWM) which can be configured to modify and control the output signals or power supplied to electromagnets 940a and 940b.

Figure 25:
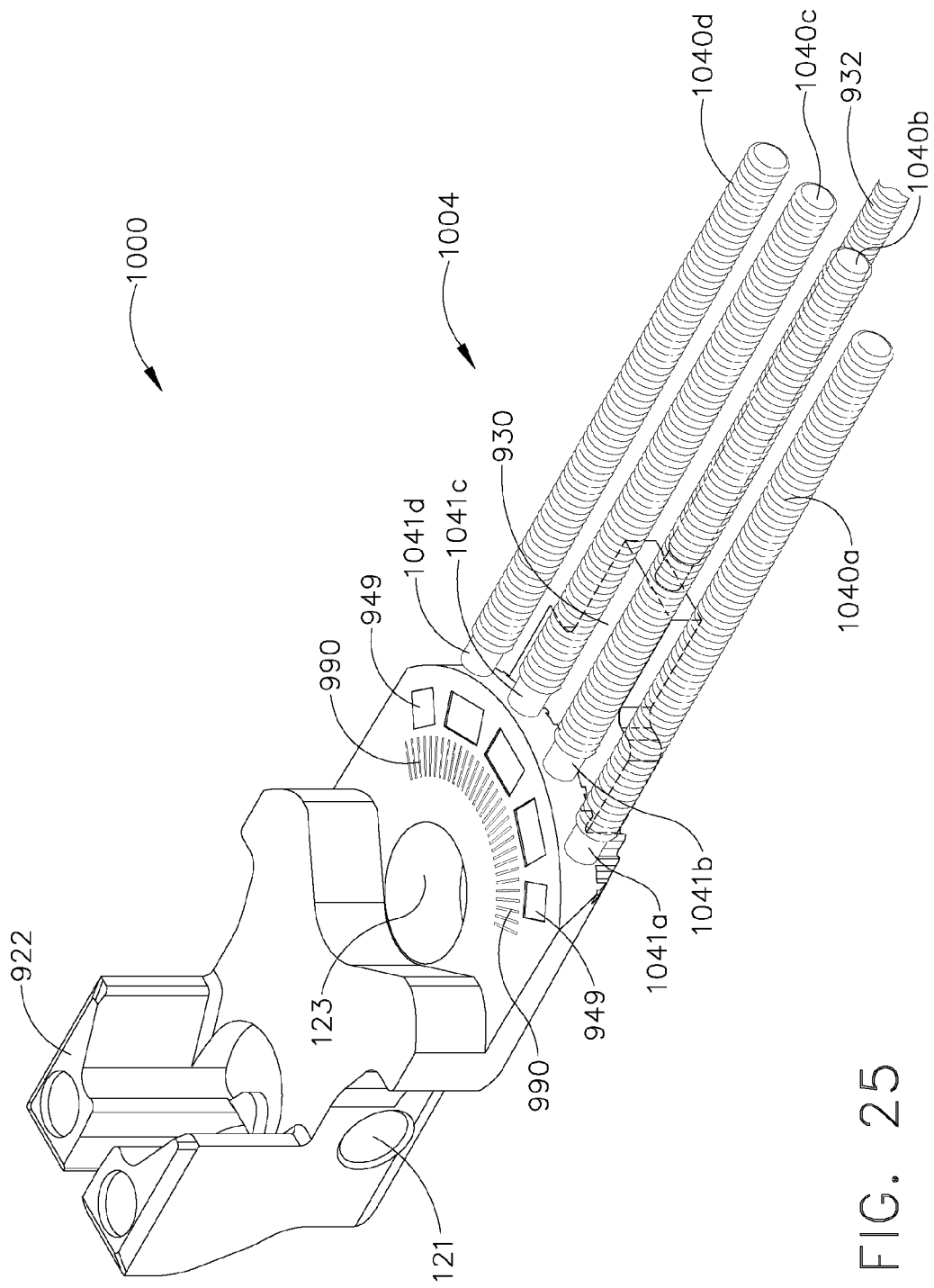
FIG. 25 is a perspective view of an articulation joint connecting an end effector and an elongate shaft of a surgical instrument in accordance with at least one embodiment of the present invention with some components removed.
Figure 26:
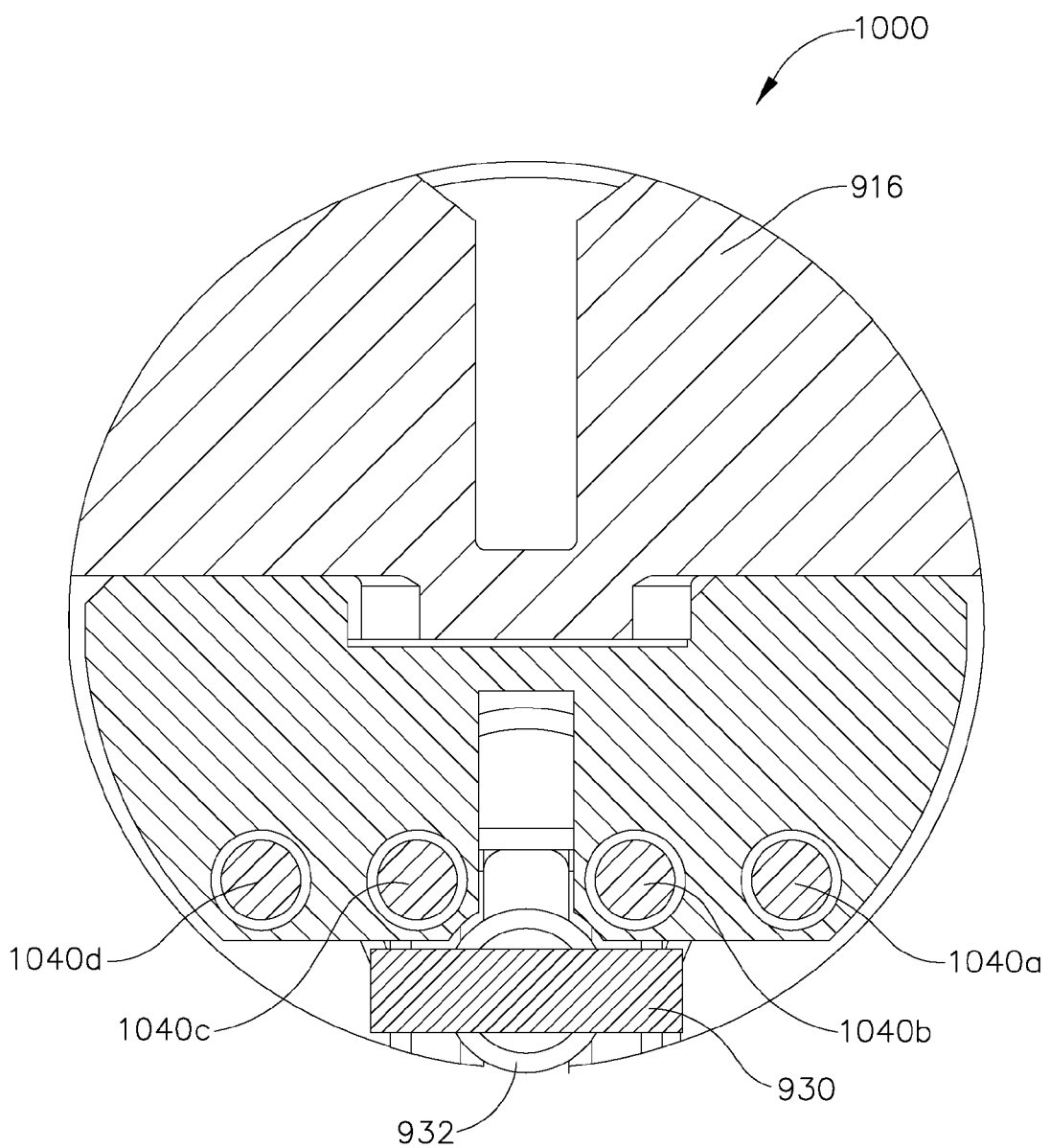
FIG. 26 is a cross-sectional view of the end effector of FIG. 25 illustrating a plurality of electromagnets.
Figure 27:
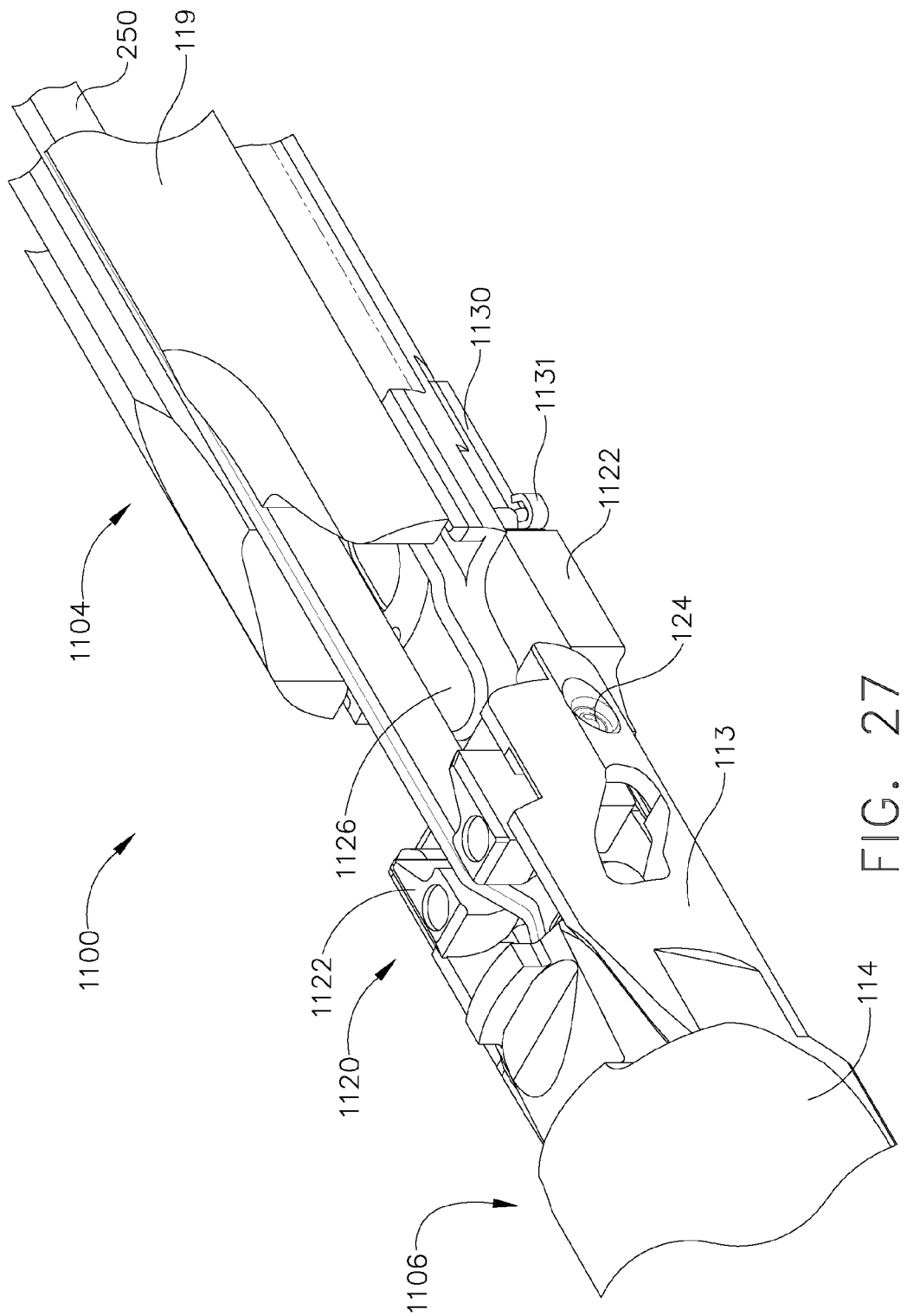
FIG. 27 is a perspective view of an articulation joint connecting an end effector and an elongate shaft of a surgical instrument in accordance with at least one embodiment of the present invention illustrated with some components removed.
Figure 28:
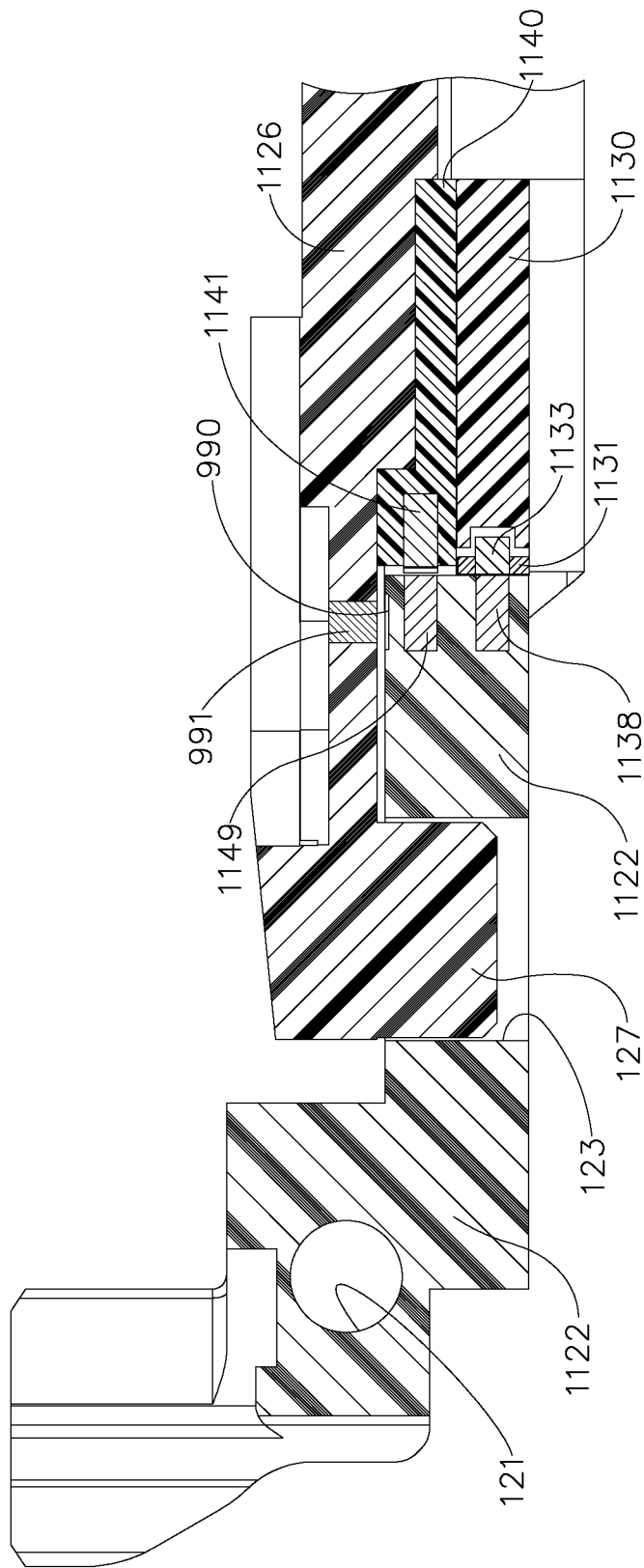
FIG. 28 is a cross-sectional view of the articulation joint of FIG. 27 illustrating a system of permanent magnets and electromagnets configured to articulate the end effector of the surgical instrument and another system of permanent magnets and electromagnets configured to lock the end effector in position relative to the elongate shaft of the surgical instrument.
Figure 29:
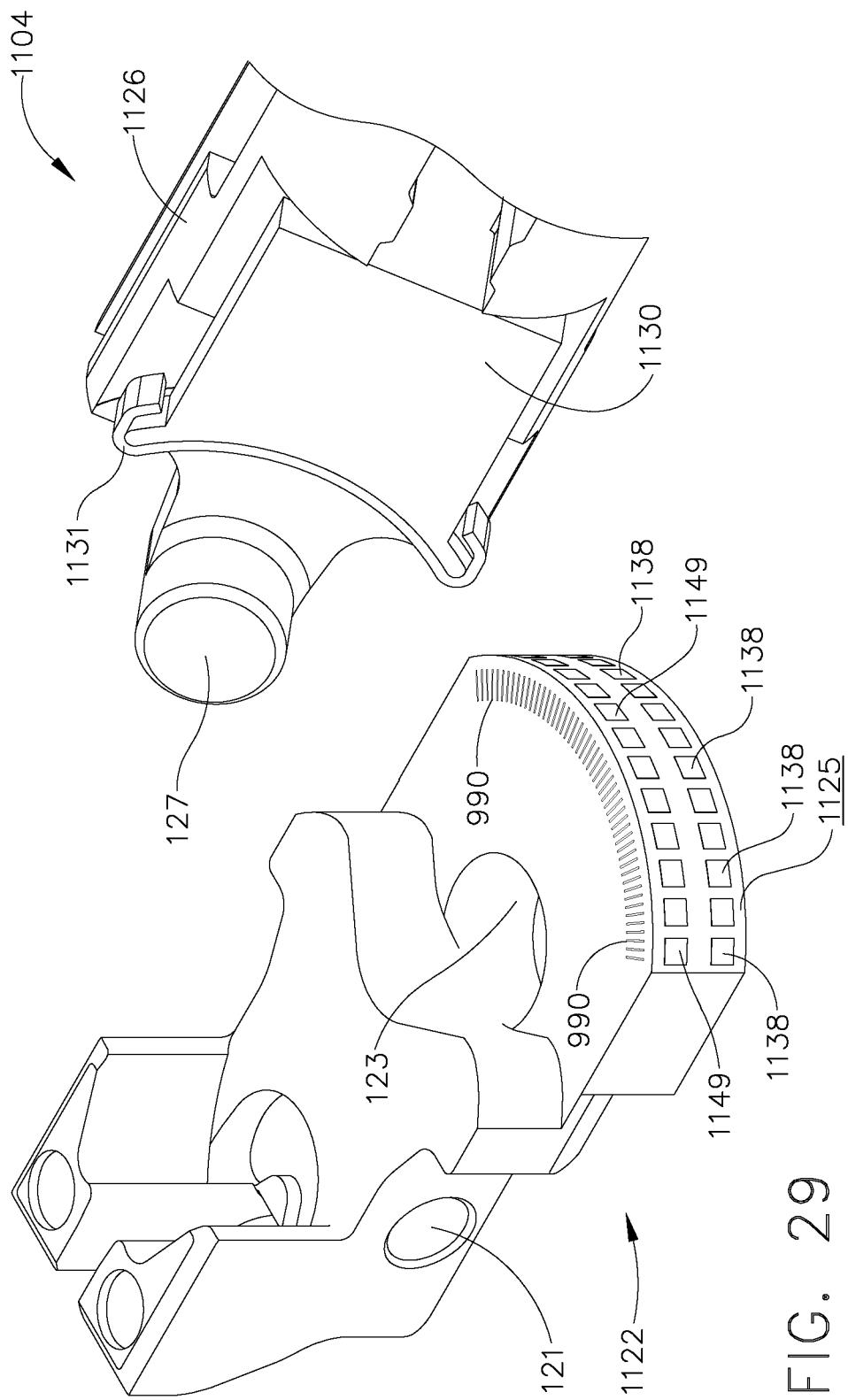
FIG. 29 is a disassembled view of the articulation joint of FIG. 27 illustrated with some components removed.
Figure 30:
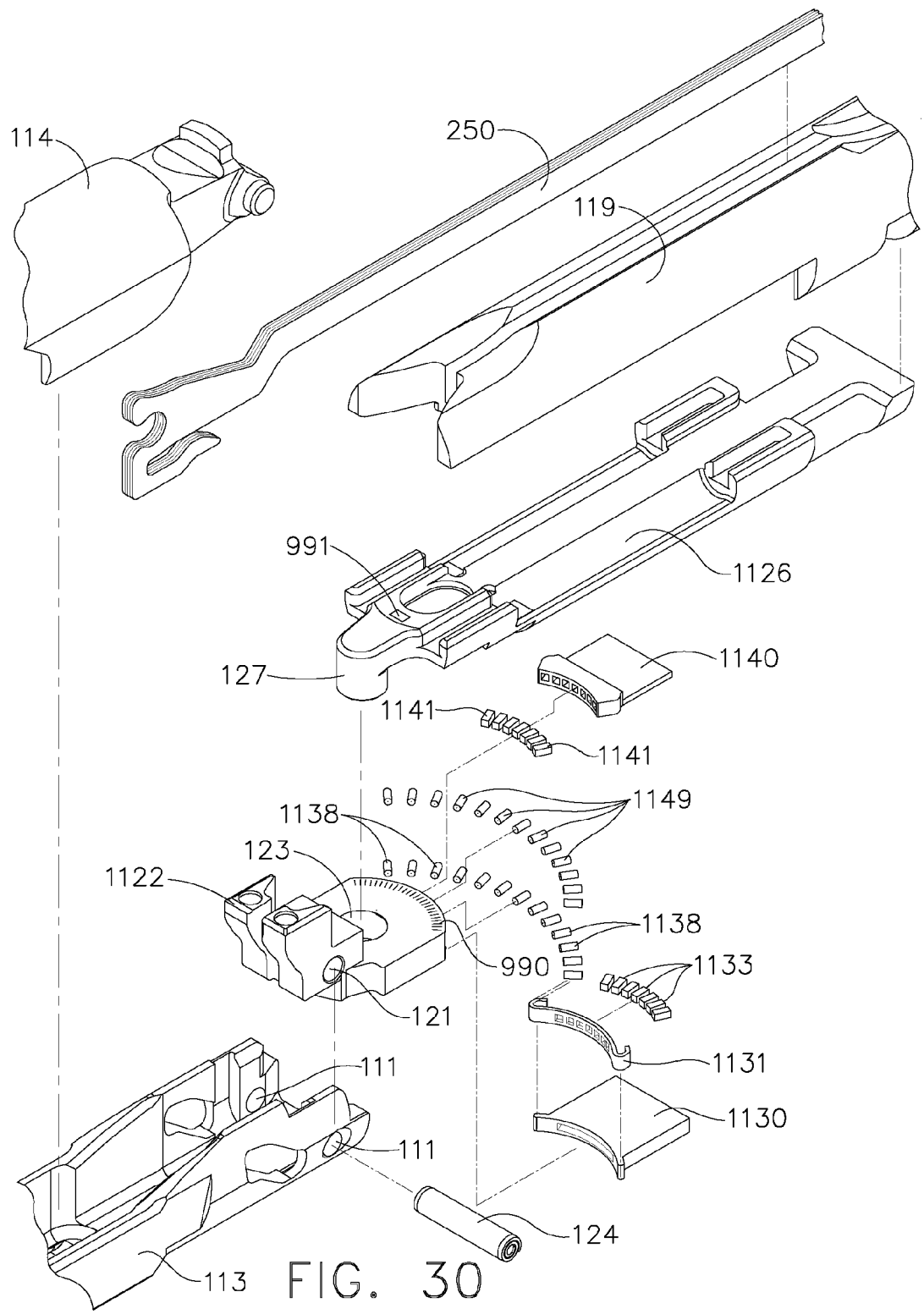
FIG. 30 is an exploded view of the articulation joint of FIG. 27.
Figure 31:
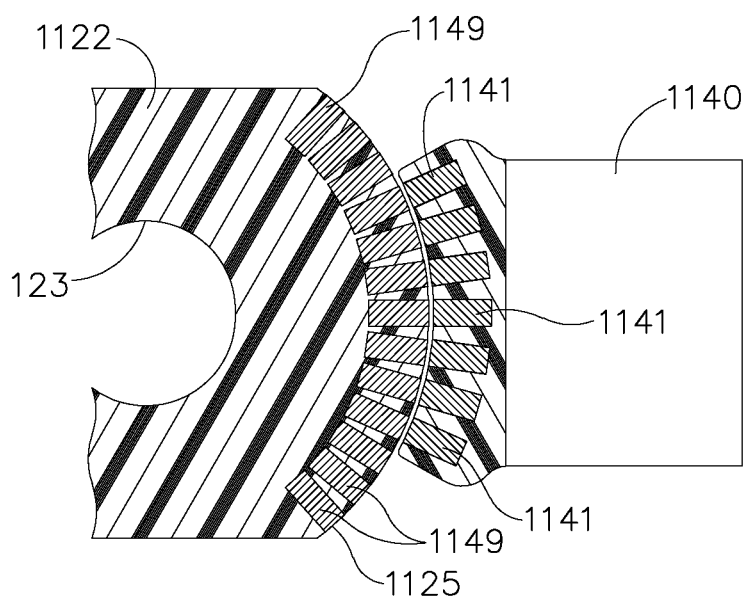
FIG. 31 is a cross-sectional view of the articulation joint of FIG. 27 illustrating the system of permanent magnets and electromagnets for articulating the end effector of the surgical instrument.
Figure 32:
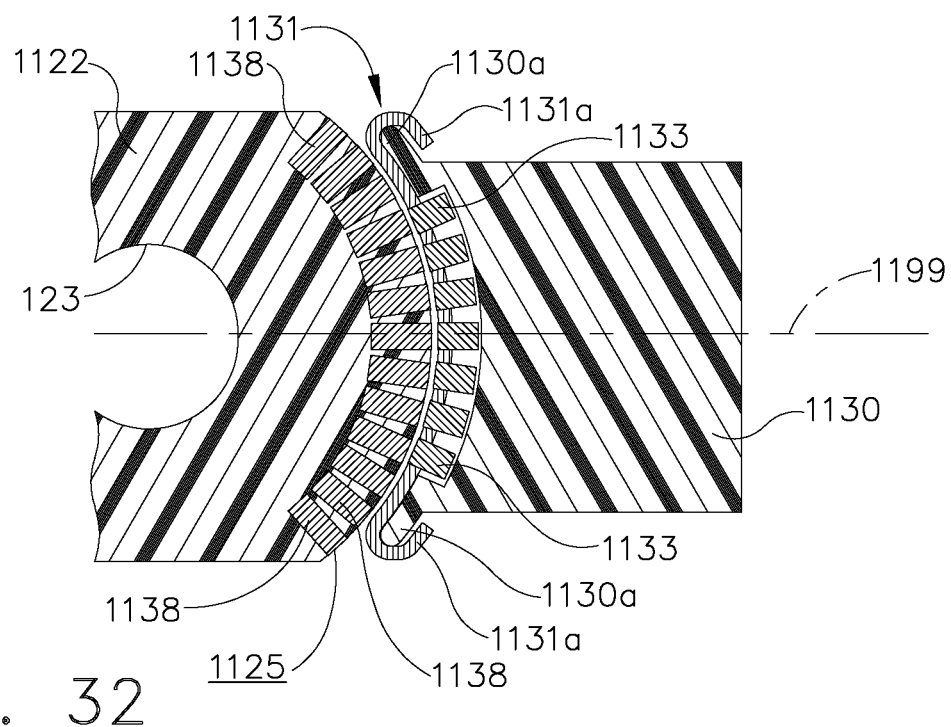
FIG. 32 is a cross-sectional view of the articulation joint of FIG. 27 illustrating the system of permanent magnets and electromagnets for locking the end effector in position.

As described above, elongate shaft 904 can comprise two electromagnets, i.e., electromagnets 940a and 940b, which can be configured to emit a magnetic field, or fields, which can interact with magnetic elements 949. As illustrated in FIG. 23, pivot plate 922 includes five magnetic elements 949 embedded therein; however, other embodiments may have less than five magnetic elements 949 or more than five magnetic elements. Similarly, other surgical instruments can comprise any suitable number of electromagnets. In at least one embodiment, referring now to FIG. 25, an elongate shaft 1004 of surgical instrument 1000 can comprise four electromagnets, i.e., electromagnets 1040a, 1040b, 1040c, and 1040d which can each be configured to independently generate a magnetic field and polarity at the distal ends of cores 1041a-1041d, respectively. Similar to the above, the strength and polarity of the magnetic fields produced by electromagnets 1040a-1040d can be determined by the direction and magnitude of the current flowing through conductors, or wires, 1041a-1041d, respectively. In any event, once end effector 906 has been sufficiently articulated, similar to the above, end effector 106 can be locked into position. In various embodiments, referring to FIG. 23, elongate shaft 904 can further comprise lock 930 which can be moved between a proximal, unlocked position and a distal, locked position in which lock 930 is engaged with teeth 925 on pivot plate 922. In at least one embodiment, lock 930 can include a plurality of recesses 931 which can be configured to receive one or more teeth 925 such that pivot plate 922 cannot rotate, or at least substantially rotate, relative to lock 930 and, correspondingly, elongate shaft 904. Similarly, lock 930 can comprise a plurality of teeth positioned intermediate recesses 931 which can be configured to be received within recesses positioned intermediate teeth 925 on pivot plate 922, for example. In various embodiments, also similar to the above, elongate shaft 904 can further comprise lock actuator 932 which can be configured to move lock 930 between its locked and unlocked positions. In at least one such embodiment, lock actuator 932 can comprise a solenoid, for example.

In various embodiments, referring now to FIGS. 27-32, a surgical instrument, such as surgical instrument 1100, for example, can comprise an elongate shaft 1104 and an end effector 1106, wherein end effector 1106 can be configured to articulate relative to elongate shaft 1104 about articulation joint 1120. In at least one embodiment, similar to the above, end effector 1106 can comprise pivot plate 1122 mounted thereto and, in addition, elongate shaft 1104 can comprise pin plate member 1126 mounted therein, wherein pin 127 extending from pin plate member 1126 can be closely received within pin aperture 123 in pivot plate 1122 in order to define an axis about which pivot plate 1122, and end effector 1106, can articulate relative to elongate shaft 1104. Also similar to the above, elongate shaft 1104 can further comprise one or more electromagnets which can be configured to generate a magnetic field, or fields, which can be configured to interact with one or more magnetic elements mounted to end effector 1106. In at least one such embodiment, referring primarily to FIGS. 28-31, pivot plate 1122 of end effector 1106 can have a plurality of permanent magnets 1149 mounted thereto wherein, in at least one embodiment, permanent magnets 1149 can be embedded within one or more cavities within pivot plate 1122. In certain embodiments, similar to the above, permanent magnets 1149 can have positive and negative poles which can be arranged in a suitable manner such that, when electromagnets 1141 mounted within elongate shaft 1104 are sufficiently energized, or polarized, permanent magnets 1149 can interact with the magnetic field, or fields, generated by electromagnets 1141. In at least one such embodiment, the positive poles of permanent magnets 1149 can be arranged such that their positive poles are positioned radially outwardly with respect to their negative poles. Stated another way, in at least one embodiment, the positive poles of permanent magnets 1149 can be positioned adjacent to surface 1125 whereas the negative poles of magnets 1149 can be positioned distally, or at least somewhat distally, with respect to the positive poles. In certain other embodiments, permanent magnets 1141 can be arranged such that their poles alternate. For example, permanent magnets 1141 can be arranged such that the radially outward end of a first magnet 1141 is positive, for example, the radially outward end of a second magnet 1141 is negative, and the radially outward end of a third magnet is positive, and so forth.

In various embodiments, further to the above, electromagnets 1141 can be selectively energized, or polarized, in order to retract or repel permanent magnets 1149 and rotate end effector 1106 in a desired direction. In certain embodiments, referring to FIGS. 28 and 30, electromagnets 1141 can be embedded in or positioned within one or more cavities in actuator member 1140. In at least one embodiment, a first group of electromagnets 1141 can be energized, or polarized, such that their distal ends, i.e., their ends positioned adjacent to permanent magnets 1149, generate negative poles, for example, while a second group of electromagnets 1141 can remain unenergized, or unpolarized, or at least substantially unenergized, or unpolarized. In at least one such embodiment, as a result, the negative polarity of the distal ends of electromagnets 1141 can attract the positive poles of permanent magnets 1149 and move permanent magnets 1149 toward the negative poles electromagnets 1141. In various circumstances, the selective energization, or polarization, of the first group of electromagnets 1141 can displace permanent magnets 1149 such that end effector 1106 is rotated in a counter-clockwise direction, for example. In certain circumstances, the first group of electromagnets 1141 can be subsequently de-energized, or de-polarized, or at least substantially de-energized, or de-polarized, and the second group of electromagnets 1141 can be energized, or polarized, such that their distal ends generate a negative polarity which, similar to the above, attracts the positive poles of permanent magnets 1149 in order to continue the rotation of end effector 1106 in a counter-clockwise direction, for example. In certain other embodiments, the first group of electromagnets 1141 can be energized such that their distal ends generate a negative polarity, for example, while the second group of electromagnets 1141 can be energized such that their distal ends generate a positive polarity, for example. In various embodiments, the first and second groups can be energized such that they have different polarities simultaneously or in a suitable alternating sequence.

Once end effector 1106 has been sufficiently articulated, further to the above, end effector 1106 can be locked into position. In various embodiments, referring to FIGS. 28-30 and 32, elongate shaft 1104 can further comprise lock 1130, wherein at least a portion of lock 1130 can be moved between a distal, locked position, in which it is engaged with pivot plate 1122, for example, and a proximal, unlocked position in which it is sufficiently disengaged from pivot plate 1122 to allow end effector 1106 to rotate about an axis defined by pin aperture 123 and pin 127. In at least one embodiment, lock 1130 can comprise a movable brake shoe, such as brake shoe 1131, for example, which can be moved between proximal and distal positions. More particularly, in at least one embodiment, pivot plate 1122 can include one or more permanent magnets 1138 mounted thereto, wherein permanent magnets 1138 can be configured and arranged such that their positive, or north, poles, for example, are positioned radially outwardly with respect to their negative, or south, poles, and wherein permanent magnets 1138 can be configured to attract brake shoe 1131 toward pivot plate 1122 such that brake shoe 1131 contacts brake surface 1125. In various embodiments, brake shoe 1131 can include one or more magnetic elements 1133 mounted thereto which can interact with the magnetic field, or fields, produced by permanent magnets 1138, wherein the magnetic field, or fields, can apply a sufficient magnetomotive force (mmf) to magnetic elements 1133 such that the bearing force, or braking force, between brake shoe 1131 and brake surface 1125 is sufficient to prevent, or at least inhibit, relative movement between pivot plate 1122 and pivot pin member 1126.

In order to disengage brake shoe 1131 from pivot plate 1122, in various embodiments, magnetic elements 1133 can comprise electromagnets which can be selectively energized to order to create a magnetic field, or fields, which can move brake shoe 1131 away from pivot plate 1122. In at least one circumstance, electromagnets 1133 can be energized in order to generate positive poles at their distal ends, i.e., their ends closest to pivot plate 122, such that the positive poles generated by electromagnets 1133 are repelled by the positive poles of permanent magnets 1138. In various embodiments, electromagnets 1133 can be mounted to brake shoe 1131 such that, when a sufficient magnetomotive force is generated, brake shoe 1131 can be displaced proximally. Brake shoe 1131 can be displaced proximally such that brake shoe 1131 is no longer engaged with brake surface 1125 and/or such that brake shoe 1131 is otherwise unable to apply a sufficient braking force to pivot plate 1122 in order to hold end effector 1106 in position. In certain other embodiments, the negative poles of permanent magnets 1138 can be positioned radially outwardly such that, when electromagnets 1133 are energized, negative poles generated at the distal ends of electromagnets 1133 can be repelled by the negative poles of permanent magnets 1138. In at least one embodiment, referring primarily to FIGS. 29 and 32, lock 1130 can comprise one or more features for limiting the displacement of brake shoe 1131 such that brake shoe 1131 travels along a predetermined path, such as axis 1199, for example. In at least one such embodiment, lock 1130 can further comprise one or more projections, or travel limiters 1130a, and brake shoe 1131 can further comprise stop arms 1131a, wherein travel limiters 1130a and stop arms 1131a can be configured to prevent, or at least inhibit, relative movement between brake shoe 1131 and lock 1130 which is transverse to axis 1199.

Figure 38:
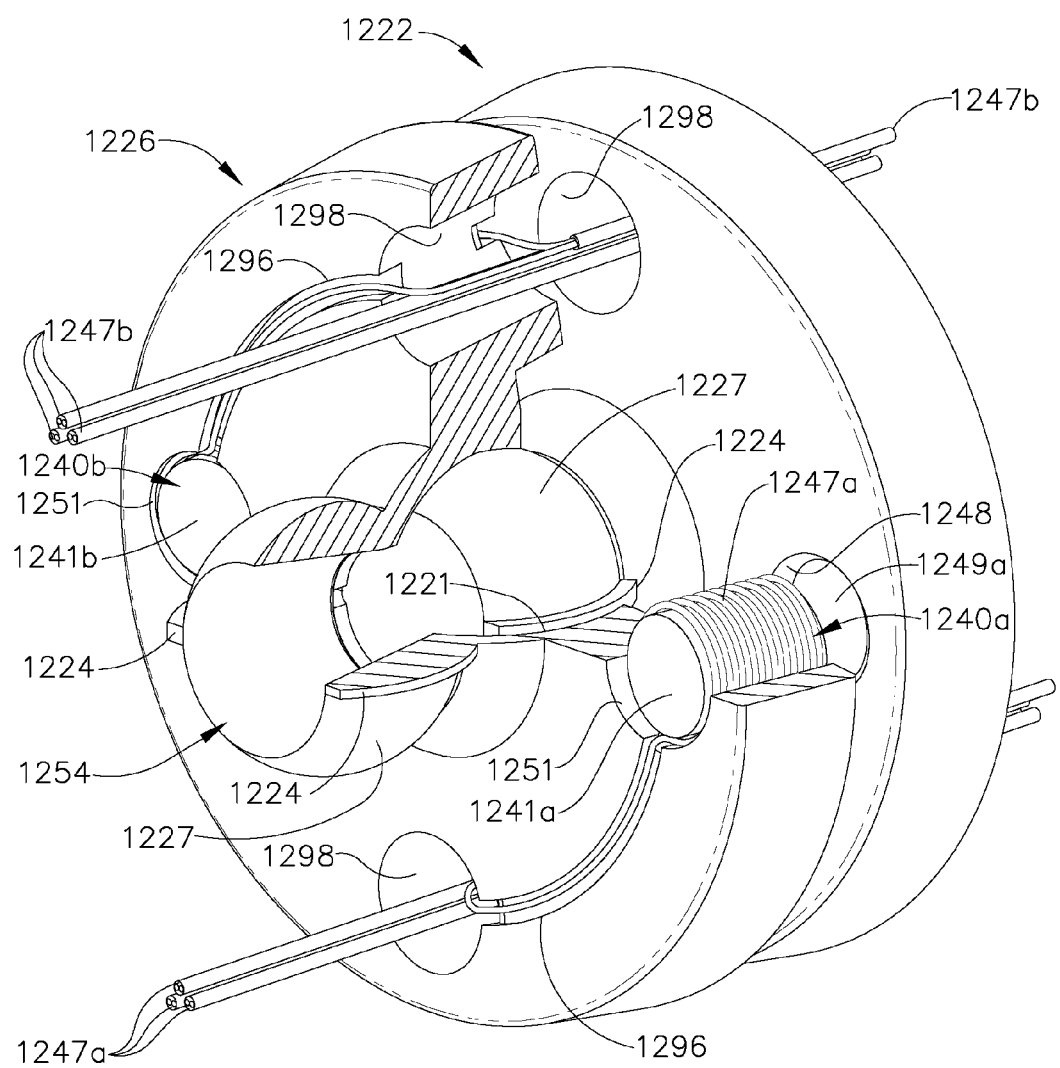
FIG. 38 is an assembly view of the disc of FIG. 36 and a second disc positioned adjacent thereto, wherein the second disc comprises a plurality of permanent magnets positioned within a first set of apertures and another set of apertures configured to permit the wires of FIG. 36 to extend therethrough.
Figure 39:
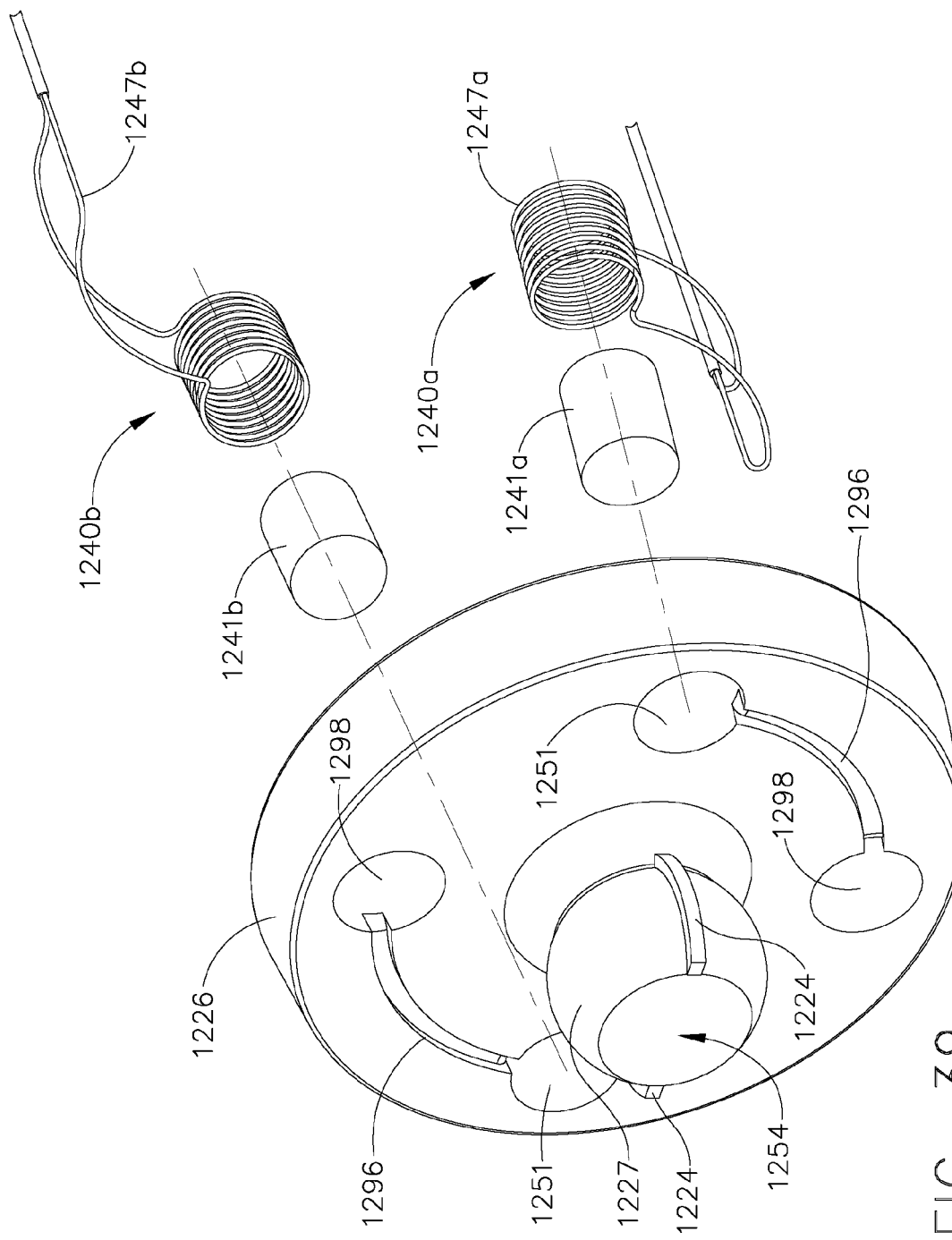
FIG. 39 is an exploded view of the disc of FIG. 36.
Figure 40:
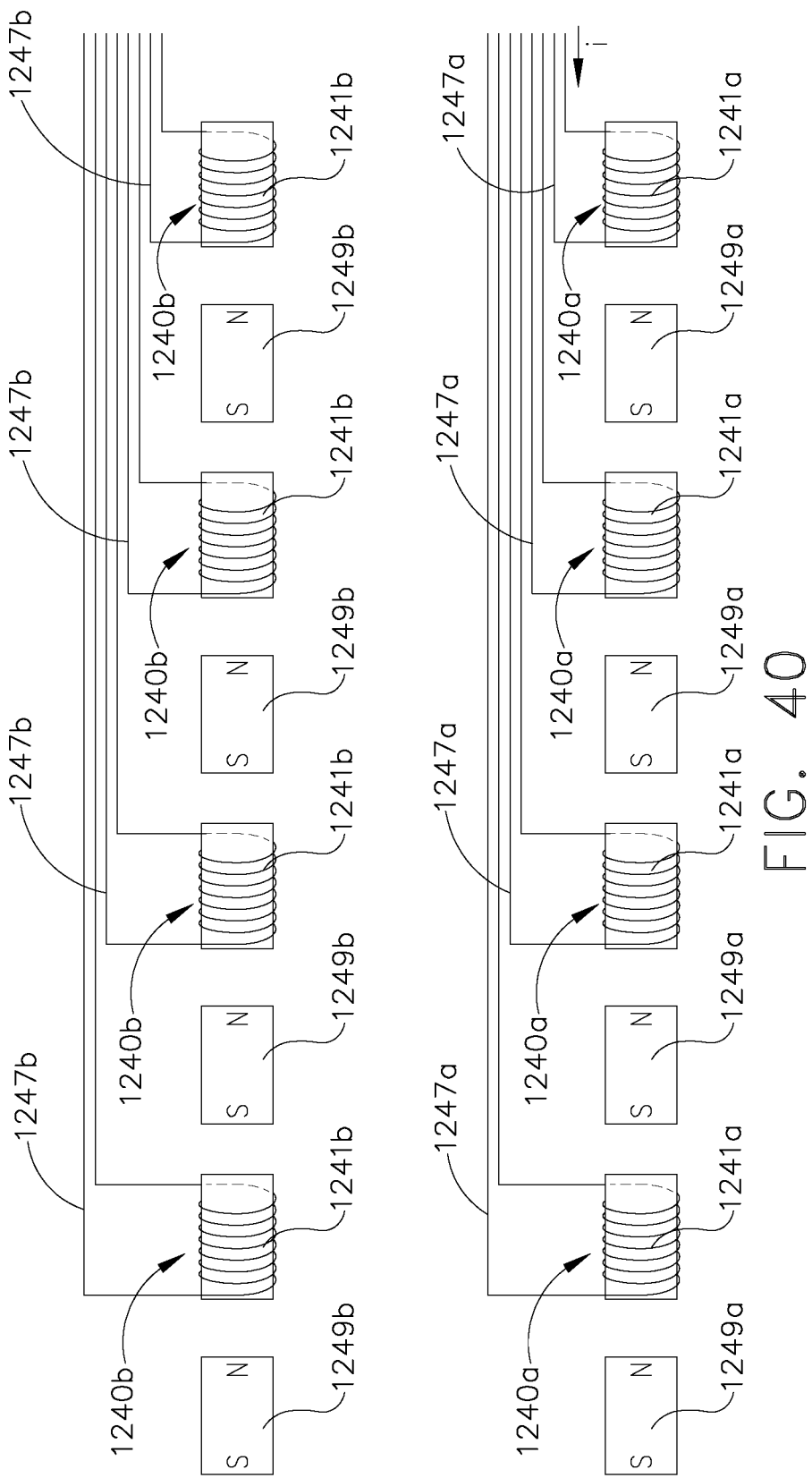
FIG. 40 is an electrical schematic of the permanent magnets and electromagnets of the articulation joint of FIG. 34.

In various embodiments, further to the above, an articulation joint can comprise first and second portions which can be configured to articulate relative to one another. In various other embodiments, an articulation joint can comprise more than two portions which can articulate relative to one another. In at least one such embodiment, referring to FIGS. 33-40, a surgical instrument, such as surgical instrument 1200, for example, can comprise a handle assembly 1202, an elongate shaft 1204, and an end effector 1206, wherein articulation joint 1220 can be configured to permit end effector 1206 to rotate relative to elongate shaft 1204, and wherein articulation joint 1220 can comprise a plurality of first joint members 1222 and a plurality of second joint members 1226, for example. In certain embodiments, referring primarily to FIGS. 34 and 35, first joint members 1222 and second joint members 1226 can be arranged in an alternating arrangement wherein, in at least one embodiment, first joint members 1222 can each include one or more permanent magnets mounted thereto and second joint members 1226 can each include one or more electromagnets mounted thereto. Referring now to FIGS. 38 and 40, each first joint member 1222 can include a first permanent magnet 1249a positioned within an aperture therein, such as an aperture 1248, for example, and, in addition, a second permanent magnet 1249b positioned within another aperture 1248 on the opposite, or at least substantially opposite, side of the first joint member 1222. Similarly, referring to FIGS. 36-40, each second joint member 1226 can include a first electromagnet 1240a positioned within an aperture therein, such as an aperture 1251, for example, and, in addition, a second electromagnet 1240b positioned within another aperture 1251 on the opposite, or at least substantially opposite, side of second joint member 1226. In various embodiments, referring again to FIGS. 34 and 35, joint members 1222 and 1226 can be arranged such that permanent magnets 1249a are aligned, or at least substantially aligned, with electromagnets 1240a and, in addition, permanent magnets 1249b are aligned, or at least substantially aligned, with electromagnets 1240b.

Figure 33:
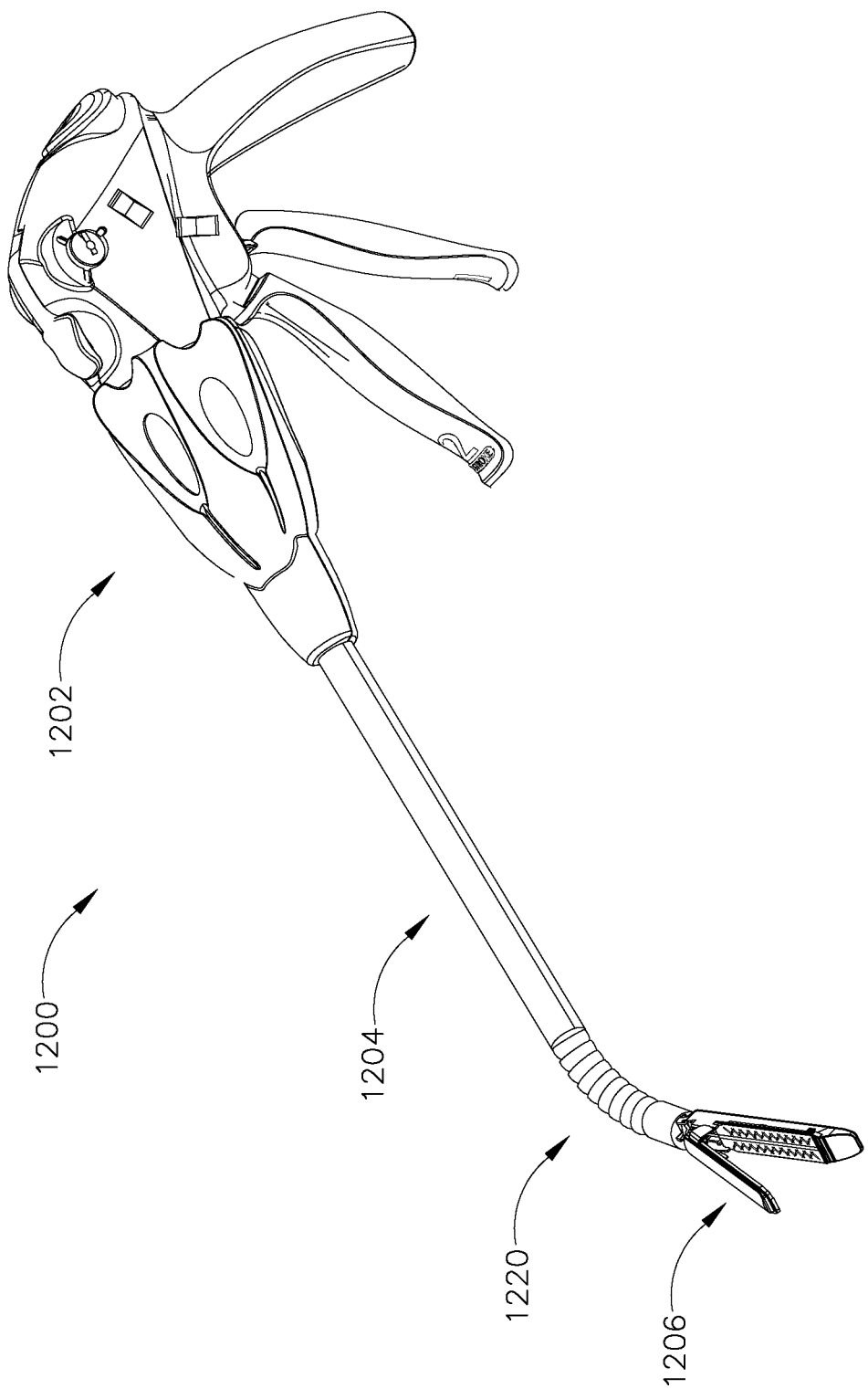
FIG. 33 is a perspective view of a surgical instrument comprising a handle assembly, an elongate shaft, and an end effector articulatable relative to the elongate shaft in accordance with at least one embodiment of the present invention.
Figure 34:
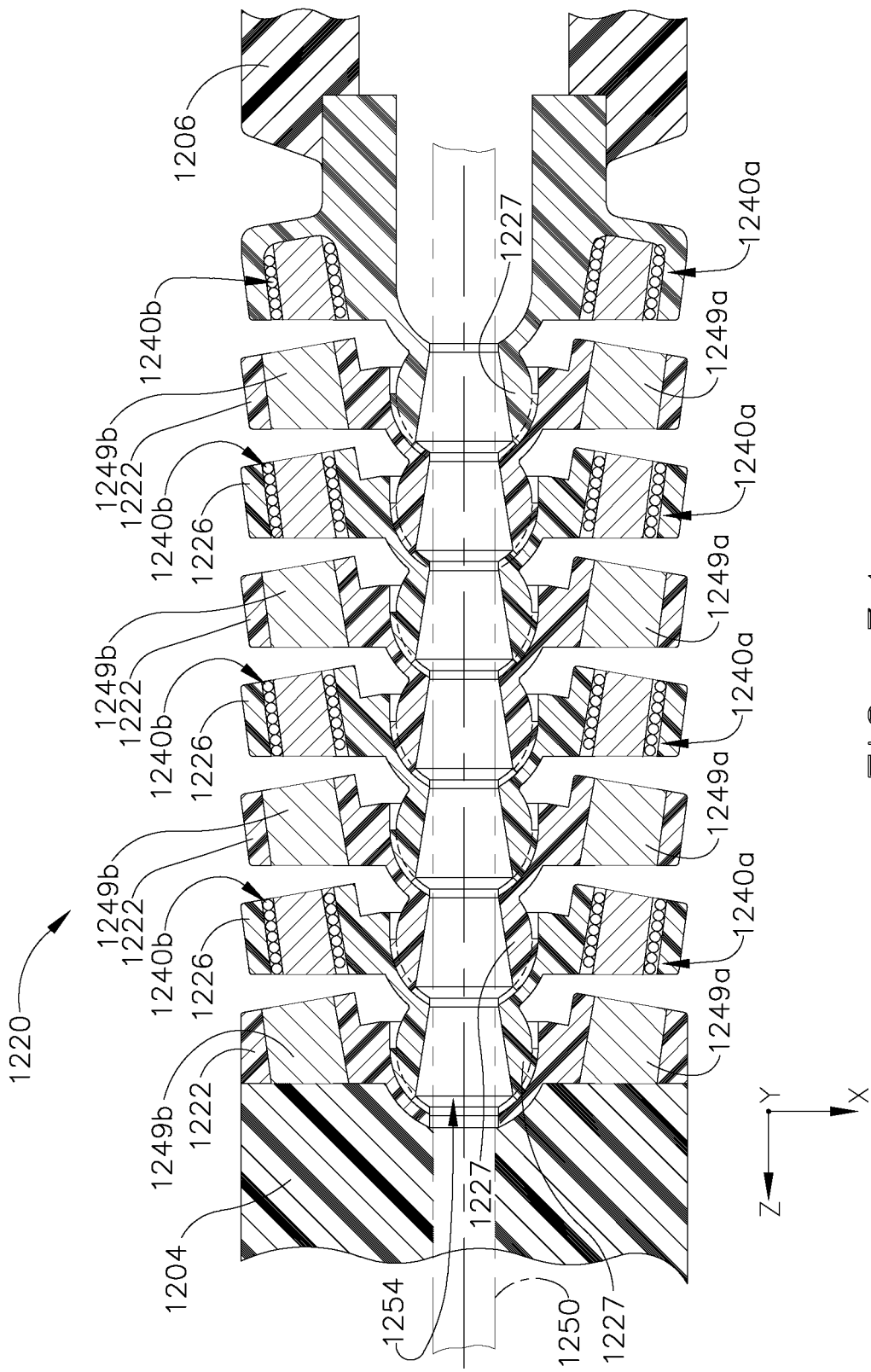
FIG. 34 is a cross-sectional view of an articulation joint connecting the elongate shaft and the end effector of FIG. 33, wherein the articulation joint comprises a plurality of discs.
Figure 35:
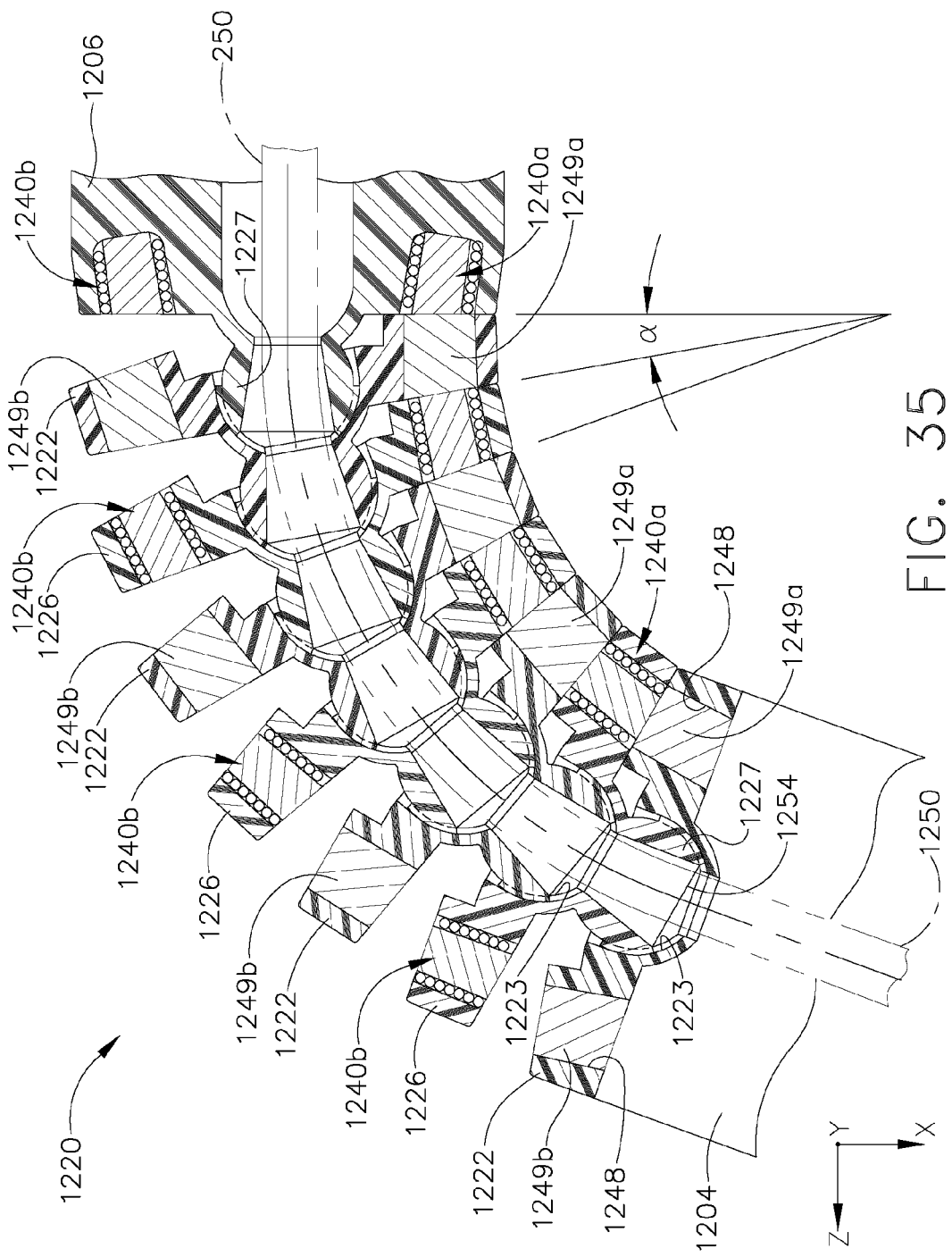
FIG. 35 is a cross-sectional view of the articulation joint of FIG. 34 illustrating the articulation joint in an articulated configuration.
Figure 36:
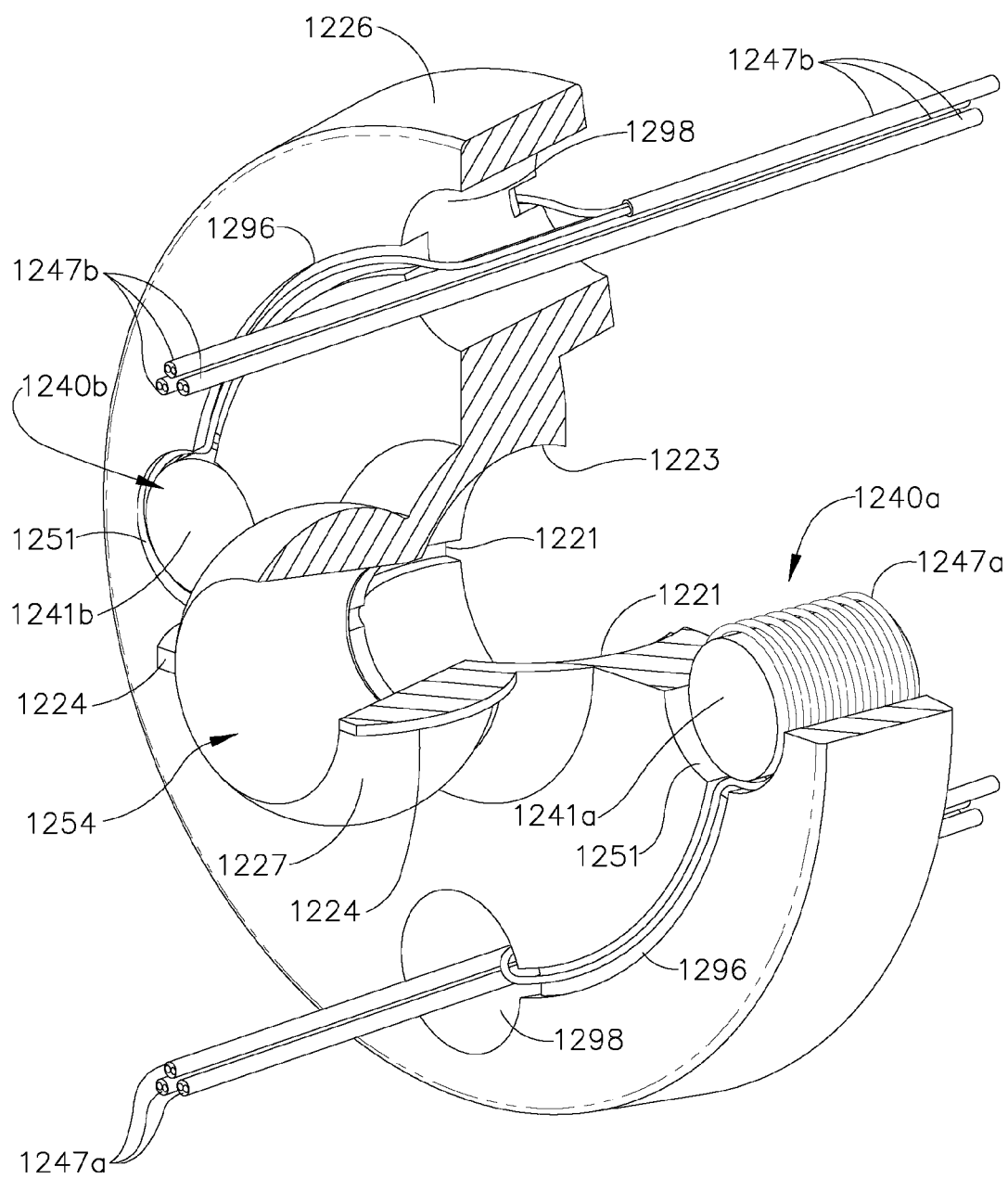
FIG. 36 is a cross-sectional perspective view of a disc of the articulation joint of FIG. 34 illustrating electromagnets positioned within a first set of apertures and wires extending through another set of apertures, the wires electrically coupling the electromagnets with a power source.
Figure 37:
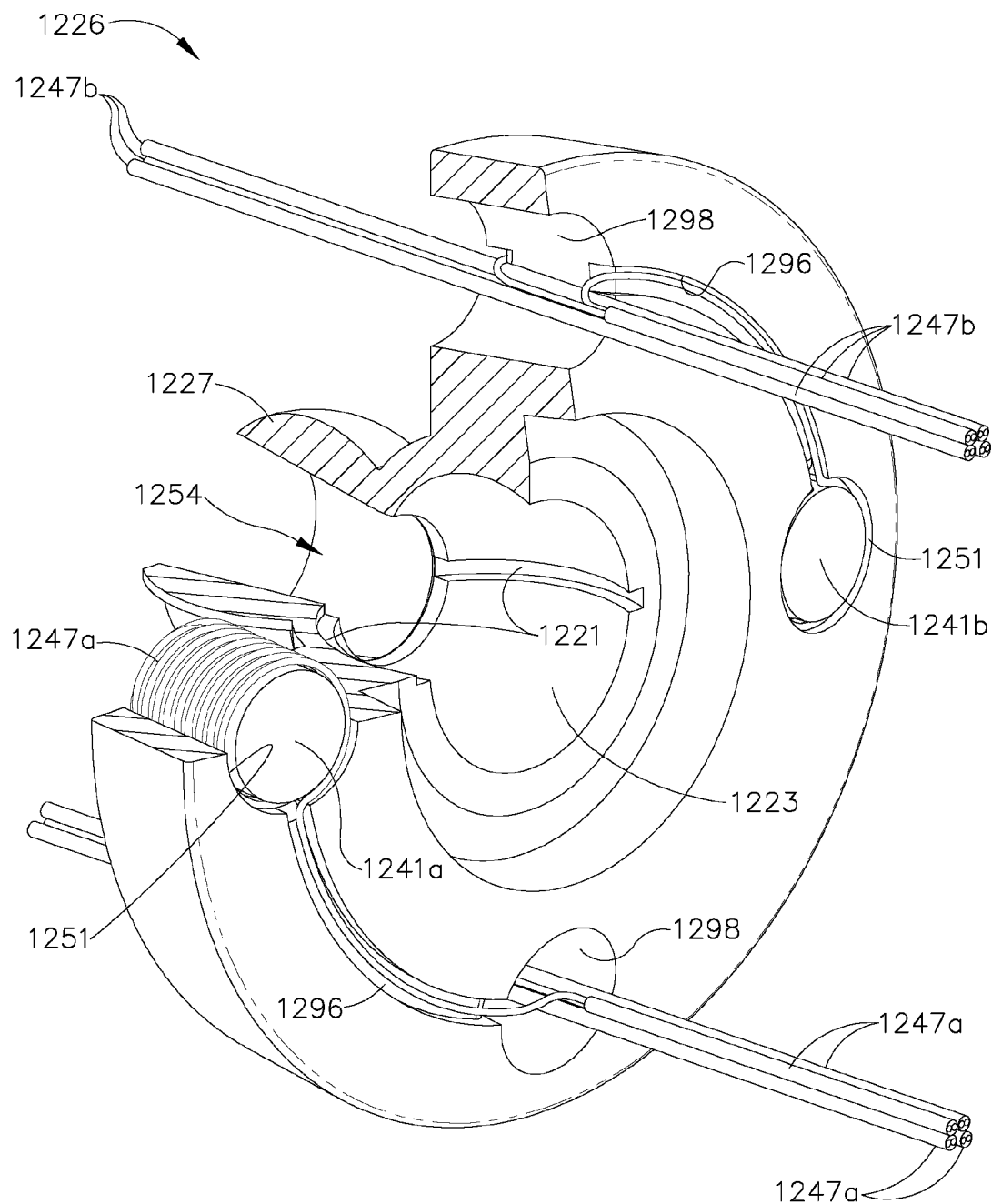
FIG. 37 is another cross-sectional perspective view of the disc of FIG. 36.

In various embodiments, further to the above, each electromagnet 1240a can comprise a core, such as core 1241a, for example, and a conductor, such as conductor 1247a, for example, wherein conductors 1247a can be configured to conduct current when a current source and/or voltage source is supplied to conductors 1247a, and wherein at least a portion of conductors 1247a can be wrapped around cores 1241a in order to generate a magnetic field having a polarity. As outlined above, the polarity of such magnetic fields may depend on the direction in which current is flowing through conductors 1247a. Similar to the above, each permanent magnet 1240b can comprise a core, such as core 1241b, for example, and a conductor, such as conductor 1247b, for example, wherein conductors 1247b can be configured to conduct current when a current source and/or voltage source is supplied to conductors 1247b. In use, in at least one embodiment, end effector 1206 can be articulated to the right, or in a clockwise direction, for example, as illustrated in FIG. 35, when current is supplied to, and/or voltage is applied to, conductors 1247a such that current flows through conductors 1247a in a first direction. More particularly, referring again to FIG. 40, electromagnets 1240a can be energized, or polarized, such that the negative, or south, poles of permanent magnets 1249a, marked with an "S", are attracted to positive, or north, poles generated by electromagnets 1240a and, in addition, the positive poles of permanent magnets 1249a, marked with an "N", are attracted to negative poles generated by electromagnets 1240a. In such circumstances, referring again to FIG. 35, the magnetomotive forces (mmf) between electromagnets 1240a and permanent magnets 1249a can be sufficient to cause first joint members 1222 and second joint members 1226 to articulate relative to each other. In certain embodiments, the joint members 1222 and 1226 can articulate relative to each other until they abut one another. In certain embodiments, end effector 1206 can be articulated to the left, or in a counter-clockwise direction, as illustrated in FIG. 33, when current is supplied to, and/or voltage is applied to, conductors 1247a such that current flows through conductors 1247a in a second, or opposite, direction. In such embodiments, referring again to FIG. 40, electromagnets 1240a can be energized, or polarized, such that the negative poles of permanent magnets 1249 are repelled by negative poles generated by electromagnets 1240a and, in addition, the positive poles of permanent magnets 1249*a* are repelled by poles generated by electromagnets 1240*a*.

In various embodiments, similar to the above, end effector 1206 can be articulated to the left, or in a counter-clockwise direction, for example, when current is supplied to, and/or voltage is applied to, conductors 1247*b* such that current flows through conductors 1247*b* in a first direction. More particularly, referring again to FIG. 40, electromagnets 1240*b* can be energized, or polarized, such that the negative, or south, poles of permanent magnets 1249*b*, marked with an "S", are attracted to positive, or north, poles generated by electromagnets 1240*b* and, in addition, the positive poles of permanent magnets 1249*b*, marked with an "N", are attracted to negative poles generated by electromagnets 1240*b*. In such circumstances, referring again to FIG. 33, the magnetomotive forces (mmf) between electromagnets 1240*b* and permanent magnets 1249*b* can be sufficient to cause first joint members 1222 and second joint members 1226 to articulate relative to each other. In certain embodiments, the joint members 1222 and 1226 can articulate relative to each other until they abut one another. Also similar to the above, end effector 1206 can be articulated to the right, or in a clockwise direction, as illustrated in FIG. 35, when current is supplied to, and/or voltage is applied to, conductors 1247*b* such that current flows through conductors 1247*b* in a second, or opposite, direction. In such embodiments, referring again to FIG. 40, electromagnets 1240*b* can be energized, or polarized, such that the negative poles of permanent magnets 1249*b* are repelled by negative poles generated by electromagnets 1240*b* and, in addition, the positive poles of permanent magnets 1249*b* are repelled by positive poles generated by electromagnets 1240*b*. In various embodiments, further to the above, end effector 1206 and/or elongate shaft 1204 can include one or more permanent magnets and/or electromagnets which can be configured to articulate one or more of joint members 1222 and/or 1226.

In various embodiments, also further to the above, every electromagnet 1240*a*, for example, in articulation joint 1220 can be energized simultaneously in order to achieve a maximum rightward articulation of end effector 1206. Similarly, every electromagnet 1240*b*, for example, can be energized simultaneously in order to achieve a maximum leftward articulation of end effector 1206. In at least one embodiment, referring to FIG. 35, articulation joint 1220 can comprise three movable first joint members 1222 and three movable second joint members 1226, for example. In at least one such embodiment, each of the six joint members can be configured to articulate approximately 10 degrees relative to an adjacent joint member, for example, resulting in approximately 70 degrees of total articulation, for example. In certain embodiments, although not illustrated, a single conductor can be utilized to energize, or polarize, each of the electromagnets 1240*a* and, in addition, a single conductor can be utilized to energize, or polarize, each of the electromagnets 1240*b*. In effect, electromagnets 1240*a* can be placed in series with one another and, similarly, electromagnets 1240*b* can be placed in series with one another. In certain other embodiments, as illustrated in FIG. 40, for example, each electromagnet 1240*a* can be activated independently of the other electromagnets 1240*a* and, similarly, each electromagnet 1240*b* can be activated independently of the other electromagnets 1240*b*. In at least one such embodiment, the electromagnets 1240*a*, 1240*b* can be selectively actuated such that end effector 1206 can be articulated less than its maximum articulation. For example, only one electromagnet 1240*a* may be energized, or polarized, in order to articulate end effector 1206 approximately 20 degrees; two electromagnets 1240*a* may be energized, or polarized, to articulate end effector 1206 approximately 40 degrees; and three electromagnets 1240*a* may be energized, or polarized, to articulate end effector 1206 approximately 70 degrees. In certain embodiments, end effector 1206 and/or elongate shaft 1204 can include one or more electromagnets which can be actuated to articulate end effector 1206 more than 70 degrees, such as approximately 80 degrees, for example, or less than 20 degrees.

As described above, each electromagnet 1240*a*, 1240*b* can include a conductor 1247*a*, 1247*b*, respectively, which can be configured to conduct current. In various embodiments, conductors 1247*a* and 1247*b* can comprise wires, for example, which can be sufficiently flexible to accommodate relative movement between first joint members 1222 and second joint members 1226. In at least one embodiment, conductors 1247*a* and 1247*b* can extend through one or more throughholes 1298 in joint members 1222 and 1226, wherein conductors 1247*a* and 1247*b* can have sufficient slack such that they are not damaged when end effector 1206 is articulated. In at least some embodiments, referring again to FIG. 36, first joint members 1222 and/or second joint members 1226 can further comprise one or more channels 1296, for example, which can be configured to receive one or more conductors 1247*a* and/or 1247*b* such that the conductors can be seated flush with and/or below the faces of joint members 1222 and 1226. In various embodiments, one or more conductors, such as conductors 1247*a* and 1247*b*, for example, can extend through passages 1250 of joint members 1222 and 1226. In at least one such embodiment, passages 1250 can lie along a neutral axis of the articulation joint such that the stress and strain applied to conductors 1247*a* and 1247*b* can be minimized. Stated another way, in at least one embodiment, a path extending through passages 1250 may define a length through the articulation joint wherein the length does not change, or at least substantially change, when the end effector is articulated such that the conductors are not subjected to large deformations.

In various embodiments, as described above, first joint members 1222 can be configured to articulate relative to second joint members 1226 and, correspondingly, second joint members 1226 can be configured to articulate relative to first joint members 1222. In at least one embodiment, referring again to FIGS. 36-39, joint members 1222 and 1226 can be coupled together by one or more ball and socket arrangements, or joints. More particularly, each first joint member 1222 can include a ball member 1227 which can be configured to be received within a socket 1223 of an adjacent second joint member 1226. Similarly, each second joint member 1226 can also include a ball member 1227 which can be configured to be received within a socket 1223 of an adjacent first joint member 1222. In at least one such embodiment, ball members 1227 can be spherical, or at least substantially spherical, and sockets 1223 can comprise a semispherical, or an at least partially spherical, pocket. In various embodiments, the ball and socket joints can be configured to permit the first and second joint members 1222 and 1226 to move in a side-to-side direction, an up-and-down direction, and/or any other suitable direction. In various embodiments, ball members 1227 and sockets 1223 can define a passage 1254 which can be configured to slidably receive firing member 1250 (FIG. 35) and define a path for firing member 1250, especially when end effector 1206 is in an articulated position. In certain embodiments, one or more of the ball and socket joints can be configured to limit the relative movement between joint members 1222 and 1226. In at least one such embodiment, one or more of the ball and socket joints can be configured to limit the relative movement between the first and second joint members such that the joint members can only move relative to each other along a plane, for example. Referring once again to FIG. 36, ball members 1227 can include one or more alignment flanges 1224, for example, extending therefrom which, referring now to FIGS. 37 and 38, can be configured to be received within alignment grooves 1221, for example, defined within sockets 1223. In at least one such embodiment, alignment ridges 1224 and alignment grooves 1221 can be sized and configured to limit the relative movement between first joint members 1222 and second joint members 1226 along a plane defined by alignment flanges 1224, for example.

In any event, further to the above, one or more first joint members 1222 and one or more second joint members 1226 can be realigned along an axis after they have been moved or articulated relative to one other. In at least one embodiment, electromagnets 1240a and 1240b, for example, can be energized in order to straighten out articulation joint 1220 and, in addition, realign end effector 1206 with shaft 1204. More particularly, in at least one embodiment, electromagnets 1240a and electromagnets 1240b can be energized simultaneously such that first joint members 1222 and second joint members 1226 are positioned along a central axis defined by shaft 1204. In certain embodiments, the magnitude of current, and/or power, supplied to electromagnets 1240a and 1240b can be different, at least initially, in order to move joint members 1222 and 1226 into substantial alignment with one another wherein, thereafter, the magnitude of the current and/or power supplied to electromagnets 1240a and 1240b can be equalized, or at least substantially equalized, such that joint members 1222 and 1226 can be more precisely aligned. In certain embodiments, the magnitude of the current and/or power supplied to electromagnets 1240a and 1240b can be the same, or at least substantially the same, initially, especially when end effector 1206 has not been significantly articulated.

Figure 41:
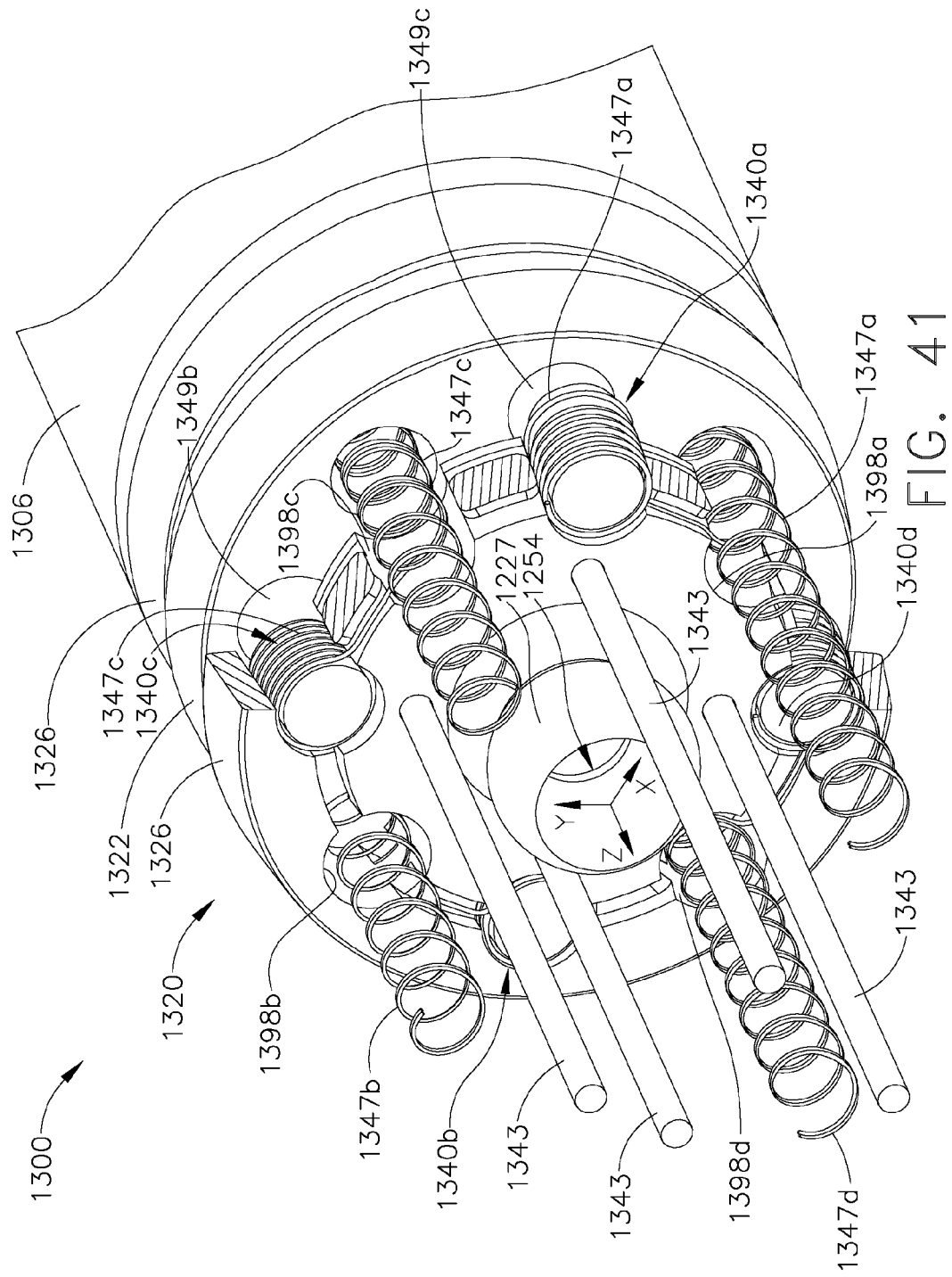
FIG. 41 is a partial perspective view of an articulation joint of a surgical instrument in accordance with at least one alternative embodiment of the present invention illustrated with some components removed and others shown in cross-section.
Figure 42:
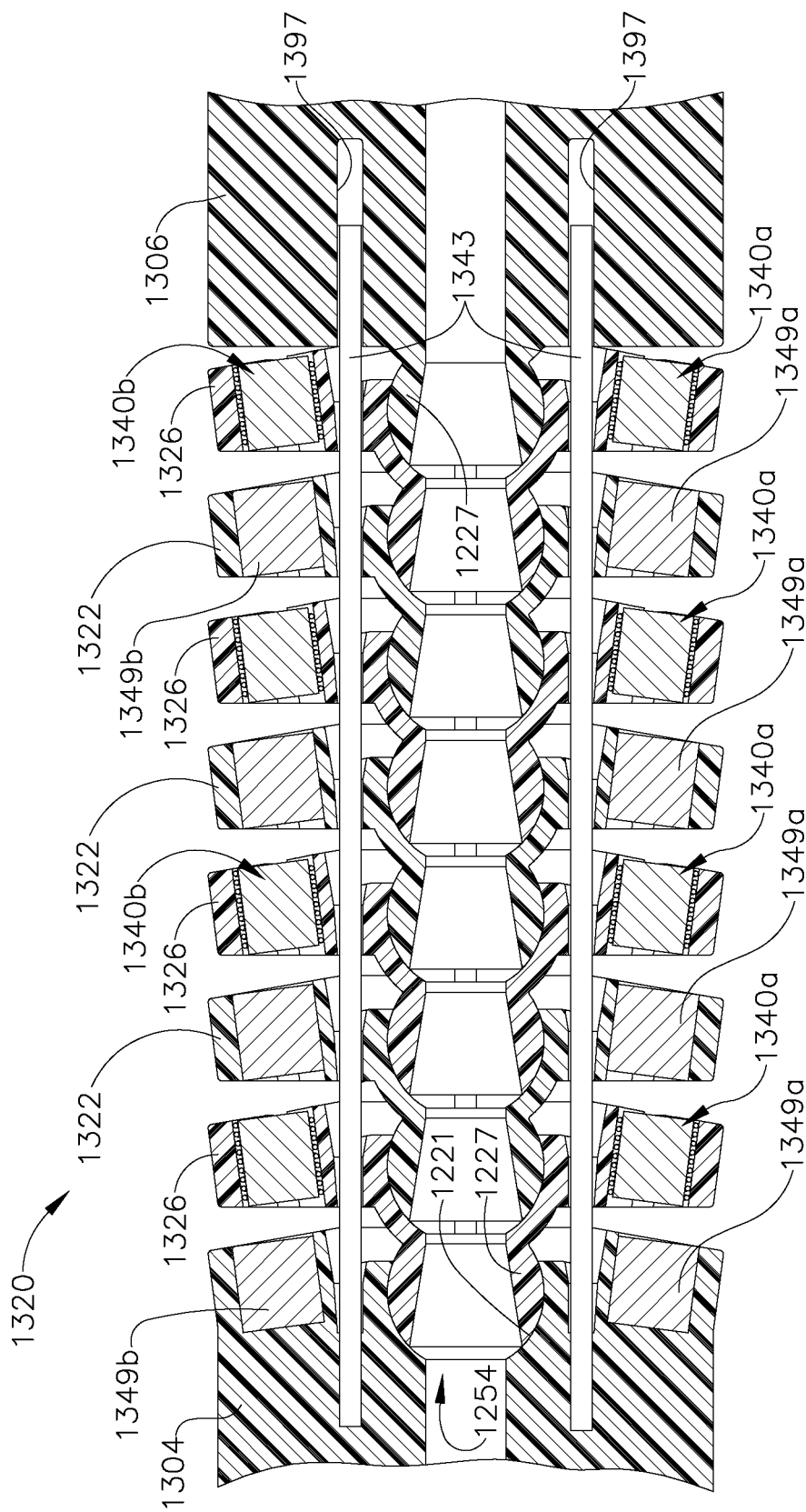
FIG. 42 is a cross-sectional view of the articulation joint of FIG. 41 illustrating alternating first and second discs of the articulation joint.

In various embodiments, further to the above, an end effector of a surgical instrument can be articulated in more than one plane. In at least one embodiment, referring now to FIGS. 41-45, a surgical instrument 1300 can comprise an elongate shaft 1304, an end effector 1306, and an articulation joint 1320 which can be configured to permit end effector 1306 to articulate relative to shaft 1304. Similar to articulation joint 1220, articulation joint 1320 can comprise a plurality of first joint members 1322 and a plurality of second joint members 1326 which can be configured to articulate relative to one another. Unlike joint members 1222 and 1226, though, joint members 1322 and 1326 do not include alignment features 1221 and 1224 which limit relative movement therebetween. In at least one embodiment, as a result, end effector 1306 can be articulated in a plurality of directions and/or planes. In certain embodiments, referring primarily to FIG. 41, each second joint member 1326 can include four electromagnets, such as electromagnets 1340a, 1340b, 1340c, and 1340d, for example, which can be mounted to second joint member 1326 within apertures in joint member 1326. In at least one such embodiment, electromagnets 1340a-1340d can be positioned equidistantly with respect to each other and with respect to the center of joint member 1326. Correspondingly, each first joint member 1322 can include four permanent magnets comprising, referring to FIG. 42, permanent magnets 1349a, 1349b, 1349c (FIG. 41), and a fourth permanent magnet not illustrated, wherein each permanent magnet 1349a can be aligned with one or more electromagnets 1340a, wherein each permanent magnet 1349b can be aligned with one or more electromagnets 1340b, wherein each permanent magnet 1349c can be aligned with one or more electromagnets 1340c, and wherein each fourth permanent magnet can be aligned with one or more electromagnets 1340d.

Figure 43:
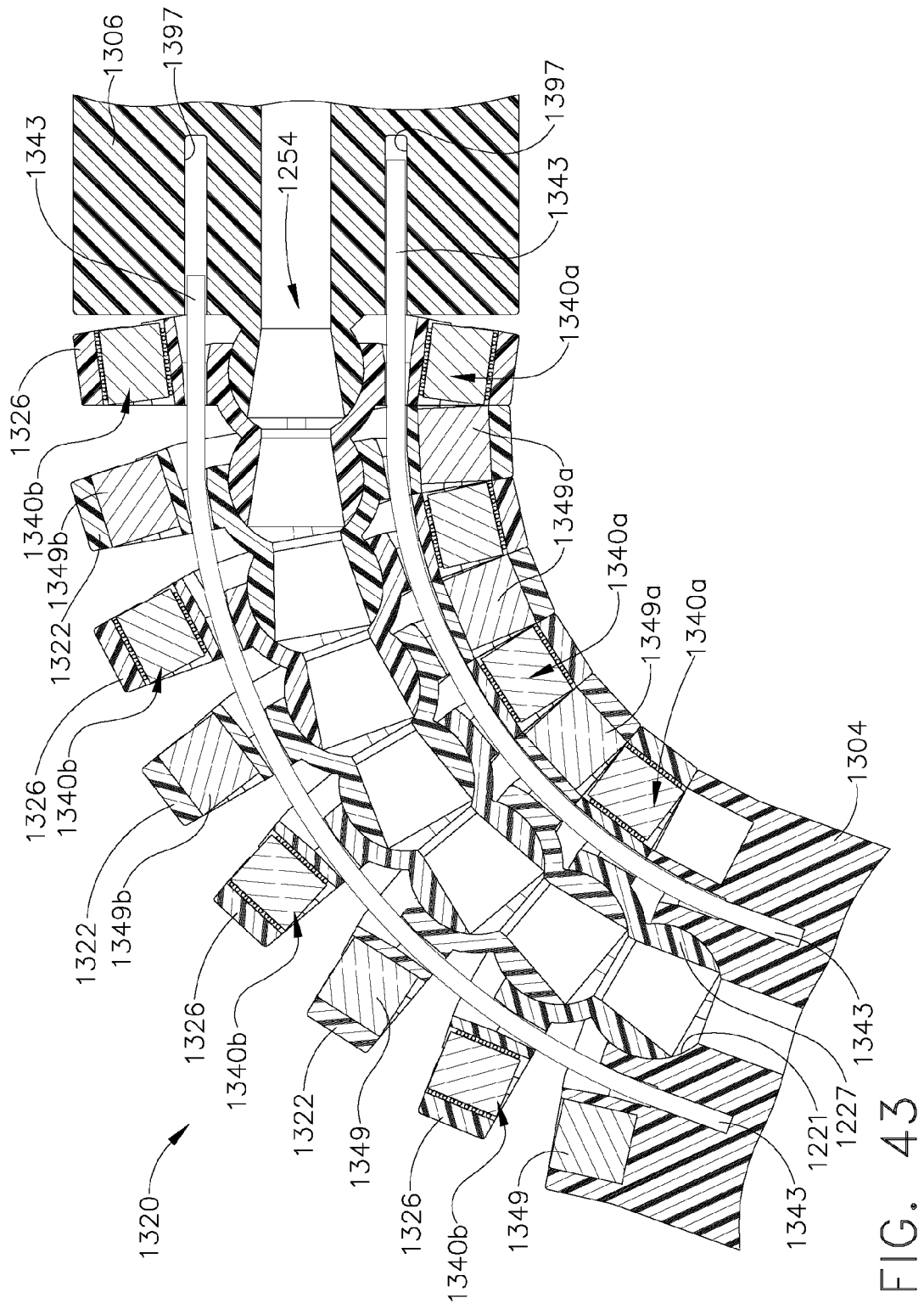
FIG. 43 is a cross-sectional view of the articulation joint of FIG. 41 illustrated in an articulated configuration.
Figure 44:
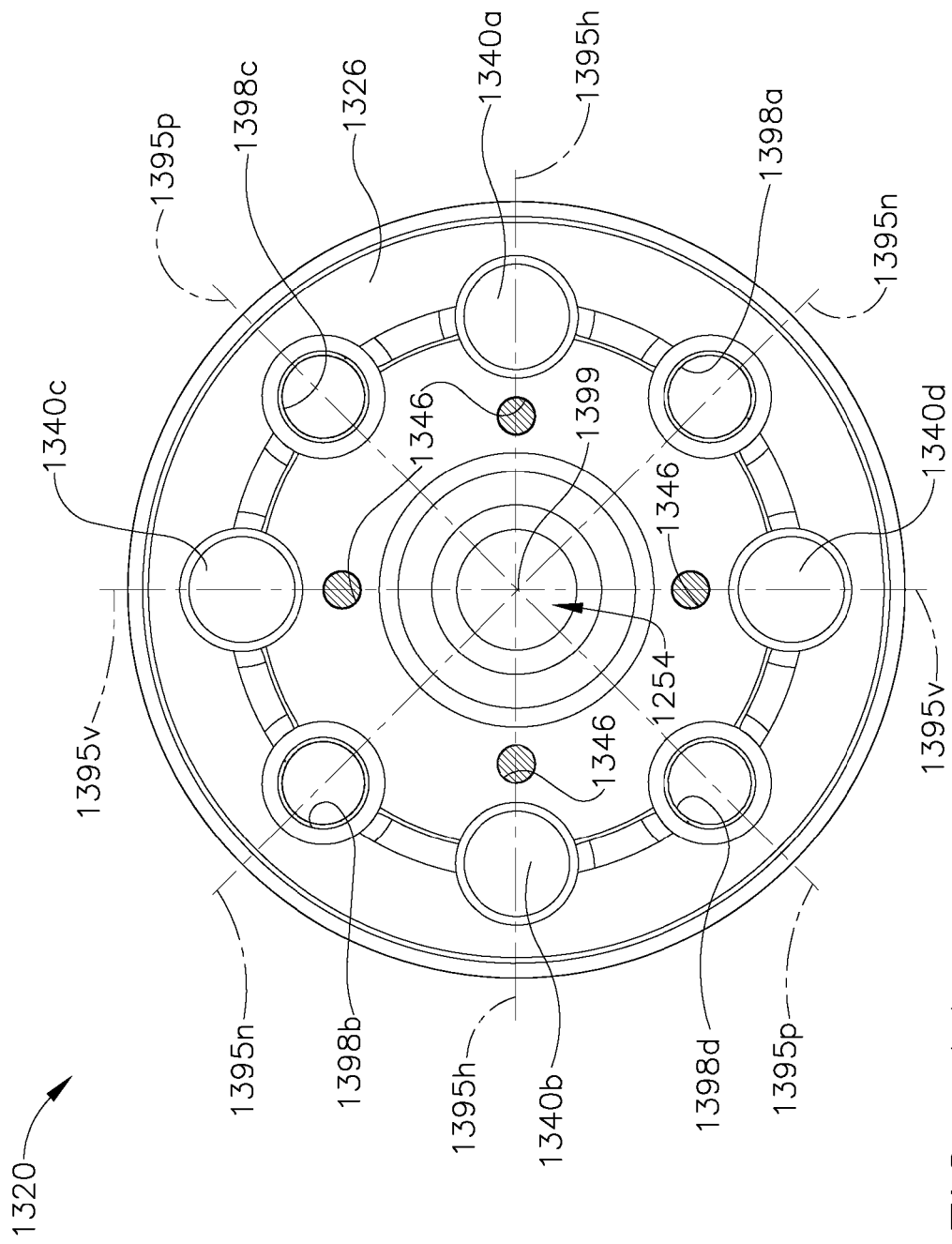
FIG. 44 is an end view of the articulation joint of FIG. 41.
Figure 45:
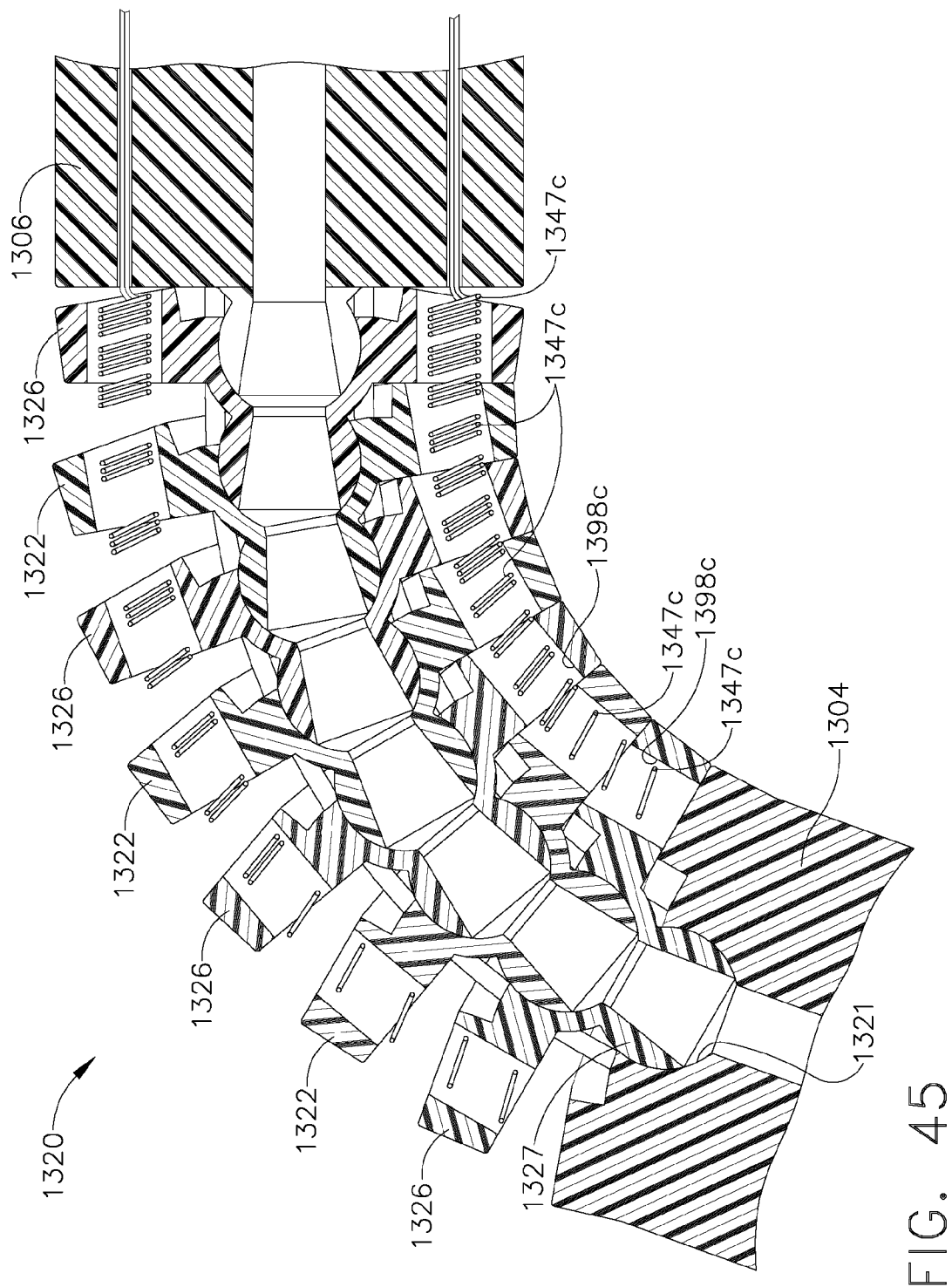
FIG. 45 is another cross-sectional view of the articulation joint of FIG. 41 illustrating the expanded and contracted configurations of electromagnet wires positioned within the discs of the articulation joint.

In use, similar to the above and referring to FIG. 43, electromagnets 1340a and/or electromagnets 1340b can be selectively actuated in order to articulate end effector 1306 relative to elongate shaft 1304 in left and right directions. Stated another way, referring to FIG. 44, end effector 1306 can be articulated in left and right directions with respect to axis 1395v, wherein, in some embodiments, axis 1395v can extend through electromagnets 1340c and 1340d and can intersect, and extend transversely to, longitudinal axis 1399. In addition to the above, electromagnets 1340c and/or electromagnets 1340d can be selectively actuated in order to articulate end effector 1306 relative to elongate shaft 1304 in up and down directions. Stated another way, end effector 1306 can be articulated in up and down directions with respect to axis 1395h, wherein, in some embodiments, axis 1395h can extend through electromagnets 1340a and 1340b and can intersect, and extend transversely to, longitudinal axis 1399. In various embodiments, any suitable combination of electromagnets 1390a, 1390b, 1390c, and 1390d can be actuated in order to articulate end effector 1306 relative to elongate shaft 1304 in any suitable direction. For example, referring again to FIG. 44, electromagnets 1340b and 1340c can be actuated in order to articulate end effector 1306 in a direction along axis 1395n. In such an embodiment, the magnitude of the current flowing through conductors 1347b can be the same, or at least substantially the same, as the magnitude of the current flowing through conductors 1347c such that the intensities of the magnetic fields generated by electromagnets 1340b and 1340c can be the same, or at least substantially the same, such that they apply equal, or at least substantially equal, magnetomotive forces to their respectfully-aligned permanent magnets. Electromagnets 1340a and 1340d can be actuated in order to articulate end effector 1306 in an opposite direction along 1395n. Similarly, electromagnets 1340a and 1340c can be actuated in order to articulate end effector 1306 in a direction along axis 1395p and, in addition, electromagnets 1340b and 1340d can be actuated in order to articulate end effector 1306 in an opposite direction along axis 1395p.

In various embodiments, as outlined above, electromagnets 1340b and 1340c can be actuated in order to articulate end effector 1306 in a direction along axis 1395n, for example. In at least one such embodiment, electromagnets 1340b and 1340c can be actuated in order to attract permanent magnets 1349b and 1349c, respectively, thereto. Contemporaneously, in certain embodiments, electromagnets 1340a and 1340d can be actuated in order to repel permanent magnets 1349a and 1349d, respectively, in order to assist in the articulation of end effector 1306. In various embodiments, in view of the above, any suitable combination of electromagnets can be actuated such that they can attract and/or repel the various permanent magnets associated therewith, for example, at the same time and/or in any suitable order.

As outlined above, various combinations of electromagnets 1340a, 1340b, 1340c, and 1340d can be actuated in order to articulate end effector 1306 wherein, in some embodiments, the same magnitude of current can be supplied to the actuated electromagnets in order to articulate end effector 1306 along axes 1395n and 1395p, i.e., along approximately 45 degree angles with respect to axes 1395v and 1395h, for example. In other embodiments, different magnitudes of current can be supplied to various electromagnets such that end effector 1306 is articulated in other directions. For example, conductors 1347c of electromagnets 1340c can be supplied with a current which has approximately twice the magnitude of the current supplied to conductors 1347b of electromagnets 1340*b* so as to articulate end effector 1306 in a direction which is intermediate axes 1395*n* and 1395*v*. In any event, electromagnets 1340*a*, 1340*b*, 1340*c*, and 1340*d* can all be actuated simultaneously in order to re-straighten articulation joint 1320 along longitudinal axis 1399, for example. In certain embodiments, referring once again to FIGS. 41 and 43, articulation joint 1320 can further comprise one or more flexible straightening and alignment rods, such as rods 1343, for example, which can be configured to straighten articulation joint 1320. In at least one such embodiment, the proximal ends of rods 1343 can be mounted to elongate shaft 1304 wherein rods 1343 can extend through apertures 1346 in joint members 1322 and 1326 and extend into apertures 1397 in end effector 1306. When end effector 1306 is articulated as described above, rods 1343 can be sufficiently flexible to permit such articulation but can be sufficiently resilient to return back to their original shape once electromagnets 1340*a*, 1340*b*, 1340*c*, and 1340*d* have been sufficiently deenergized. In at least one embodiment, rods 1343 can be configured to slide within apertures 1346 and apertures 1397 in order to accommodate the various configurations of articulation joint 1320. Similar to the above, referring to FIGS. 41 and 45, joint members 1322 and 1326 can include one or more throughholes 1398*a*-1398*d* which can be configured to slidably receive conductors 1347*a*-1347*d* therein, wherein conductors 1347*a*-1347*d* can also be sufficiently flexible to accommodate the various configurations of articulation joint 1320.

Figure 46:
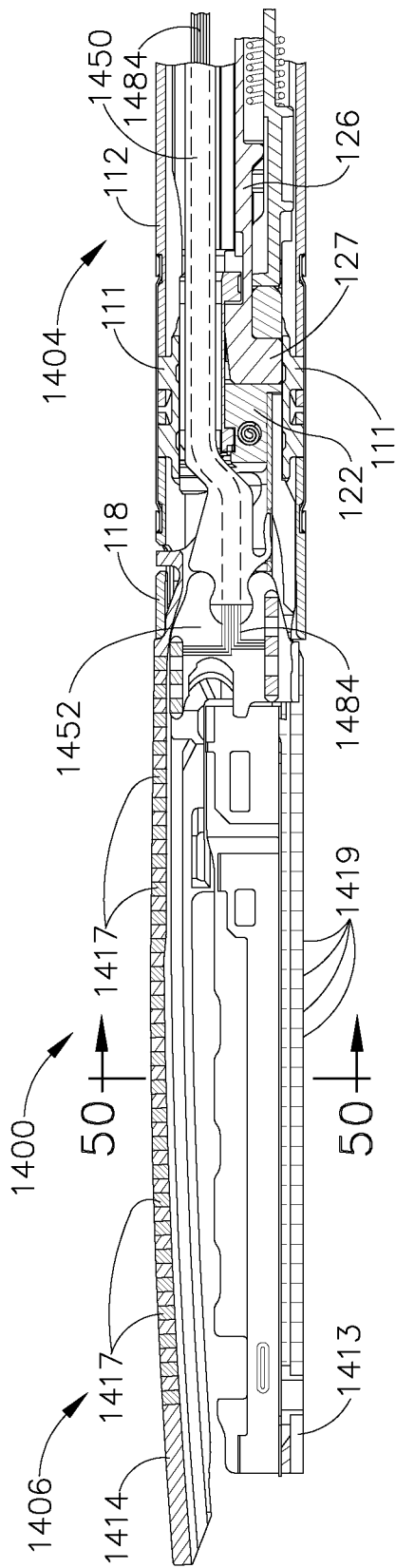
FIG. 46 is a cross-sectional view of an end effector of a surgical instrument in accordance with at least one embodiment of the present invention illustrating a plurality of permanent magnets positioned within an anvil of the end effector.
Figure 47:
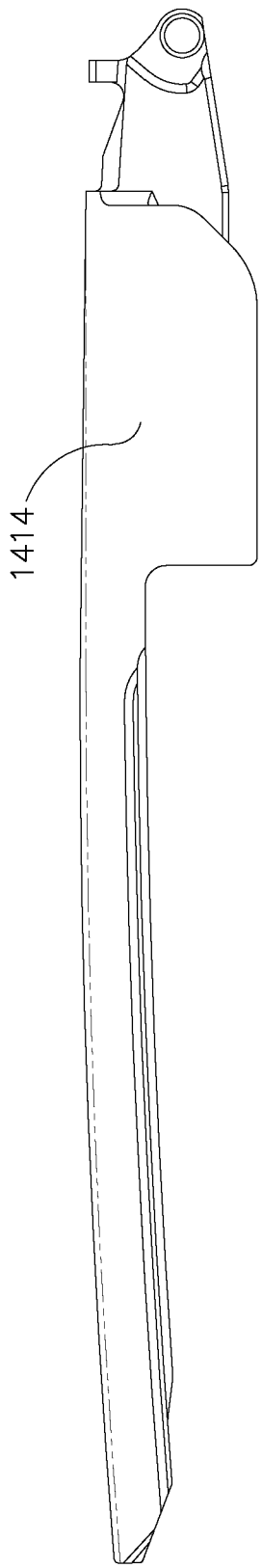
FIG. 47 is an elevational view of the anvil of FIG. 46.
Figure 48:
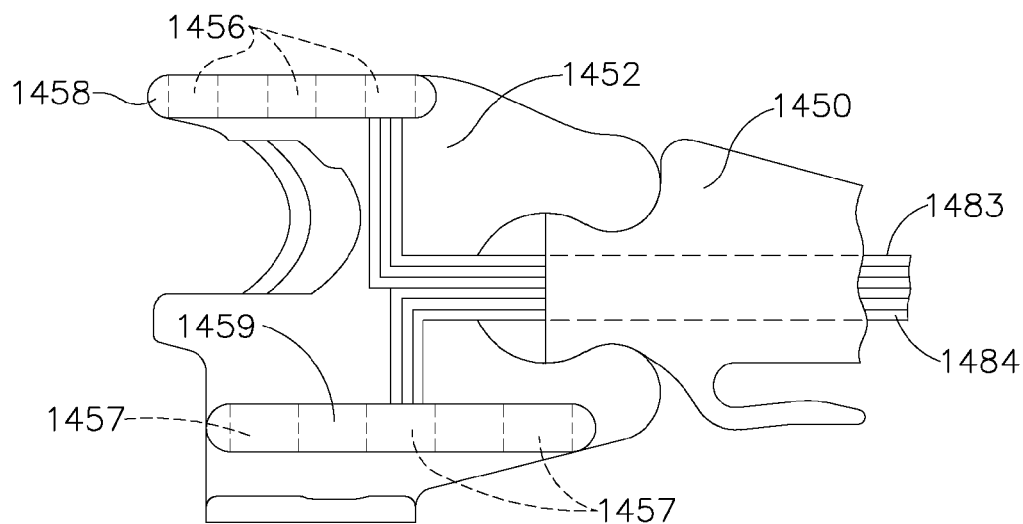
FIG. 48 is an elevational view of a cutting member of the end effector of FIG. 46 comprising a plurality of electromagnets configured to cooperate with permanent magnets positioned in the end effector of the surgical instrument and advance and/or retract the cutting member within the end effector.
Figure 49:
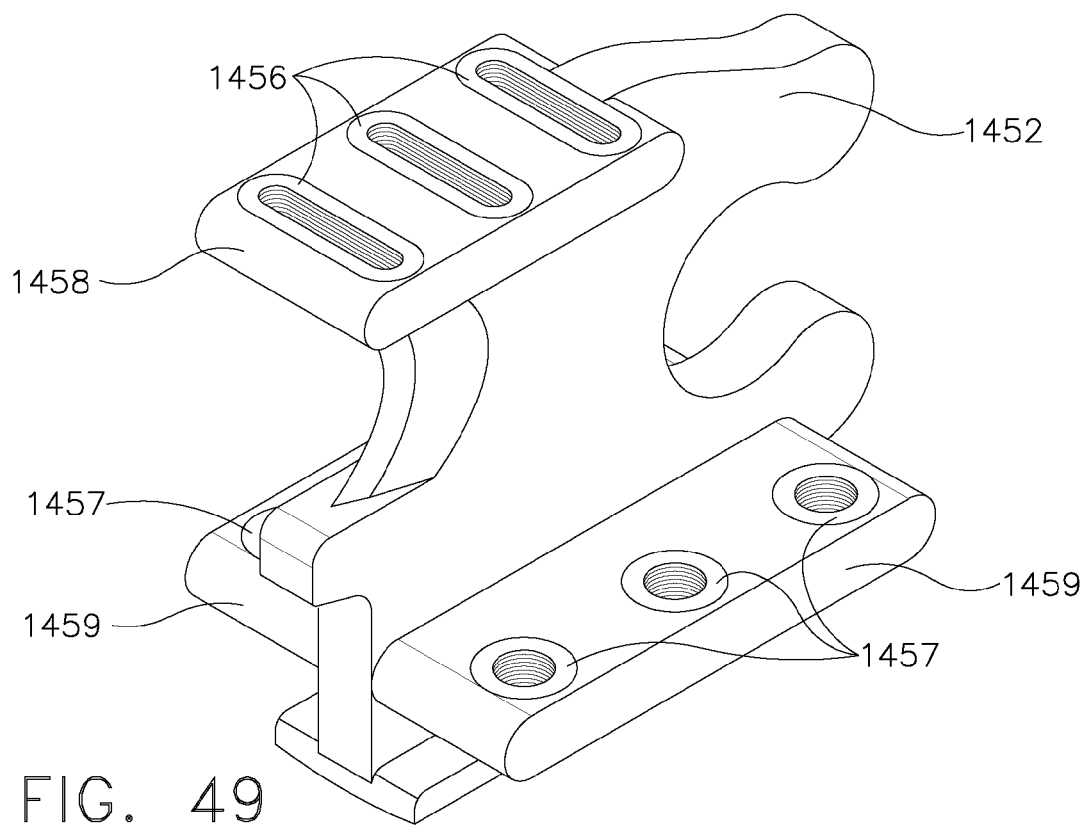
FIG. 49 is a perspective view of the cutting member of FIG. 48.
Figure 50:
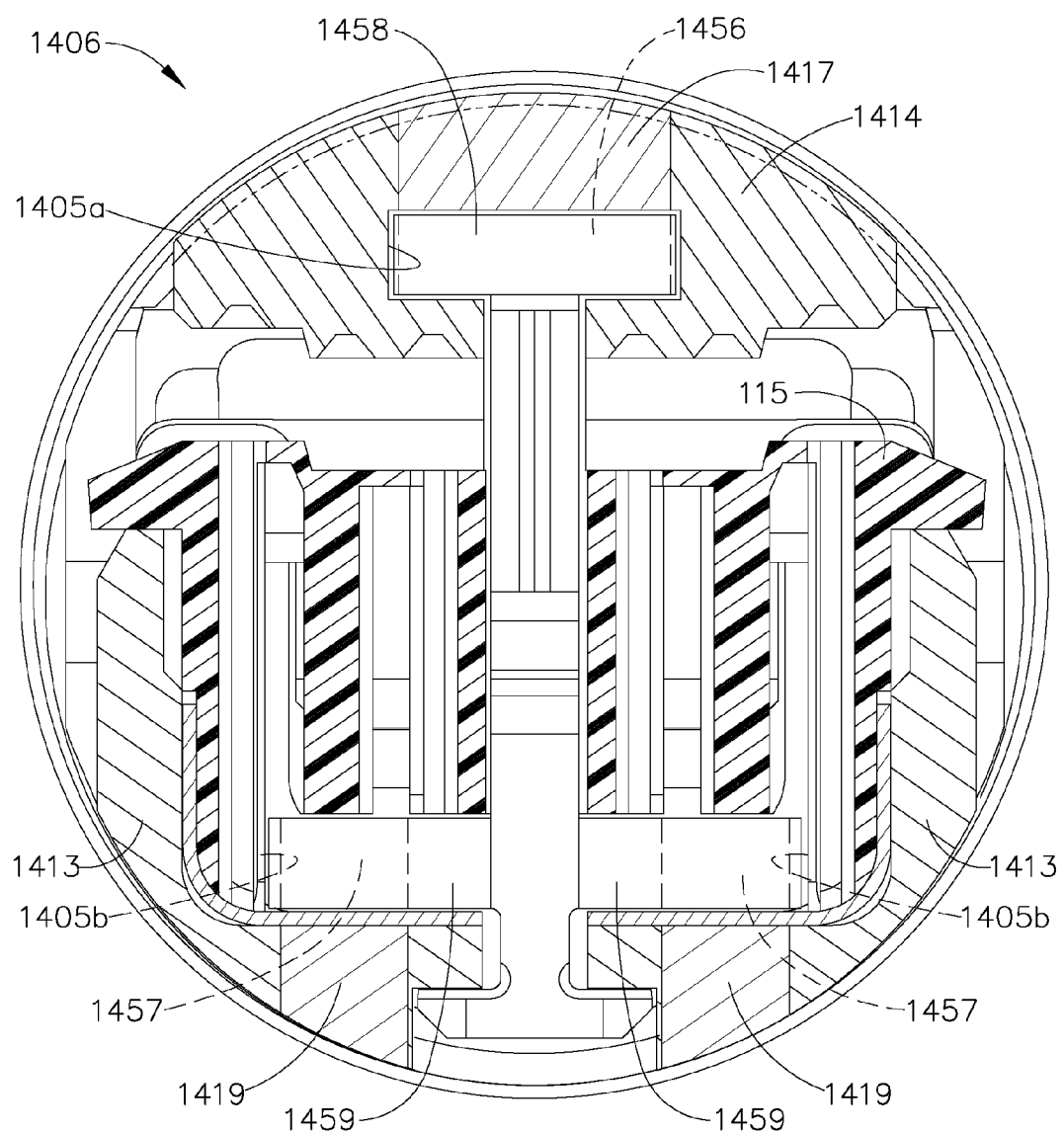
FIG. 50 is another cross-sectional view of the end effector of FIG. 46.

As described above, a system of permanent magnets and electromagnets can be utilized to articulate an end effector relative to an elongate shaft of a surgical instrument. In various embodiments, a surgical instrument can include a system of permanent magnets and electromagnets configured to drive a cutting member and/or staple driver through an end effector of the surgical instrument. In at least one embodiment, referring to FIGS. 46-50, a surgical instrument, such as surgical instrument 1400, for example, can include an end effector 1406, an elongate shaft 1404, and a cutting member 1452 configured to be advanced and/or retracted within end effector 1406. Referring primarily to FIGS. 46 and 50, end effector 1406 can comprise a staple cartridge channel 1413 configured to support and/or retain staple cartridge 115, for example, therein. End effector 1406 can further comprise an anvil 1414 which can be rotatably coupled to staple cartridge channel 1413 such that anvil 1414 can be rotated between open and closed positions. As best illustrated in FIG. 46, anvil 1414 can further include a plurality of permanent magnets 1417 mounted thereto wherein, when anvil 1414 is in its closed position, for example, permanent magnets 1417 can be configured to advance or retract cutting member 1452. More particularly, in at least one embodiment, cutting member 1452 can comprise one or more electromagnets 1456 (FIGS. 48-50) which can be energized, or polarized, in order to create a magnetic field, or fields, which can interact with permanent magnets 1417 and generate a magnetomotive force therebetween. In various embodiments, such forces can displace cutting member 1452 proximally and/or distally within end effector 1406. In at least one embodiment, permanent magnets 1417 can be secured within equidistant, or at least substantially equidistant, apertures in anvil 1414 and, in addition, electromagnets 1456 can be mounted within upper shoe 1458. In various embodiments, referring to FIG. 50, upper shoe 1458 can be configured to be received within channel 1405*a* in anvil 1414 such that, when cutting member 1452 traverses anvil 1414, upper shoe 1458 can bias anvil 1414 downwardly to compress tissue positioned intermediate anvil 1414 and staple cartridge 115, for example.

In various embodiments, similar to the above, staple cartridge channel 1413 can further include a plurality of permanent magnets 1419 mounted thereto wherein permanent magnets 1419 can be configured to advance or retract cutting member 1452. More particularly, in at least one embodiment, cutting member 1452 can comprise one or more electromagnets 1457 which can be energized, or polarized, in order to create a magnetic field, or fields, which can interact with permanent magnets 1419 and generate a magnetomotive force therebetween. In various embodiments, such forces can displace cutting member 1452 proximally and/or distally within end effector 1406. In at least one embodiment, permanent magnets 1419 can be secured within equidistant, or at least substantially equidistant, apertures in staple cartridge channel 1413 and, in addition, electromagnets 1457 can be mounted within lower shoe 1459. In various embodiments, referring to FIG. 50, lower shoe 1459 can be configured to be received within channel 1405*b* in staple cartridge 115 such that, when cutting member 1452 traverses staple cartridge 115, lower shoe 1459 can co-operate with upper shoe 1458 to compress tissue positioned intermediate anvil 1414 and staple cartridge 115, for example. In certain embodiments, various portions of staple cartridge 115, staple cartridge channel 1413, and/or anvil 1414 can be comprised of a non-conductive material, or materials, which can have a sufficient dielectric strength to prevent current from flowing between electromagnets and/or between electromagnets and permanent magnets, yet be sufficiently transmissive to magnetic fields. In any event, similar to the above, surgical instrument 1400 can further comprise one or more conductors, such as wires 1484, for example, which can be configured to supply electromagnets 1456 and/or 1457 with a flow of current in order to selectively polarize electromagnets 1456 and 1457. In at least one such embodiment, similar to the above once again, the direction of current flowing through conductors 1484 can be selectively alternated in order to control the poles generated by electromagnets 1456 and/or 1457. In various embodiments, at least a portion of conductors 1484 can be embedded within firing bar 1450. In certain embodiments, firing bar 1450 can comprise two or more laminated layers, wherein, although not illustrated, at least a portion of conductors 1484 can be positioned intermediate the layers, and wherein the layers can be configured to protect and/or electrically insulate conductors 1484 from unintentionally grounding to one another and/or any other portion of surgical instrument 1400. In various embodiments, although not illustrated, conductors 1484 can comprise a flexible ribbon cable which can comprise a plurality of conductors 1484 arranged in parallel and electrically insulated from one another. In any event, the system of permanent magnets and electromagnets within end effector 1406 may be sufficient to advance and retract cutting member 1452 without an additional firing force being transmitted to cutting member 1452 via firing bar 1450, although firing bar 1450 can be configured to transmit an additional firing force to cutting member 1452.

In various embodiments, as outlined above, electromagnets can be positioned on and/or within a cutting member movable within an end effector. In use, the electromagnets can be actuated, or energized, such that they can produce a polarized magnetic field. In at least one such embodiment, each electromagnet can include at least one conductor arranged in a wrapped configuration wherein, when current is supplied to the conductor, the current can generate a field having positive and negative poles. In certain embodiments, as also outlined above, iron cores positioned within the wrapped conductor can amplify the magnetic field produced by the current. Although electromagnets are entirely suitable in various embodiments, any device capable of selectively generating one or more magnetic fields can be used. In at least one embodiment, for example, a polarizable device can include an annular, or toroidal, permanent magnet, and/or iron core, wherein a conductor can extend through an aperture therein, and wherein a magnetic field produced by current flowing through the conductor can be amplified by the annular iron core surrounding the conductor. In various circumstances, the magnetic field produced by such a device may be sufficient to create a usable magnetomotive force as described herein. In certain embodiments, fields produced by a Hall Effect device, or coil, can be utilized to move a cutting member, for example, within an end effector.

Figure 52:
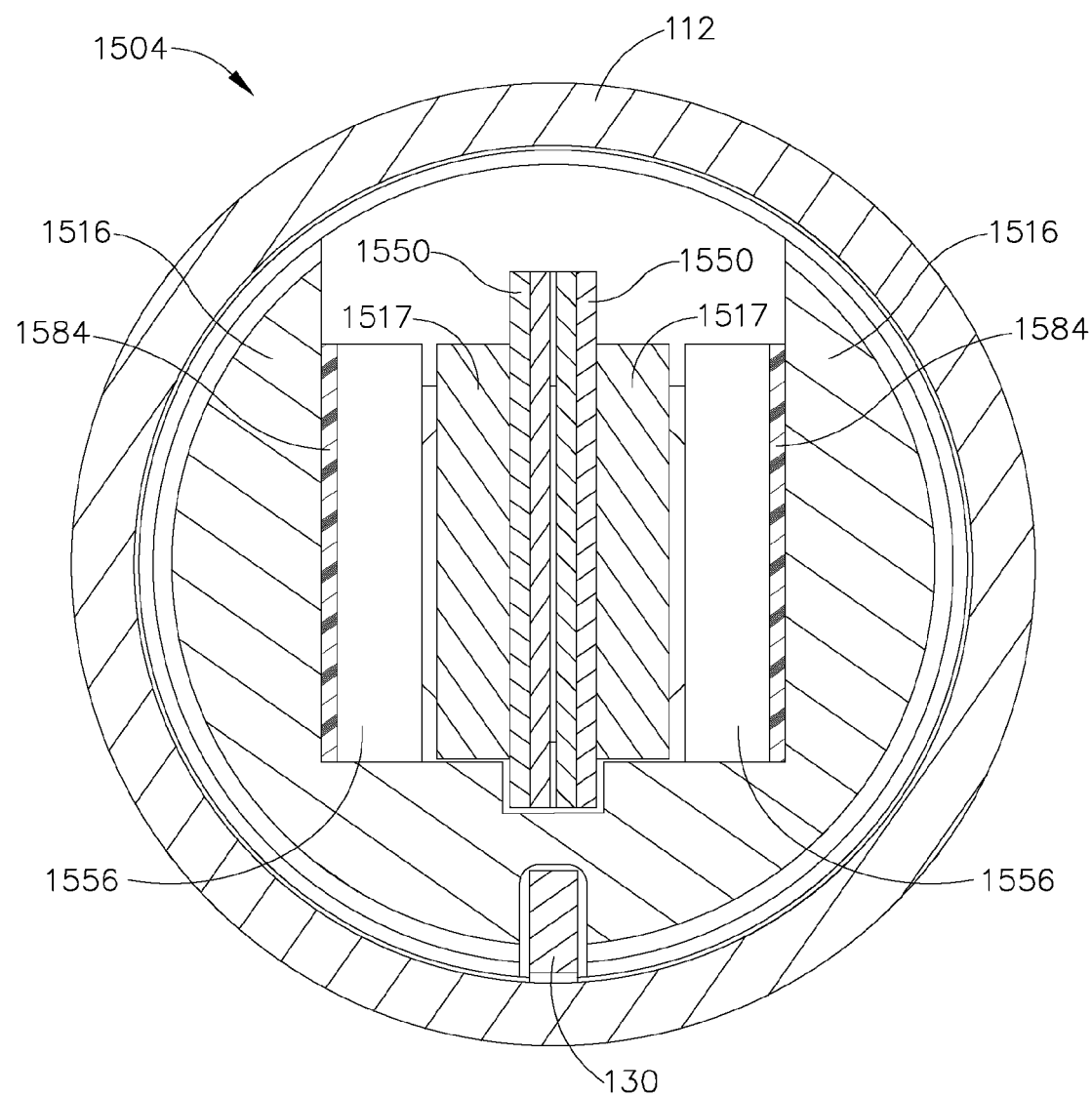
FIG. 52 is a cross-sectional view of the elongate shaft and the movable firing bar of FIGS. 51A-C.
Figure 53:
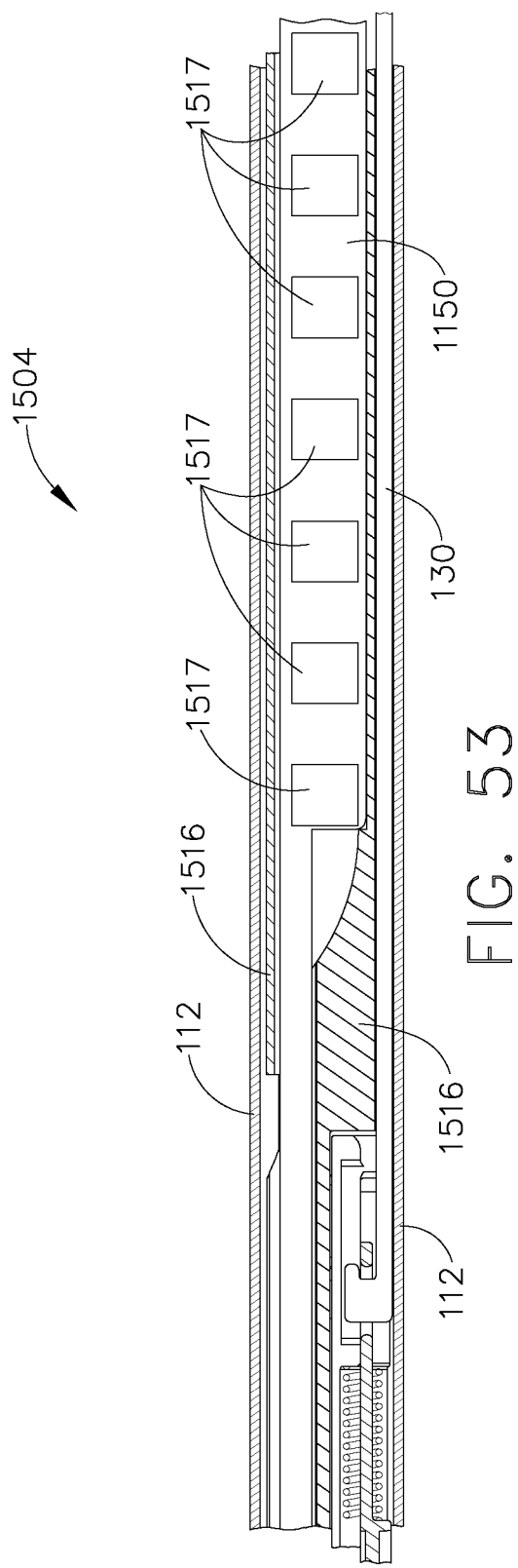
FIG. 53 is another cross-sectional view of the distal portion of the elongate shaft and the movable firing bar of FIG. 51A illustrating the firing bar in a fired position.

In various embodiments, either in addition to or in lieu of the above, a surgical instrument can comprise a system of permanent magnets and electromagnets configured to advance and/or retract a firing bar within an elongate shaft of a surgical instrument. Referring now to FIGS. 51A-51C and 53, surgical instrument 1500 can comprise an elongate shaft 1504 and a firing bar 1550, wherein firing bar 1550 can be advanced distally (FIG. 53) and/or retracted proximally (FIGS. 51A-51C) in order to move a cutting member and/or staple driver, such as cutting member 1452, for example, within an end effector in order to incise tissue and/or deploy staples into the tissue, for example. In certain embodiments, shaft 1504 can comprise spine 1516 which can comprise one or more slots configured to permit firing bar 1550 to slide therein. In at least one such embodiment, elongate shaft 1504 can further comprise one or more electromagnets 1556 mounted to spine 1516 which can be configured to selectively generate one or more magnetic fields. Similar to the above, such magnetic fields can interact with permanent magnets 1517 mounted to drive bar 1550 such that the magnetomotive force generated between electromagnets 1556 and permanent magnets 1517 can move permanent magnets 1517, and drive bar 1550, relative to electromagnets 1556, and spine 1516. In at least one embodiment, referring now to FIG. 52, elongate shaft 1504 can include a first set of electromagnets 1556 positioned on one side of firing bar 1550 and a second set of electromagnets 1556 positioned on the opposite side of firing bar 1550. Correspondingly, a first set of permanent magnets 1517 can be positioned on a first side of firing bar 1550 and a second set of permanent magnets 1517 can be positioned on the opposite side of firing bar 1550. Also similar to the above, the current supplied to electromagnets 1556 can be selectively supplied in order to generate positive poles, negative poles, and/or no polarity within electromagnets 1556, as needed, in order to sufficiently attract and repel the positive and negative poles of permanent magnets 1517. In certain embodiments, referring again to FIG. 52, elongate shaft 1504 can further comprise one or more conductors 1584 which can be configured to supply current to electromagnets 1556. In certain embodiments, conductors 1584 can comprise a ribbon cable positioned intermediate spine 1516 and electromagnets 1556, wherein spine 1516 can be comprised of an electrically non-conductive material, for example.

In various embodiments, further to the above, a surgical instrument can comprise a system including magnetic elements, such as iron cores and/or permanent magnets, for example, and selectively actuatable electromagnets, wherein the system can comprise a linear motor configured to move a firing bar and/or cutting member along a predetermined path, and wherein the path can comprise linear portions and/or curved portions in one or more directions. In various embodiments, the surgical instrument can further comprise a computer, or processor, which can be configured to calculate the appropriate magnitude, duration, and/or direction of the current to be supplied to the electromagnets. In certain embodiments, the surgical instrument can further comprise one or more switches which can be operated by the computer in order to selectively supply current to one or more electromagnets. In certain embodiments, although not illustrated, a surgical instrument can include a handle, an elongate shaft extending from the handle, and an end effector operably coupled to the shaft, wherein the shaft can include one or more conductors wound about an axis or predetermined path within the shaft. In at least one such embodiment, a firing bar, or rod, having an iron portion, for example, can be positioned within an aperture defined by the wound conductors such that, when current is supplied to the conductors, the magnetic field, or fields, generated by the flow of current can move the iron firing bar along the predetermined path. In at least one embodiment, similar to the above, current flowing through the conductors in a first direction can move the firing bar distally within the shaft, for example, and, in addition, current flowing through the conductors in an opposite direction can move the firing bar in an opposite, or proximal, direction.

In various embodiments, an elongate shaft of a surgical instrument can include a solenoid configured to advance and/or retract a firing bar, cutting member, and/or staple driver. In at least one embodiment, referring to FIGS. 54 and 55, surgical instrument 1600 can comprise a handle assembly 1602, an elongate shaft 1604, and a firing bar 1650. Similar to handle assembly 102, handle assembly 1602 can further comprise a trigger (not illustrated) configured to advance and/or retract firing bar 1650. In at least one embodiment, the trigger of handle assembly 1602 can be configured to close, or complete, a circuit when actuated, wherein the closed circuit can be configured to supply current to a solenoid operably engaged with firing bar 1650. In certain embodiments, although not illustrated, handle assembly 1602, for example, can include one or more batteries positioned therein, wherein the batteries, and one or more conductors, can be configured to supply the current to the solenoid. In at least one embodiment, the solenoid can comprise windings 1656 which can be energized by the current in order to generate a polarized magnetic field. Similar to the above, the solenoid can further comprise a magnetic element 1617, which can be comprised of iron, for example, which can be configured to interact with the magnetic field. In use, current flowing in a first direction can be supplied to windings 1656 such that the magnetic field produced by windings 1656 can advance magnetic element 1617, and drive bar 1650 mounted thereto, distally within elongate shaft 1604 as illustrated in FIG. 55. In certain embodiments, the trigger can be released in order to disconnect the supply of current to windings 1656 and stop the advancement of firing bar 1650. In at least one such embodiment, handle assembly 1602 and/or elongate shaft 1604 can include one or more springs (not illustrated) which can be configured to bias magnetic element 1617 and firing bar 1650 back into their starting positions which are illustrated in FIG. 54. In other embodiments, the current flowing within windings 1656 can be reversed when the firing trigger is released such that the polarity of the magnetic field generated by windings 1656 is reversed and magnetic element 1617 is retracted. In yet other embodiments, the trigger of handle assembly 1602 can be actuated once again in order to reverse the current within windings 1656 and retract magnetic element 1617.

In various embodiments, although not illustrated, a surgical instrument can include a handle, a shaft extending from the handle, and an end effector operably coupled to the shaft, wherein the shaft can include a rotatable drive shaft, and wherein the surgical instrument can further include a motor configured to rotate the drive shaft. Various surgical instruments including a motor and a rotatable drive shaft are disclosed in U.S. Pat. No. 7,422,139 to Shelton, IV, et al., entitled MOTOR-DRIVEN SURGICAL CUTTING FASTENING INSTRUMENT WITH TACTILE POSITION FEEDBACK, which issued on Sep. 9, 2008; and U.S. Pat. No. 7,416,101 to Shelton, IV, et al., entitled MOTOR-DRIVEN SURGICAL CUTTING AND FASTENING INSTRUMENT WITH LOADING FORCE FEEDBACK, which issued on Aug. 28, 2008, the entire disclosures of which are incorporated by reference herein. In at least one embodiment, the motor of the surgical instrument can comprise a stepper motor which can be configured to rotate a drive shaft through a predetermined range of rotation. In at least one embodiment, one or more magnetic elements, such as iron cores, for example, can be placed on or embedded within the drive shaft, wherein the magnetic elements can be configured to be detected by one or more sensors positioned within the shaft, for example. In certain embodiments, such sensors can comprise Hall Effect sensors, or coils, which can be configured to detect disruptions within one or more magnetic fields, i.e., disruptions created by the magnetic elements.

In various embodiments, although not illustrated, a surgical instrument can include a system of electromagnets and magnetic elements which can be configured to close and/or open an end effector of a surgical instrument. In at least one such embodiment, similar to the above, the end effector can comprise a staple cartridge channel configured to receive a staple cartridge and, in addition, an anvil rotatably coupled to the staple cartridge channel. In certain embodiments, one or more electromagnets can be positioned within the staple cartridge channel and, in addition, one or more magnetic elements can be positioned within the anvil, wherein, when the electromagnets are energized, or polarized, the electromagnets can generate a magnetic field which can move the magnetic elements toward the electromagnets and, as a result, move the anvil between an open position and a closed position. In some such embodiments, the polarity of the electromagnets can be reversed in order to repel the magnetic elements mounted to the anvil and, as a result, move the anvil between a closed position and an open position. In other embodiments, the current being supplied to the electromagnets can be sufficiently reduced, or disconnected, such that the electromagnets cannot produce a sufficient magnetic field to hold the anvil in its closed position. In at least one such embodiment, the end effector can further comprise a spring which can be configured to bias the anvil into its open position such that, when the electromagnets are sufficiently deenergized as described above, the spring can move the anvil into its open position. In various alternative embodiments, the electromagnets can be configured to bias the anvil into its open position and the spring can be configured to bias the anvil into its closed position.

While the present invention has been illustrated by the description of several embodiments and while the illustrative embodiments have been described in considerable detail, it is not the intention of the applicant to restrict or in any way limit the scope of the appended claims to such detail. Additional advantages and modifications may readily appear to those skilled in the art. Furthermore, although the embodiments disclosed herein have been described in connection with an endoscopic cutting and stapling instrument, other embodiments are envisioned in connection with any suitable medical device. While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Further to the above, the various embodiments of the present invention have been described above in connection with cutting-type surgical instruments. It should be noted, however, that in other embodiments, the surgical instruments disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Further to the above, the various staple cartridges disclosed herein can be disposable. In at least one embodiment, an expended staple cartridge, or an at least partially expended staple cartridge, can be removed from a surgical stapler and replaced with another staple cartridge. In other various embodiments, the staple cartridge may not be removable and/or replaceable during the ordinary use of the surgical instrument but, in some circumstances, may be replaceable while and/or after the surgical stapler is reconditioned as described in greater detail below. In various embodiments, the staple cartridge can be part of a disposable loading unit or end-effector which can further include a staple cartridge carrier, anvil, cutting member, and/or staple driver. In at least one such embodiment, the entire, or at least a portion of, the disposable loading unit or end-effector can be detachably connected to a surgical instrument and can be configured to be replaced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

What is claimed is:

1. A surgical stapler, comprising:
   a shaft;
   an articulation joint, the articulation joint comprising:
      a first joint member, the first joint member defining a ball member positioned about a central axis of the first joint member, wherein the first joint member further defines a first passage at about the central axis of the first joint member through the ball member, and wherein the first joint member comprises first and second magnetic elements positioned opposite one another about the central axis of the first joint member; and
      a second joint member, the second joint member defining a socket at about a central axis of the second joint member, wherein the second joint member further defines a second passage about the central axis of the second joint member through the socket, wherein the socket receives the ball member such that the first and second passages align, and wherein the second joint member comprises third and fourth magnetic elements positioned opposite one another about the central axis of the second joint member, wherein the first magnetic element is aligned with the third magnetic element and the second magnetic element is aligned with the fourth magnetic element;
   a current source to selectively provide a first current to the first magnetic element and a second current to the second magnetic element, wherein, in a first mode of the current source, the first current is directed to cause a first level of magnetic attraction between the first magnetic element and the third magnetic element and the second current is directed to cause a second level of magnetic attraction between the second magnetic element and the fourth magnetic element such that the articulation joint is articulated towards the first magnetic element by a first amount;
   an end effector, wherein said end effector is movably coupled to said shaft by said articulation joint, said end effector comprising:
      a staple cartridge channel configured to receive a staple cartridge; and
      an anvil movably coupled to said staple cartridge channel; and
   a firing member extending proximally from the end effector through the first and second passages.

2. The surgical stapler of claim 1, wherein said first magnetic element comprises an electromagnet energizable by the first current from said power source.

3. The surgical stapler of claim 1, further comprising an actuator configured to switch the polarity of the first current supplied to said electromagnet.

4. (c): The surgical stapler of claim 1, wherein said first magnetic element is configured to generate a magnetic field.

5. The surgical stapler of claim 4, wherein said magnetic field is sufficient to lock the position of said end effector relative to said shaft.

6. The surgical stapler of claim 1, wherein said second magnetic element comprises a permanent magnet.

7. The surgical stapler of claim 1, wherein said second magnetic element comprises iron.

8. The surgical stapler of claim 1, wherein said first joint member is configured to articulate relative to said shaft, and wherein said end effector is configured to articulate relative to said second joint member.

9. The surgical stapler of claim 1, wherein one of said ball member and said socket comprises a flange, wherein the other of said ball member and said socket comprises a groove configured to receive said flange, and wherein said flange and said groove are configured to define a plane in which said end effector can articulate relative to said shaft.

10. The surgical stapler of claim 1, further comprising an elastic rod extending through the first and second passages, wherein said elastic rod is configured to bias said end effector into a non-articulated position.

11. A surgical stapler, comprising:
    a shaft;
    an articulation joint, comprising:
       a first joint member comprising a first electromagnet and a second electromagnet;
       a second joint member comprising a first permanent magnetic element and a second permanent magnetic element, wherein said second joint member is articulatable relative to said first joint member, wherein the first electromagnet is aligned with the first permanent magnetic element and the second electromagnet is aligned with the second permanent magnetic element;
    an end effector, wherein said end effector is movably coupled to said shaft by said articulation joint, said end effector comprising:
       a staple cartridge channel configured to receive a staple cartridge; and
       an anvil movably coupled to said staple cartridge channel; and
    a current source to selectively provide a first current to the first electromagnet and a second current to the second electromagnet, wherein in a first mode of the current source, the first current is directed to cause a first level of magnetic attraction between the first electromagnet and the first permanent magnetic element, and the second current is directed to cause a second level of magnetic attraction between the second electromagnet and the second permanent magnetic element such that the articulation joint is articulated towards the first magnetic element by a first amount.

12. The surgical stapler of claim 11, wherein said articulation joint further comprises an articulation axis, wherein said first electromagnet is positioned on a first side of said articulation axis, and wherein said second electromagnet is positioned on a substantially opposite side of said articulation axis.

13. The surgical stapler of claim 12, wherein said first magnetic element is aligned with said first electromagnet along a first axis, wherein said second magnetic element is aligned with said second electromagnet along a second axis, wherein said first axis is substantially parallel to said articulation axis, and wherein said second axis is substantially parallel to said articulation axis.

14. The surgical stapler of claim 11, wherein said first joint member further comprises a third electromagnet and a fourth electromagnet, wherein said second joint member further comprises a third magnetic element and a fourth magnetic element, wherein said third electromagnet is configured to selectively generate a third magnetic field configured to move said third magnetic element relative to said third electromagnet and articulate said end effector in a third direction, and wherein said fourth electromagnet is configured to selectively generate a fourth magnetic field configured to move said fourth magnetic element relative to said fourth electromagnet and articulate said end effector in a fourth direction.

* * * * *